(12) United States Patent
Bruchman et al.

(10) Patent No.: US 12,702,545 B2
(45) Date of Patent: Aug. 11, 2026

(54) PROSTHETIC VALVES, FRAMES AND LEAFLETS AND METHODS THEREOF

(71) Applicant: EDWARDS LIFESCIENCES CORPORATION, Irvine, CA (US)

(72) Inventors: William C. Bruchman, Camp Verde, AZ (US); Daniel A. Crawford, Flagstaff, AZ (US); Logan R. Hagaman, Flagstaff, AZ (US); Cody L. Hartman, Flagstaff, AZ (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 19/091,365

(22) Filed: Mar. 26, 2025

(65) Prior Publication Data

US 2025/0221820 A1 Jul. 10, 2025

Related U.S. Application Data

(63) Continuation of application No. 17/140,366, filed on Jan. 4, 2021, now Pat. No. 12,295,835, which is a (Continued)

(51) Int. Cl.
*A61F 2/24* (2006.01)

(52) U.S. Cl.
CPC .......... *A61F 2/2412* (2013.01); *A61F 2/2415* (2013.01); *A61F 2/2418* (2013.01);

(Continued)

(58) Field of Classification Search
CPC .... A61F 2/2409; A61F 2/2412; A61F 2/2418; A61F 2/915; A61F 2002/9155;

(Continued)

(56) References Cited

U.S. PATENT DOCUMENTS

| | | | |
|---|---|---|---|
| 654,799 | A | 7/1900 | Levett |
| 3,409,013 | A | 11/1968 | Henry |

(Continued)

FOREIGN PATENT DOCUMENTS

| | | | |
|---|---|---|---|
| CA | 2462509 | A1 | 4/2003 |
| CN | 101057796 | A | 10/2007 |

(Continued)

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

(Continued)

*Primary Examiner* — Leslie A Lopez
(74) *Attorney, Agent, or Firm* — Klarquist Sparkman, LLP; Joel B. German

(57) ABSTRACT

Prosthetic heart valves including radially compressible and expandable frames. A frame includes a plurality of interconnected frame elements forming a plurality of cells, which are arranged in a first circumferential row of cells defining an inflow end of the frame and a second circumferential row of cells defining an outflow end of the frame. An outflow portion of the second row of cells includes a circumferential row of angled frame elements interconnected to each other at a plurality of upper junctions and a plurality of lower junctions. The upper junctions define the outflow end of the frame and the lower junctions point toward the inflow end of the frame. The lower junctions are not connected to other portions of the frame.

18 Claims, 25 Drawing Sheets

Related U.S. Application Data continuation of application No. 15/662,571, filed on Jul. 28, 2017, now Pat. No. 10,881,507, which is a continuation of application No. 14/133,563, filed on Dec. 18, 2013, now Pat. No. 9,737,398.

(60) Provisional application No. 61/802,116, filed on Mar. 15, 2013, provisional application No. 61/739,721, filed on Dec. 19, 2012.

(52) U.S. Cl.
CPC ................ *A61F 2230/0023* (2013.01); *A61F 2230/0026* (2013.01)

(58) Field of Classification Search
CPC .. A61F 2002/91558; A61F 2002/91566; A61F 2230/0054
See application file for complete search history.

(56) References Cited

U.S. PATENT DOCUMENTS 3,548,417 A 12/1970 Kischer et al.
3,587,115 A 6/1971 Shiley
3,657,744 A 4/1972 Ersek
3,671,979 A 6/1972 Moulopoulos
3,714,671 A 2/1973 Goodenough et al.
3,739,402 A 6/1973 Kahn et al.
3,755,823 A 9/1973 Hancock
3,938,197 A 2/1976 Milo
3,953,566 A 4/1976 Gore
4,035,849 A 7/1977 Angell et al.
4,053,084 A 10/1977 Anderson
4,056,854 A 11/1977 Boretos et al.
4,106,129 A 8/1978 Carpentier et al.
4,178,639 A 12/1979 Bokros
4,187,390 A 2/1980 Gore
4,222,126 A 9/1980 Boretos et al.
4,265,694 A 5/1981 Boretos et al.
4,297,749 A 11/1981 Davis et al.
RE30,912 E 4/1982 Hancock
4,332,035 A 6/1982 Mano
4,339,831 A 7/1982 Johnson
4,340,091 A 7/1982 Skelton et al.
4,343,048 A 8/1982 Ross et al.
4,345,340 A 8/1982 Rosen
4,373,216 A 2/1983 Klawitter
4,406,022 A 9/1983 Roy
4,417,360 A 11/1983 Moasser
4,441,216 A 4/1984 Ionescu et al.
4,470,157 A 9/1984 Love
4,477,930 A 10/1984 Totten et al.
4,501,030 A 2/1985 Lane
4,535,483 A 8/1985 Klawitter et al.
4,556,996 A 12/1985 Wallace
4,574,803 A 3/1986 Storz
4,592,340 A 6/1986 Boyles
4,605,407 A 8/1986 Black et al.
4,612,011 A 9/1986 Kautzky
4,626,255 A 12/1986 Reichart et al.
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,759,759 A 7/1988 Walker et al.
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,820,299 A 4/1989 Philippe et al.
4,829,990 A 5/1989 Thuroff et al.
4,851,000 A 7/1989 Gupta
4,851,001 A 7/1989 Taheri
4,856,516 A 8/1989 Hillstead
4,877,661 A 10/1989 House et al.
4,878,495 A 11/1989 Grayzel
4,878,906 A 11/1989 Lindemann et al.
4,883,458 A 11/1989 Shiber
4,922,905 A 5/1990 Strecker
4,955,899 A 9/1990 Della et al.
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,026,513 A 6/1991 House et al.
5,032,128 A 7/1991 Alonso
5,037,434 A 8/1991 Lane
5,047,041 A 9/1991 Samuels
5,059,177 A 10/1991 Towne et al.
5,064,435 A 11/1991 Porter
5,071,609 A 12/1991 Tu et al.
5,080,668 A 1/1992 Bolz et al.
5,085,635 A 2/1992 Cragg
5,089,015 A 2/1992 Ross
5,123,918 A 6/1992 Perrier et al.
5,152,771 A 10/1992 Sabbaghian et al.
5,163,953 A 11/1992 Vince
5,163,955 A 11/1992 Love et al.
5,167,628 A 12/1992 Boyles
5,192,297 A 3/1993 Hull
5,266,073 A 11/1993 Wall
5,282,847 A 2/1994 Trescony et al.
5,332,402 A 7/1994 Teitelbaum
5,360,444 A 11/1994 Kusuhara
5,397,351 A 3/1995 Pavcnik et al.
5,411,055 A 5/1995 Kane
5,411,552 A 5/1995 Andersen et al.
5,415,667 A 5/1995 Frater
5,469,868 A 11/1995 Reger
5,476,589 A 12/1995 Bacino
5,480,424 A 1/1996 Cox
5,489,297 A 2/1996 Duran
5,500,014 A 3/1996 Quijano et al.
5,534,007 A 7/1996 St et al.
5,545,209 A 8/1996 Roberts et al.
5,549,663 A 8/1996 Cottone, Jr.
5,549,665 A 8/1996 Vesely et al.
5,554,183 A 9/1996 Nazari
5,558,644 A 9/1996 Boyd et al.
5,562,729 A 10/1996 Purdy et al.
5,571,175 A 11/1996 Vanney et al.
5,584,803 A 12/1996 Stevens et al.
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,791 A 5/1997 Bokros et al.
5,628,792 A 5/1997 Lentell
5,639,274 A 6/1997 Fischell et al.
5,665,115 A 9/1997 Cragg
5,673,102 A 9/1997 Suzuki et al.
5,708,044 A 1/1998 Branca
5,716,417 A 2/1998 Girard et al.
5,718,973 A 2/1998 Lewis et al.
5,728,068 A 3/1998 Leone et al.
5,749,852 A 5/1998 Schwab et al.
5,749,890 A 5/1998 Shaknovich
5,752,934 A 5/1998 Campbell et al.
5,756,476 A 5/1998 Epstein et al.
5,759,192 A 6/1998 Saunders
5,769,812 A 6/1998 Stevens et al.
5,772,884 A 6/1998 Tanaka et al.
5,800,508 A 9/1998 Goicoechea et al.
5,814,405 A 9/1998 Branca et al.
5,824,043 A 10/1998 Cottone, Jr.
5,843,158 A 12/1998 Lenker et al.
5,843,161 A 12/1998 Solovay
5,843,171 A 12/1998 Campbell et al.
5,853,419 A 12/1998 Imran
5,855,597 A 1/1999 Jayaraman

(56) References Cited

U.S. PATENT DOCUMENTS

| | | | |
|---|---|---|---|
| 5,855,601 | A | 1/1999 | Bessler et al. |
| 5,855,602 | A | 1/1999 | Angell |
| 5,925,061 | A | 7/1999 | Ogi et al. |
| 5,925,063 | A | 7/1999 | Khosravi |
| 5,928,281 | A | 7/1999 | Huynh et al. |
| 5,935,162 | A | 8/1999 | Dang |
| 5,935,163 | A | 8/1999 | Gabbay |
| 5,944,654 | A | 8/1999 | Crawford |
| 5,957,949 | A | 9/1999 | Leonhardt et al. |
| 5,957,974 | A | 9/1999 | Thompson et al. |
| 6,010,529 | A | 1/2000 | Herweck et al. |
| 6,013,854 | A | 1/2000 | Moriuchi |
| 6,019,785 | A | 2/2000 | Strecker |
| 6,027,525 | A | 2/2000 | Suh et al. |
| 6,035,896 | A | 3/2000 | Liardet |
| 6,042,588 | A | 3/2000 | Munsinger et al. |
| 6,042,606 | A | 3/2000 | Frantzen |
| 6,086,612 | A | 7/2000 | Jansen |
| 6,110,198 | A | 8/2000 | Fogarty et al. |
| 6,117,169 | A | 9/2000 | Moe |
| 6,129,758 | A | 10/2000 | Love |
| 6,132,473 | A | 10/2000 | Williams et al. |
| 6,161,399 | A | 12/2000 | Jayaraman |
| 6,171,335 | B1 | 1/2001 | Wheatley et al. |
| 6,174,327 | B1 | 1/2001 | Mertens et al. |
| 6,174,329 | B1 | 1/2001 | Callol et al. |
| 6,174,331 | B1 | 1/2001 | Moe et al. |
| 6,190,406 | B1 | 2/2001 | Duerig et al. |
| 6,197,143 | B1 | 3/2001 | Bodnar |
| 6,210,408 | B1 | 4/2001 | Chandrasekaran et al. |
| 6,217,585 | B1 | 4/2001 | Houser et al. |
| 6,217,609 | B1 | 4/2001 | Haverkost |
| 6,221,091 | B1 | 4/2001 | Khosravi |
| 6,231,602 | B1 | 5/2001 | Carpentier et al. |
| 6,245,012 | B1 | 6/2001 | Kleshinski |
| 6,245,102 | B1 | 6/2001 | Jayaraman |
| 6,261,320 | B1 | 7/2001 | Tam et al. |
| 6,261,620 | B1 | 7/2001 | Leadbeater |
| 6,283,995 | B1 | 9/2001 | Moe et al. |
| 6,287,334 | B1 | 9/2001 | Moll et al. |
| 6,299,637 | B1 | 10/2001 | Shaolian et al. |
| 6,302,906 | B1 | 10/2001 | Goicoechea et al. |
| 6,328,763 | B1 | 12/2001 | Love et al. |
| 6,338,740 | B1 | 1/2002 | Carpentier |
| 6,352,547 | B1 | 3/2002 | Brown et al. |
| 6,352,552 | B1 | 3/2002 | Levinson et al. |
| 6,379,382 | B1 | 4/2002 | Yang |
| 6,440,764 | B1 | 8/2002 | Focht et al. |
| 6,461,665 | B1 | 10/2002 | Scholander |
| 6,468,660 | B2 | 10/2002 | Ogle et al. |
| 6,482,228 | B1 | 11/2002 | Norred |
| 6,488,701 | B1 | 12/2002 | Nolting et al. |
| 6,488,704 | B1 | 12/2002 | Connelly et al. |
| 6,527,979 | B2 | 3/2003 | Constantz et al. |
| 6,541,589 | B1 | 4/2003 | Baillie |
| 6,558,418 | B2 | 5/2003 | Carpentier et al. |
| 6,582,464 | B2 | 6/2003 | Gabbay |
| 6,613,086 | B1 | 9/2003 | Moe et al. |
| 6,620,190 | B1 | 9/2003 | Colone |
| 6,626,939 | B1 | 9/2003 | Burnside et al. |
| 6,673,102 | B1 | 1/2004 | Vonesh et al. |
| 6,673,107 | B1 | 1/2004 | Brandt et al. |
| 6,689,123 | B2 | 2/2004 | Pinchasik |
| 6,716,244 | B2 | 4/2004 | Klaco |
| 6,726,715 | B2 | 4/2004 | Sutherland |
| 6,730,120 | B2 | 5/2004 | Berg et al. |
| 6,733,525 | B2 | 5/2004 | Yang et al. |
| 6,755,856 | B2 | 6/2004 | Fierens et al. |
| 6,755,857 | B2 | 6/2004 | Peterson et al. |
| 6,758,858 | B2 | 7/2004 | Mccrea et al. |
| 6,769,161 | B2 | 8/2004 | Brown et al. |
| 6,783,542 | B2 | 8/2004 | Eidenschink |
| 6,830,584 | B1 | 12/2004 | Seguin |
| 6,890,350 | B1 | 5/2005 | Walak |
| 6,916,338 | B2 | 7/2005 | Speziali |
| 7,018,406 | B2 | 3/2006 | Seguin et al. |
| 7,049,380 | B1 | 5/2006 | Chang et al. |
| 7,083,642 | B2 | 8/2006 | Sirhan et al. |
| 7,096,554 | B2 | 8/2006 | Austin et al. |
| 7,105,018 | B1 | 9/2006 | Yip et al. |
| 7,137,184 | B2 | 11/2006 | Schreck |
| 7,163,556 | B2 | 1/2007 | Xie et al. |
| 7,225,518 | B2 | 6/2007 | Eidenschink et al. |
| 7,247,167 | B2 | 7/2007 | Gabbay |
| 7,276,078 | B2 | 10/2007 | Spenser et al. |
| 7,316,710 | B1 | 1/2008 | Cheng et al. |
| 7,374,571 | B2 | 5/2008 | Pease et al. |
| 7,419,678 | B2 | 9/2008 | Falotico |
| 7,462,191 | B2 | 12/2008 | Spenser et al. |
| 7,513,909 | B2 | 4/2009 | Lane et al. |
| 7,531,611 | B2 | 5/2009 | Sabol et al. |
| 7,563,277 | B2 | 7/2009 | Case et al. |
| 7,727,274 | B2 | 6/2010 | Zilla et al. |
| 7,758,640 | B2 | 7/2010 | Vesely |
| 7,785,366 | B2 | 8/2010 | Maurer et al. |
| 7,811,314 | B2 | 10/2010 | Fierens et al. |
| 7,815,763 | B2 | 10/2010 | Fierens et al. |
| 7,879,085 | B2 | 2/2011 | Sowinski et al. |
| 7,887,562 | B2 | 2/2011 | Young et al. |
| 7,927,364 | B2 | 4/2011 | Fierens et al. |
| 7,927,365 | B2 | 4/2011 | Fierens et al. |
| 7,959,665 | B2 | 6/2011 | Pienknagura |
| 7,959,672 | B2 | 6/2011 | Salahieh et al. |
| 8,029,556 | B2 | 10/2011 | Rowe |
| 8,048,440 | B2 | 11/2011 | Chang et al. |
| 8,092,523 | B2 | 1/2012 | Li et al. |
| 8,128,686 | B2 | 3/2012 | Paul, Jr. et al. |
| 8,167,935 | B2 | 5/2012 | Mcguckin, Jr. et al. |
| 8,246,678 | B2 | 8/2012 | Salahieh et al. |
| 8,252,037 | B2 | 8/2012 | Styrc et al. |
| 8,303,647 | B2 | 11/2012 | Case |
| 8,348,998 | B2 | 1/2013 | Pintor et al. |
| 8,449,606 | B2 | 5/2013 | Eliasen et al. |
| 8,545,525 | B2 | 10/2013 | Surti et al. |
| 8,585,757 | B2 | 11/2013 | Agathos |
| 8,637,144 | B2 | 1/2014 | Ford |
| 8,652,203 | B2 | 2/2014 | Quadri et al. |
| 8,685,055 | B2 | 4/2014 | Vantassel et al. |
| 8,722,178 | B2 | 5/2014 | Ashmead et al. |
| 8,728,103 | B2 | 5/2014 | Surti et al. |
| 8,747,463 | B2 | 6/2014 | Fogarty et al. |
| 8,801,774 | B2 | 8/2014 | Silverman |
| 8,808,848 | B2 | 8/2014 | Bacino |
| 8,845,709 | B2 | 9/2014 | Styrc et al. |
| 8,852,272 | B2 | 10/2014 | Gross et al. |
| 8,870,948 | B1 | 10/2014 | Erzberger et al. |
| 8,936,634 | B2 | 1/2015 | Irwin et al. |
| 9,039,757 | B2 | 5/2015 | Mclean et al. |
| 9,101,696 | B2 | 8/2015 | Leontein et al. |
| 9,107,771 | B2 | 8/2015 | Wubbeling et al. |
| 9,125,740 | B2 | 9/2015 | Morriss et al. |
| 9,198,787 | B2 | 12/2015 | Kratzberg et al. |
| 9,241,695 | B2 | 1/2016 | Peavey et al. |
| 9,295,552 | B2 | 3/2016 | McLean et al. |
| 9,345,601 | B2 | 5/2016 | Jantzen et al. |
| 9,375,308 | B2 | 6/2016 | Norris |
| 9,399,085 | B2 | 7/2016 | Cleek et al. |
| 9,554,786 | B2 | 1/2017 | Carley et al. |
| 9,554,900 | B2 | 1/2017 | Bruchman et al. |
| 9,681,948 | B2 | 6/2017 | Levi et al. |
| 9,737,422 | B2 | 8/2017 | Armstrong et al. |
| 9,743,932 | B2 | 8/2017 | Amplatz et al. |
| 9,839,540 | B2 | 12/2017 | Armstrong et al. |
| 9,931,204 | B2 | 4/2018 | Rothstein et al. |
| 9,968,443 | B2 | 5/2018 | Bruchman et al. |
| 10,335,298 | B2 | 7/2019 | Armstrong et al. |
| D926,322 | S | 7/2021 | Bennett et al. |
| 11,055,112 | B2 | 7/2021 | Miller et al. |
| 11,109,953 | B2 | 9/2021 | Richart |
| 11,224,509 | B2 | 1/2022 | Dasi et al. |
| 2001/0053929 | A1 | 12/2001 | Vonesh et al. |
| 2002/0026094 | A1 | 2/2002 | Roth |
| 2002/0032481 | A1 | 3/2002 | Gabbay |
| 2002/0045936 | A1 | 4/2002 | Moe |

(56) References Cited

U.S. PATENT DOCUMENTS

2002/0055773 A1 5/2002 Campbell et al.
2002/0076542 A1 6/2002 Kramer et al.
2002/0082687 A1 6/2002 Moe
2002/0133226 A1 9/2002 Marquez et al.
2002/0138135 A1 9/2002 Duerig et al.
2002/0143390 A1 10/2002 Ishii
2002/0151953 A1 10/2002 Chobotov et al.
2002/0151956 A1 10/2002 Chobotov et al.
2002/0173842 A1 11/2002 Buchanan
2002/0183840 A1 12/2002 Lapeyre et al.
2002/0198588 A1 12/2002 Armstrong et al.
2003/0040791 A1 2/2003 Oktay
2003/0050694 A1 3/2003 Yang et al.
2003/0055494 A1 3/2003 Bezuidenhout et al.
2003/0055496 A1 3/2003 Cai et al.
2003/0060871 A1 3/2003 Hill et al.
2003/0074052 A1 4/2003 Besselink
2003/0097175 A1 5/2003 O'Connor et al.
2003/0100939 A1 5/2003 Yodfat et al.
2003/0125805 A1 7/2003 Johnson et al.
2003/0158597 A1 8/2003 Quiachon et al.
2003/0180488 A1 9/2003 Lim et al.
2003/0209835 A1 11/2003 Chun et al.
2003/0212454 A1 11/2003 Scott et al.
2003/0229394 A1 12/2003 Ogle et al.
2004/0024448 A1 2/2004 Chang et al.
2004/0024451 A1 2/2004 Johnson et al.
2004/0024452 A1 2/2004 Kruse et al.
2004/0026245 A1 2/2004 Agarwal et al.
2004/0044400 A1 3/2004 Cheng et al.
2004/0044401 A1 3/2004 Bales et al.
2004/0078074 A1 4/2004 Anderson et al.
2004/0133266 A1 7/2004 Clerc et al.
2004/0176839 A1 9/2004 Huynh et al.
2004/0186558 A1 9/2004 Pavcnik et al.
2004/0224442 A1 11/2004 Grigg
2004/0243222 A1 12/2004 Osborne et al.
2004/0260277 A1 12/2004 Maguire
2004/0260389 A1 12/2004 Case et al.
2004/0260393 A1 12/2004 Rahdert et al.
2005/0010285 A1 1/2005 Lambrecht et al.
2005/0027348 A1 2/2005 Case et al.
2005/0075725 A1 4/2005 Rowe
2005/0075728 A1 4/2005 Nguyen et al.
2005/0080476 A1 4/2005 Gunderson et al.
2005/0119722 A1 6/2005 Styrc et al.
2005/0137680 A1 6/2005 Ortiz et al.
2005/0137682 A1 6/2005 Justino
2005/0137686 A1 6/2005 Salahieh et al.
2005/0149181 A1 7/2005 Eberhardt
2005/0188525 A1 9/2005 Weber et al.
2005/0203617 A1 9/2005 Forster et al.
2005/0234546 A1 10/2005 Nugent et al.
2005/0261765 A1 11/2005 Liddicoat
2005/0283224 A1 12/2005 King
2006/0004469 A1 1/2006 Sokel
2006/0008497 A1 1/2006 Gabbay
2006/0009835 A1 1/2006 Osborne et al.
2006/0015171 A1 1/2006 Armstrong
2006/0036311 A1 2/2006 Nakayama et al.
2006/0041091 A1 2/2006 Chang et al.
2006/0058872 A1 3/2006 Salahieh et al.
2006/0074484 A1 4/2006 Huber
2006/0106337 A1 5/2006 Blankenship
2006/0108090 A1 5/2006 Ederer et al.
2006/0122693 A1 6/2006 Biadillah et al.
2006/0135985 A1 6/2006 Cox et al.
2006/0149350 A1 7/2006 Patel et al.
2006/0154365 A1 7/2006 Ratcliffe et al.
2006/0161241 A1 7/2006 Barbut et al.
2006/0183383 A1 8/2006 Asmus et al.
2006/0190070 A1 8/2006 Dieck et al.
2006/0229718 A1 10/2006 Marquez
2006/0259136 A1 11/2006 Nguyen et al.
2006/0259137 A1 11/2006 Artof et al.
2006/0265053 A1 11/2006 Hunt
2006/0271091 A1 11/2006 Campbell et al.
2006/0276813 A1 12/2006 Greenberg
2006/0276883 A1 12/2006 Greenberg et al.
2006/0276888 A1 12/2006 Lee et al.
2006/0282162 A1 12/2006 Nguyen et al.
2006/0287717 A1 12/2006 Rowe et al.
2006/0290027 A1 12/2006 O'Connor et al.
2007/0010876 A1 1/2007 Salahieh et al.
2007/0010877 A1 1/2007 Salahieh et al.
2007/0012624 A1 1/2007 Bacino et al.
2007/0021826 A1 1/2007 Case et al.
2007/0060999 A1 3/2007 Randall et al.
2007/0100435 A1 5/2007 Case et al.
2007/0112422 A1 5/2007 Dehdashtian et al.
2007/0118210 A1 5/2007 Pinchuk
2007/0129786 A1 6/2007 Beach et al.
2007/0162102 A1 7/2007 Ryan et al.
2007/0203503 A1 8/2007 Salahieh et al.
2007/0203575 A1 8/2007 Forster et al.
2007/0207186 A1 9/2007 Scanlon et al.
2007/0207816 A1 9/2007 Spain
2007/0208417 A1 9/2007 Agnew
2007/0208421 A1 9/2007 Quigley
2007/0208550 A1 9/2007 Cao et al.
2007/0213800 A1 9/2007 Fierens et al.
2007/0213813 A1 9/2007 Von Segesser et al.
2007/0233228 A1 10/2007 Eberhardt et al.
2007/0244552 A1 10/2007 Salahieh et al.
2007/0250146 A1 10/2007 Cully et al.
2007/0250153 A1 10/2007 Cully et al.
2007/0254012 A1 11/2007 Ludwig et al.
2007/0260305 A1 11/2007 Drews et al.
2007/0265700 A1 11/2007 Eliasen et al.
2008/0021546 A1 1/2008 Patz et al.
2008/0026190 A1 1/2008 King et al.
2008/0039934 A1 2/2008 Styrc
2008/0051876 A1 2/2008 Ta et al.
2008/0065198 A1 3/2008 Quintessenza
2008/0071369 A1 3/2008 Tuval et al.
2008/0082154 A1 4/2008 Tseng et al.
2008/0086202 A1 4/2008 Lapeyre
2008/0097401 A1 4/2008 Trapp et al.
2008/0097579 A1 4/2008 Shanley et al.
2008/0097582 A1 4/2008 Shanley et al.
2008/0114442 A1 5/2008 Mitchell et al.
2008/0119943 A1 5/2008 Armstrong et al.
2008/0133004 A1 6/2008 White
2008/0140178 A1 6/2008 Rasmussen et al.
2008/0154355 A1* 6/2008 Benichou .............. A61F 2/2418
623/1.26
2008/0183271 A1 7/2008 Frawley et al.
2008/0195199 A1 8/2008 Kheradvar et al.
2008/0208327 A1 8/2008 Rowe
2008/0220041 A1 9/2008 Brito et al.
2008/0228263 A1 9/2008 Ryan
2008/0243245 A1 10/2008 Thambar et al.
2008/0255660 A1 10/2008 Guyenot et al.
2008/0275537 A1 11/2008 Limon
2008/0294248 A1 11/2008 Yang et al.
2008/0319531 A1 12/2008 Doran et al.
2009/0005854 A1 1/2009 Huang et al.
2009/0030499 A1 1/2009 Bebb et al.
2009/0036976 A1 2/2009 Beach et al.
2009/0043373 A1 2/2009 Arnault et al.
2009/0099640 A1 4/2009 Weng
2009/0104247 A1 4/2009 Pacetti
2009/0112309 A1 4/2009 Jaramillo et al.
2009/0117334 A1 5/2009 Sogard et al.
2009/0118826 A1 5/2009 Khaghani
2009/0125118 A1 5/2009 Gong
2009/0138079 A1 5/2009 Tuval et al.
2009/0157175 A1 6/2009 Benichou
2009/0182413 A1 7/2009 Burkart et al.
2009/0240320 A1 9/2009 Tuval et al.
2009/0259306 A1* 10/2009 Rowe .................... A61F 2/2418
623/2.12
2009/0264997 A1 10/2009 Salahieh et al.
2009/0276039 A1 11/2009 Meretei

(56) References Cited

U.S. PATENT DOCUMENTS

2009/0276040 A1 11/2009 Rowe et al.
2009/0281609 A1 11/2009 Benichou et al.
2009/0281619 A1 11/2009 Le et al.
2009/0287296 A1 11/2009 Manasse
2009/0287305 A1 11/2009 Amalaha
2009/0292350 A1 11/2009 Eberhardt et al.
2009/0299452 A1 12/2009 Eidenschink et al.
2009/0306762 A1 12/2009 McCullagh et al.
2009/0306766 A1 12/2009 McDermott et al.
2009/0319037 A1 12/2009 Rowe et al.
2010/0004735 A1 1/2010 Yang et al.
2010/0016940 A1 1/2010 Shokoohi et al.
2010/0023114 A1 1/2010 Chambers et al.
2010/0036021 A1 2/2010 Lee et al.
2010/0049294 A1 2/2010 Zukowski et al.
2010/0049313 A1 2/2010 Alon et al.
2010/0082089 A1 4/2010 Quadri et al.
2010/0082094 A1 4/2010 Quadri et al.
2010/0094394 A1 4/2010 Beach et al.
2010/0094405 A1 4/2010 Cottone
2010/0100176 A1 4/2010 Elizondo et al.
2010/0106240 A1 4/2010 Duggal et al.
2010/0114307 A1 5/2010 Agnew et al.
2010/0131056 A1 5/2010 Lapeyre
2010/0137998 A1 6/2010 Sobrino-Serrano et al.
2010/0152839 A1 6/2010 Shandas et al.
2010/0159171 A1 6/2010 Clough
2010/0168844 A1 7/2010 Toomes et al.
2010/0185274 A1 7/2010 Moaddeb et al.
2010/0191320 A1 7/2010 Straubinger et al.
2010/0204785 A1 8/2010 Alkhatib
2010/0217382 A1 8/2010 Chau et al.
2010/0248324 A1 9/2010 Xu et al.
2010/0249908 A1* 9/2010 Chau .................... A61F 2/2418 623/1.26
2010/0249923 A1 9/2010 Alkhatib et al.
2010/0256723 A1* 10/2010 Murray ................ A61F 2/2418 623/1.2
2010/0256738 A1 10/2010 Berglund
2010/0262231 A1 10/2010 Tuval et al.
2010/0286760 A1 11/2010 Beach et al.
2010/0305685 A1* 12/2010 Millwee ................ A61F 2/2418 623/1.26
2011/0009953 A1 1/2011 Luk et al.
2011/0015729 A1 1/2011 Jimenez et al.
2011/0040366 A1 2/2011 Goetz et al.
2011/0054515 A1 3/2011 Bridgeman et al.
2011/0064781 A1 3/2011 Cleek et al.
2011/0087318 A1 4/2011 Daugherty et al.
2011/0137397 A1 6/2011 Chau et al.
2011/0160836 A1 6/2011 Behan
2011/0172784 A1 7/2011 Richter et al.
2011/0208283 A1 8/2011 Rust
2011/0218619 A1 9/2011 Benichou et al.
2011/0257739 A1 10/2011 Corbett
2011/0282439 A1 11/2011 Thill et al.
2011/0295363 A1 12/2011 Girard et al.
2012/0030090 A1 2/2012 Johnston et al.
2012/0035722 A1 2/2012 Tuval
2012/0078357 A1 3/2012 Conklin
2012/0089223 A1 4/2012 Nguyen et al.
2012/0101567 A1 4/2012 Jansen
2012/0116496 A1 5/2012 Chuter et al.
2012/0116498 A1 5/2012 Chuter et al.
2012/0123530 A1 5/2012 Carpentier et al.
2012/0130468 A1 5/2012 Khosravi et al.
2012/0130471 A1 5/2012 Shoemaker et al.
2012/0215303 A1 8/2012 Quadri et al.
2012/0253453 A1 10/2012 Bruchman et al.
2012/0277734 A1 11/2012 Goetz et al.
2012/0290082 A1 11/2012 Quint et al.
2013/0018456 A1 1/2013 Li et al.
2013/0018458 A1 1/2013 Yohanan et al.
2013/0023985 A1 1/2013 Khairkhahan et al.
2013/0046373 A1 2/2013 Cartledge et al.
2013/0079700 A1 3/2013 Ballard et al.
2013/0110229 A1 5/2013 Bokeriya et al.
2013/0116655 A1 5/2013 Bacino et al.
2013/0131780 A1 5/2013 Armstrong et al.
2013/0150956 A1 6/2013 Yohanan et al.
2013/0158647 A1 6/2013 Norris et al.
2013/0166017 A1 6/2013 Cartledge et al.
2013/0183515 A1 7/2013 White
2013/0184807 A1 7/2013 Kovach et al.
2013/0190857 A1 7/2013 Mitra et al.
2013/0197624 A1 8/2013 Armstrong et al.
2013/0204360 A1 8/2013 Gainor
2013/0253466 A1 9/2013 Campbell et al.
2013/0274873 A1 10/2013 Delaloye et al.
2013/0297003 A1 11/2013 Pinchuk
2013/0331929 A1 12/2013 Mitra et al.
2013/0338755 A1 12/2013 Goetz et al.
2014/0005771 A1 1/2014 Braido et al.
2014/0031924 A1 1/2014 Bruchman et al.
2014/0031927 A1 1/2014 Bruchman et al.
2014/0094898 A1 4/2014 Borck
2014/0106951 A1 4/2014 Brandon
2014/0135897 A1 5/2014 Cully et al.
2014/0135908 A1 5/2014 Glozman et al.
2014/0163671 A1 6/2014 Bruchman et al.
2014/0163673 A1 6/2014 Bruchman et al.
2014/0172066 A1 6/2014 Goepfrich et al.
2014/0172069 A1 6/2014 Roeder et al.
2014/0172077 A1 6/2014 Bruchman et al.
2014/0172078 A1 6/2014 Bruchman et al.
2014/0172079 A1 6/2014 Bruchman et al.
2014/0172082 A1 6/2014 Bruchman et al.
2014/0172083 A1 6/2014 Bruchman et al.
2014/0180400 A1 6/2014 Bruchman et al.
2014/0180402 A1 6/2014 Bruchman et al.
2014/0194968 A1 7/2014 Zukowski
2014/0194981 A1 7/2014 Menk et al.
2014/0200661 A1 7/2014 Pintor et al.
2014/0209238 A1 7/2014 Bonyuet et al.
2014/0222136 A1 8/2014 Geist et al.
2014/0277413 A1 9/2014 Richter et al.
2014/0277417 A1 9/2014 Schraut et al.
2014/0277418 A1 9/2014 Miller
2014/0277419 A1 9/2014 Garde et al.
2014/0277424 A1 9/2014 Oslund
2014/0277563 A1 9/2014 White
2014/0296962 A1 10/2014 Cartledge et al.
2014/0296969 A1 10/2014 Tegels et al.
2014/0324164 A1 10/2014 Gross et al.
2014/0330368 A1 11/2014 Gloss et al.
2014/0330372 A1 11/2014 Weston et al.
2014/0343670 A1 11/2014 Bakis et al.
2014/0350667 A1 11/2014 Braido et al.
2015/0005870 A1 1/2015 Kovach et al.
2015/0018944 A1 1/2015 O'Connell et al.
2015/0073545 A1 3/2015 Braido
2015/0088250 A1 3/2015 Zeng et al.
2015/0135506 A1 5/2015 White
2015/0142100 A1* 5/2015 Morriss ................ A61F 2/2445 623/2.4
2015/0157455 A1 6/2015 Hoang et al.
2015/0157456 A1 6/2015 Armstrong
2015/0157770 A1 6/2015 Cully et al.
2015/0224231 A1 8/2015 Bruchman et al.
2015/0245910 A1 9/2015 Righini et al.
2015/0313871 A1 11/2015 Li et al.
2015/0366664 A1 12/2015 Guttenberg et al.
2016/0001469 A1 1/2016 Bacchereti et al.
2016/0015422 A1 1/2016 De et al.
2016/0074161 A1 3/2016 Bennett
2016/0113699 A1 4/2016 Sverdlik et al.
2016/0175095 A1 6/2016 Dienno et al.
2016/0206424 A1 7/2016 Al-Jilaihawi et al.
2016/0213465 A1 7/2016 Girard et al.
2016/0235525 A1 8/2016 Rothstein et al.
2016/0250051 A1 9/2016 Lim et al.
2016/0310268 A1 10/2016 Oba et al.
2017/0014229 A1 1/2017 Nguyen-Thien-Nhon et al.
2017/0027727 A1 2/2017 Wuebbeling et al.

(56) References Cited

U.S. PATENT DOCUMENTS

2017/0056169 A1 3/2017 Johnson et al.
2017/0095330 A1 4/2017 Malewicz et al.
2017/0100236 A1 4/2017 Robertson et al.
2017/0105854 A1 4/2017 Treacy et al.
2017/0106176 A1 4/2017 Taft et al.
2017/0128199 A1 5/2017 Gurovich et al.
2017/0128209 A1 5/2017 Morriss et al.
2017/0156859 A1 6/2017 Chang et al.
2017/0165066 A1 6/2017 Rothstein
2017/0252153 A1 9/2017 Chau et al.
2017/0348101 A1 12/2017 Vaughn et al.
2018/0021129 A1 1/2018 Peterson et al.
2018/0028310 A1 2/2018 Gurovich et al.
2018/0153689 A1 6/2018 Maimon et al.
2018/0177583 A1 6/2018 Cully et al.
2018/0271653 A1 9/2018 Vidlund et al.
2018/0325665 A1 11/2018 Gurovich et al.
2018/0344456 A1 12/2018 Barash et al.
2019/0076245 A1 3/2019 Arcaro et al.
2019/0091014 A1 3/2019 Arcaro et al.
2019/0091015 A1 3/2019 Dienno et al.
2019/0110893 A1 4/2019 Haarer et al.
2019/0125517 A1 5/2019 Cully et al.
2019/0125528 A1 5/2019 Busalacchi et al.
2019/0125530 A1 5/2019 Arcaro et al.
2019/0125531 A1 5/2019 Bennett et al.
2019/0125534 A1 5/2019 Arcaro et al.
2019/0209739 A1 7/2019 Goepfrich et al.
2019/0216592 A1 7/2019 Cully et al.
2019/0328525 A1 10/2019 Noe et al.
2020/0022828 A1 1/2020 Armstrong et al.
2020/0179663 A1 6/2020 McDaniel et al.
2020/0276014 A1 9/2020 Burkart et al.
2022/0183831 A1 6/2022 Burkart et al.
2022/0273426 A1 9/2022 Hagaman et al.

FOREIGN PATENT DOCUMENTS

CN 101091675 A 12/2007
CN 101374477 A 2/2009
CN 101420913 A 4/2009
CN 101474102 A 7/2009
CN 101902989 A 12/2010
CN 101926699 A 12/2010
CN 201744060 U 2/2011
CN 102015009 A 4/2011
CN 102119013 A 7/2011
CN 102573703 A 7/2012
CN 102652694 A 9/2012
CN 102764169 A 11/2012
CN 102883684 A 1/2013
CN 103079498 A 5/2013
CN 103781439 A 5/2014
CN 105007955 A 10/2015
CN 105662651 A 6/2016
CN 105792780 A 7/2016
CN 106794065 A 5/2017
CN 107690323 A 2/2018
CN 108578016 A 9/2018
DE 144167 C 9/1903
DE 2246526 C3 7/1981
DE 19532846 A1 3/1997
DE 19857887 A1 7/2000
DE 19907646 A1 8/2000
DE 10049812 A1 4/2002
DE 10049813 C1 4/2002
DE 10049814 A1 4/2002
DE 10049815 A1 4/2002
DE 19546692 C2 11/2002
DE 212013000104 U1 11/2014
EP 0084395 A1 7/1983
EP 0103546 B1 5/1988
EP 0293090 A2 11/1988
EP 0313263 A2 4/1989
EP 0582870 A2 2/1994
EP 0775472 A2 5/1997
EP 0815806 A2 1/1998
EP 0850607 A1 7/1998
EP 0893108 A2 1/1999
EP 1057460 A1 12/2000
EP 1088529 B1 6/2005
EP 1666003 A1 6/2006
EP 1570809 B1 1/2009
EP 2193762 A1 6/2010
EP 2400923 A1 1/2012
FR 2591100 A1 6/1987
FR 2788217 A1 7/2000
FR 2815844 B1 1/2003
GB 2513194 A 10/2014
JP 44032400 B 12/1969
JP H09241412 A 9/1997
JP H11290448 A 10/1999
JP H11512635 A 11/1999
JP 2001508641 A 7/2001
JP 2007526098 A 9/2007
SU 1271508 A1 11/1986
WO WO-1991017720 A1 11/1991
WO WO-1992017118 A1 10/1992
WO WO-1993001768 A1 2/1993
WO WO-1994013224 A1 6/1994
WO WO-1995005555 A1 2/1995
WO WO-1995009586 A1 4/1995
WO WO-1996002212 A1 2/1996
WO WO-1996007370 A1 3/1996
WO WO-1996040348 A1 12/1996
WO WO-1997010871 A1 3/1997
WO WO-1997024080 A1 7/1997
WO WO-1999026558 A1 6/1999
WO WO-1999030646 A1 6/1999
WO WO-1999033414 A1 7/1999
WO WO-1999040964 A1 8/1999
WO WO-1999047075 A1 9/1999
WO WO-2000018333 A1 4/2000
WO WO-2000041649 A1 7/2000
WO WO-2000041652 A1 7/2000
WO WO-2000047139 A1 8/2000
WO WO-2000047271 A1 8/2000
WO WO-2000062716 A1 10/2000
WO WO-2001028453 A2 4/2001
WO WO-2001035878 A2 5/2001
WO WO-2001041679 A1 6/2001
WO WO-2001049213 A2 7/2001
WO WO-2001054624 A1 8/2001
WO WO-2001054625 A1 8/2001
WO WO-2001062189 A1 8/2001
WO WO-2001064137 A1 9/2001
WO WO-2001064278 A1 9/2001
WO WO-2001074272 A2 10/2001
WO WO-2001076510 A2 10/2001
WO WO-2002007795 A2 1/2002
WO WO-2002022054 A1 3/2002
WO WO-2002024118 A1 3/2002
WO WO-2002024119 A1 3/2002
WO WO-2002036048 A1 5/2002
WO WO-2002041789 A2 5/2002
WO WO-2002043620 A1 6/2002
WO WO-2002045933 A2 6/2002
WO WO-2002047468 A1 6/2002
WO WO-2002047575 A2 6/2002
WO WO-2002049540 A2 6/2002
WO WO-2002060506 A1 8/2002
WO WO-2002100301 A1 12/2002
WO WO-2003003946 A1 1/2003
WO WO-2003007795 A2 1/2003
WO WO-2003047468 A1 6/2003
WO WO-2003090834 A2 11/2003
WO WO-2004000375 A1 12/2003
WO WO-2005055883 A1 6/2005
WO WO-2005102015 A2 11/2005
WO WO-2006014233 A2 2/2006
WO WO-2006032051 A2 3/2006
WO WO-2006034008 A2 3/2006
WO WO-2006058322 A2 6/2006
WO WO-2006111391 A1 10/2006

(56) References Cited

FOREIGN PATENT DOCUMENTS

| | | | | |
|---|---|---|---|---|
| WO | WO-2006127089 A1 | | 11/2006 | |
| WO | WO-2006138173 A2 | | 12/2006 | |
| WO | WO-2007016251 A2 | | 2/2007 | |
| WO | WO-2007047488 A2 | | 4/2007 | |
| WO | WO-2007067942 A1 | | 6/2007 | |
| WO | WO-2008005405 A2 | | 1/2008 | |
| WO | WO-2008015257 A2 | | 2/2008 | |
| WO | WO-2008021002 A1 | | 2/2008 | |
| WO | WO-2008021006 A2 | | 2/2008 | |
| WO | WO-2008028964 A2 | | 3/2008 | |
| WO | WO-2008036870 A2 | | 3/2008 | |
| WO | WO-2008052421 A1 | | 5/2008 | |
| WO | WO-2008091515 A2 | | 7/2008 | |
| WO | WO-2008091589 A1 | | 7/2008 | |
| WO | WO-2008097589 A1 | | 8/2008 | |
| WO | WO-2008097592 A2 | | 8/2008 | |
| WO | WO-2008150529 A1 | | 12/2008 | |
| WO | WO-2009029199 A1 | | 3/2009 | |
| WO | WO-2009033469 A1 | | 3/2009 | |
| WO | WO-2009042196 A2 | | 4/2009 | |
| WO | WO-2009045332 A2 | | 4/2009 | |
| WO | WO-2009053497 A1 | | 4/2009 | |
| WO | WO-2009061389 A2 | | 5/2009 | |
| WO | WO-2009094188 A2 | | 7/2009 | |
| WO | WO-2009094501 A1 | | 7/2009 | |
| WO | WO-2009100210 A1 | | 8/2009 | |
| WO | WO-2009108355 A1 | | 9/2009 | |
| WO | WO-2009141286 A1 | * | 11/2009 | ........... A61F 2/2412 |
| WO | WO-2009149462 A2 | | 12/2009 | |
| WO | WO-2010006783 A1 | | 1/2010 | |
| WO | WO-2010008570 A1 | | 1/2010 | |
| WO | WO-2010011699 A2 | | 1/2010 | |
| WO | WO-2010030766 A1 | | 3/2010 | |
| WO | WO-2010057262 A1 | | 5/2010 | |
| WO | WO-2010086460 A1 | | 8/2010 | |
| WO | WO-2010121076 A2 | | 10/2010 | |
| WO | WO-2010132707 A1 | | 11/2010 | |
| WO | WO-2010150208 A2 | | 12/2010 | |
| WO | WO-2011098565 A1 | | 8/2011 | |
| WO | WO-2011109450 A2 | | 9/2011 | |
| WO | WO-2012004460 A2 | | 1/2012 | |
| WO | WO-2012011261 A1 | | 1/2012 | |
| WO | WO-2012040643 A2 | | 3/2012 | |
| WO | WO-2012048035 A2 | | 4/2012 | |
| WO | WO-2012065080 A2 | | 5/2012 | |
| WO | WO-2012082952 A2 | | 6/2012 | |
| WO | WO-2012099979 A1 | | 7/2012 | |
| WO | WO-2012110767 A2 | | 8/2012 | |
| WO | WO-2012116368 A2 | | 8/2012 | |
| WO | WO-2012158944 A1 | | 11/2012 | |
| WO | WO-2012167131 A1 | | 12/2012 | |
| WO | WO-2013074990 A1 | | 5/2013 | |
| WO | WO-2013096854 A2 | | 6/2013 | |
| WO | WO-2013106585 A1 | | 7/2013 | |
| WO | WO-2013109337 A1 | | 7/2013 | |
| WO | WO-2014099722 A1 | | 6/2014 | |
| WO | WO-2014144937 A2 | | 9/2014 | |
| WO | WO-2014149319 A1 | | 9/2014 | |
| WO | WO-2014210124 A1 | | 12/2014 | |
| WO | WO-2015045002 A1 | | 4/2015 | |
| WO | WO-2015171743 A2 | | 11/2015 | |
| WO | WO-2015173794 A1 | | 11/2015 | |
| WO | WO-2016028591 A1 | | 2/2016 | |
| WO | WO-2016100913 A1 | | 6/2016 | |
| WO | WO-2016186909 A1 | | 11/2016 | |
| WO | WO-2017038145 A1 | | 3/2017 | |
| WO | WO-2017096157 A1 | | 6/2017 | |
| WO | WO-2017218375 A1 | | 12/2017 | |
| WO | WO-2018029680 A1 | | 2/2018 | |
| WO | WO-2019074869 A1 | | 4/2019 | |
| WO | WO-2019246268 A1 | | 12/2019 | |

OTHER PUBLICATIONS

Andersen H.R., et al., "Transluminal Implantation of Artificial Heart Valves. Description of a New Expandable Aortic Valve and Initial Results with Implantation by Catheter Technique in Closed Chest Pigs," European Heart Journal, The European Society of Cardiology, Oxford University Press, United Kingdom, May 1, 1992, vol. 13, No. 5, pp. 704-708.

Andersen, H.R. "History of Percutaneous Aortic Valve Prosthesis," Herz No. 34. pp. 343-346. 2009.

Bailey S.R., "Percutaneous Expandable Prosthetic Valves," Textbook of Interventional Cardiology, 1994, vol. 2, 2nd Edition, pp. 1268-1276 (12 Pages).

Certified Priority Document for U.S. Appl. No. 61/739,721, Received by the International Bureau dated Jan. 3, 2014, 89 Pages.

Certified U.S. Appl. No. 13/843,196, filed Mar. 15, 2013, 52 Pages.

Clough N., et al., "Introducing a New Family of Gore (Trademark) ePTFE Fibers," 2007, pp. 1-10.

Cohn L.H., "Cardiac Surgery in the Adult," Third Edition, Chapter 2, 2008, 31 Pages.

Fontaine A.B., et al., "Prototype Stent: Invivo Swine Studies in the Biliary System1", Journal of Vascular and Interventional Radiology, Jan.-Feb. 1997, vol. 8, No. 1, pp. 101-105.

Fontaine A.B., et al., "Vascular Stent Prototype: Results of Preclinical Evaluation," Technical Developments and Instrumentation, Jan.-Feb. 1996, vol. 7, No. 1, pp. 29-34.

Nakayama Y., "Microporous Stent Achieves Brain Aneurysm Occlusion Without Disturbing Branching Flow," NeuroNews, Nov. 2012, No. 8, pp. 1-2.

Nishi S., et al., "Development of Microporous Self-expanding Stent Grafts for Treating Cerebral Aneurysms: Designing Micropores to Control Intimal Hyperplasia," Journal of Artificial Organs, 2011, vol. 14, pp. 348-356.

Notice of Opposition for European Application No. EP16196687.4, mailed Dec. 12, 2019, 38 Pages.

Notice of Opposition for European Application No. EP17187595.8, mailed Sep. 12, 2019, 50 Pages.

Patent Assignment Under Patent Reel 030473 and Frame 0861 for U.S. Appl. No. 13/843,196, Recorded on May 23, 2013, 4 Pages.

Patent Assignment Under Patent Reel 033502 and Frame 0073 for U.S. Appl. No. 14/133,563, Recorded on Aug. 9, 2014, 5 Pages.

Pavcnik D., et al., "Development and Initial Experimental Evaluation of a Prosthetic Aortic Valve for Transcatheter Placement," Cardiovascular Radiology, Apr. 1, 1992, vol. 183(1), pp. 151-154.

Ross, "Renal Ostial Stent System with Progressi-flex Technology," Evasc Medical Systems, Jun. 2009, 1 Page. (Applicant requests the Examiner to consider this reference to be prior art as of Jun. 2009).

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Serruys P.W., "Transcatheter Aortic Valve Implantation: Tips and Tricks to Avoid Failure," We File the Table of Contents and pp. 18 to 39 (Chapter 2) and pp. 102-114 (Chapter 8), the Publication Date According to the "Library of Congress Cataloging-in-Publication Data" is Nov. 24, 2009, 33 Pages.

"S-Shaped," Google Image Search Results, Accessed on Nov. 1, 2013, 1 Page.

Thubrikar M., "The Aortic Valve," Chapter 1: Geometry of the Aortic Valve, Informa Healthcare, CRC Press, Inc, 2011, 40 Pages.

Uchida et al., "Modifications of Gianturco Expandable Wire Stents", American Roentgen Ray Society, May 1988, pp. 1185-1187.

Walther T., etal, "Trans-catheter Valve-in-valve Implantation: In Vitro Hydrodynamic Performance of the SAPIEN + Cloth Trans-Catheter Heart Valve in the Carpentier-Edwards Perimount Valves," European Journal of Cardio-Thoracic Surgery, 2011, vol. 40, pp. 1120-1126, (Sep. 23, 2010).

Wheatley D. J., "Valve Prostheses," Operative Surgery, 4th edition, 1986, pp. 415-424.

Forward citations for E12 obtained from: https://scholar.google.com/scholar?cites=5981833429320176658&assdt=2005&sciodt=0,5&hl=en.

* cited by examiner 160
120
126b
126a
144
136a
136b
130

143
160
120
145
130
100
140

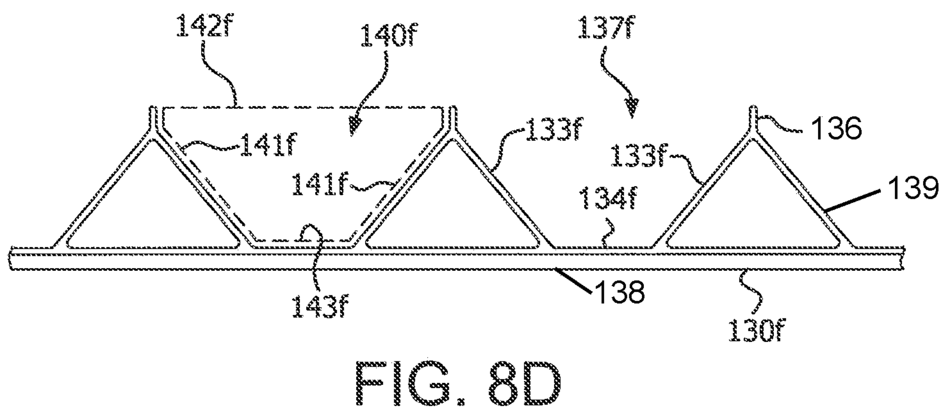
FIG. 8D
140g
142g
137g
141g
133g
133g
141g
134g
143g
138
130g
FIG. 8E
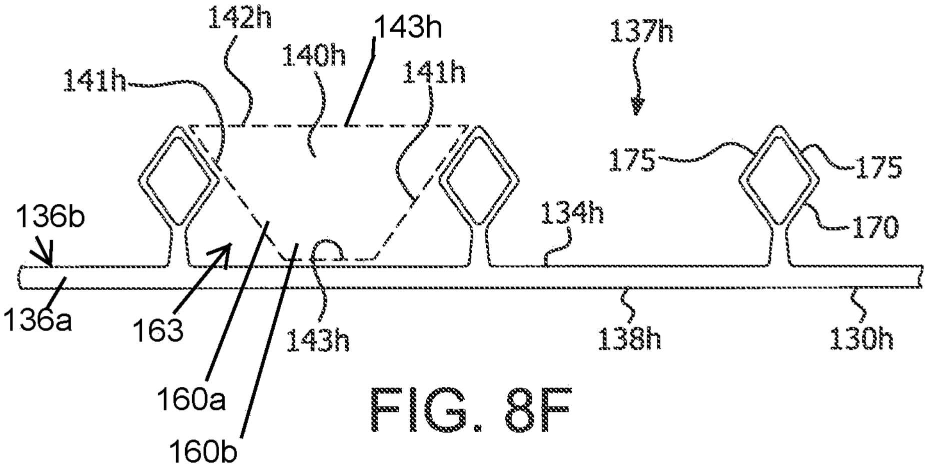
FIG. 8F

PROSTHETIC VALVES, FRAMES AND LEAFLETS AND METHODS THEREOF

CROSS-REFERENCE TO RELATED APPLICATIONS

This application is a continuation of U.S. patent application Ser. No. 17/140,366, filed Jan. 4, 2021, now U.S. Pat. No. 12,295,835, which is a continuation of U.S. patent application Ser. No. 15/662,571, filed Jul. 28, 2017, now U.S. Pat. No. 10,881,507, issued Jan. 5, 2021, which is a continuation of U.S. patent application Ser. No. 14/133,563, filed Dec. 18, 2013, now U.S. Pat. No. 9,737,398, issued Aug. 22, 2017, which claims the benefit of U.S. Provisional Application 61/802,116, filed Mar. 15, 2013, and also claims the benefit of U.S. Provisional Application 61/739,721, filed Dec. 19, 2012, all of which applications are incorporated herein by reference in their entireties for all purposes.

FIELD

The present disclosure relates generally to prosthetic heart valves and more specifically flexible leaflet-type (e.g., synthetic leaflet) prosthetic heart valve devices, systems, and methods.

BACKGROUND

Bioprosthetic heart valves have been developed that attempt to mimic the function and performance of a native valve. Flexible leaflets are fabricated from biological tissue such as bovine pericardium. In some bioprosthetic heart valve designs, the biological tissue is sewn onto a relatively rigid frame that supports the leaflets and provides dimensional stability when implanted. Although bioprosthetic heart valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic heart valve, herein referred to as a synthetic leaflet prosthetic heart valve (SLV). However, synthetic leaflet prosthetic heart valves have not become a valid heart valve replacement option since they suffer premature failure, due to, among other things, suboptimal design and lack of a durable synthetic material.

The leaflet moves under the influence of fluid pressure. In operation, the leaflets open when the upstream fluid pressure exceeds the downstream fluid pressure and close when the downstream fluid pressure exceeds the upstream fluid pressure. The leaflet free edges of the leaflets coapt under the influence of downstream fluid pressure closing the prosthetic heart valve to prevent downstream blood from flowing retrograde through the prosthetic heart valve.

Prosthetic heart valve durability under the repetitive loads of the leaflets opening and closing is dependent, in part, on the load distribution between the leaflet and the frame. Further, substantial load is encountered on the leaflet when in the closed position. Mechanical failure of the leaflet can arise, for example, at the mounting edge, where the flexible leaflet is supported by the relatively rigid frame. The repetitive loads of leaflet opening and closing leads to material failure by fatigue, creep or other mechanism, depending in part on the leaflet material. Mechanical failure at the mounting edge is especially prevalent with synthetic leaflets.

The durability of the valve leaflets is also a function of the character of bending by the leaflet during the opening-closing cycle. Small radius bends, creases and intersecting creases, can produce high stress zones in the leaflet. These high stress zones can cause the formation of holes and tears under repetitive loading.

Prosthetic heart valves may be delivered using surgical or transcatheter techniques. A surgical prosthetic heart valve is implanted into a patient using open-heart surgical techniques. The surgical prosthetic heart valve is usually manufactured to have a fixed diameter as opposed to a transcatheter prosthetic heart valve which is required to attain a range of diameters for access and delivery. The surgical prosthetic heart valve is usually provided with a sewing cuff about a perimeter of the prosthetic heart valve to allow for suturing to the native tissue orifice.

In addition to the prosthetic heart valve durability issues discussed above, the transcatheter prosthetic heart valve must also be able to withstand the handling and deployment stresses associated with being compressed and expanded.

A preferred shape of synthetic prosthetic heart valve leaflets has been described many times, but each is different from the others. The various three-dimensional shapes range from spherical or cylindrical to truncated conical intersections with spheres and an “alpharabola”.

The shape most often described as preferable is modeled after the native human aortic valve. Though nature dictates the optimum shape for the native tissues to form a heart valve, we have discovered this is not true for synthetic materials; accordingly, the design specified in the current disclosure is instead intended to place the synthetic material under a minimized stress condition as compared to those based on copies of the native valve. This is partially accomplished through reduced buckling in the leaflet material.

SUMMARY

In accordance with an embodiment, a prosthetic valve comprises a leaflet frame having a generally tubular shape, an outer frame having a generally tubular shape, and a film. The term film as used herein generically refers to one or more of a membrane, composite material, or laminate. The coaxially disposed at least partially within the outer frame. The leaflet frame and outer frame are coupled at least in part by a contiguous portion of the film. The leaflet frame defines a plurality of leaflet windows, wherein the film defines a leaflet extending from each of the leaflet windows.

In accordance with another embodiment, a prosthetic valve comprises a leaflet frame having a generally tubular shape and an outer frame having a generally tubular shape. The leaflet frame and outer frame are coupled together by a contiguous portion of a film in which the leaflet frame is nested into the outer frame in a telescoping manner. The leaflet frame defines a plurality of leaflet windows, wherein the film defines a leaflet extending from each of the leaflet windows.

In accordance with an embodiment, a prosthetic valve comprises a leaflet frame having a generally tubular shape, an outer frame having a generally tubular shape, and film. The leaflet frame is coaxially disposed at least partially within the outer frame. The outer frame provides frame elements that overlay leaflet windows that are defined by the leaflet frame so as to provide structural support over the leaflet windows, as shown in FIGS. 1A-1B. The leaflet frame defines a plurality of leaflet windows, wherein the film defines a leaflet extending from each of the leaflet windows.

In accordance with an embodiment, a prosthetic valve comprises a leaflet frame having a generally tubular shape, an outer frame having a generally tubular shape, and film. The leaflet frame defines a plurality of leaflet windows. The film defines at least one leaflet extending from each of the leaflet windows. Each leaflet has substantially the shape of an isosceles trapezoid having two leaflet sides, a leaflet base and a free edge opposite the leaflet base. The two leaflet sides diverge from the leaflet base, wherein the leaflet base is substantially flat.

In accordance with other embodiments of the prosthetic valve, each leaflet includes a central region and two side regions on opposite sides of the central region. The central region is defined by a shape substantially that of an isosceles trapezoid defined by two central region sides, the leaflet base and the leaflet free edge. The two central region sides converge from the leaflet base. Each of the side regions has a shape substantially that of a triangle and each are defined by one of the central region sides, one of the leaflet sides, and the leaflet free edge.

In accordance with other embodiments of the prosthetic valve, each leaflet includes a central region and two side regions on opposite sides of the central region. The central region is defined by a shape substantially that of an isosceles triangle defined by two central region sides, the leaflet base and the leaflet free edge. The two central region sides converge from the leaflet base to the free edge. Each of the side regions has a shape substantially that of a triangle and each are defined by one of the central region sides, one of the leaflet sides, and the leaflet free edge. Each of the two side regions and the central region are substantially planar when the valve is in the closed position and under no pressure load.

In accordance with other embodiments of the prosthetic valve, the frame comprises a frame first end and a frame second end opposite the frame first end, the leaflet window having a shape determined, at least in part, by wrapping a two dimensional isosceles trapezoid onto the tubular shape of the frame, the isosceles trapezoid having a base and two sides that diverge from the base, and wherein a side from adjacent isosceles trapezoids meet at the frame second end.

In accordance with other embodiments of the prosthetic valve, the leaflets defining a shape of a trapezoid wherein frame elements bounds two sides, one side being a free edge, and the leaflet base being is a horizontal truncation bound only by the film.

In accordance with other embodiments of the prosthetic valve, the film defining at least one leaflet is coupled to an outer surface of the leaflet frame.

In accordance with other embodiments of the prosthetic valve, the film defining at least one leaflet is coupled to an inner surface of the leaflet frame.

In accordance with other embodiments of the prosthetic valve, the leaflet frame and outer frame are coupled at least in part by a contiguous portion of the film.

In accordance with other embodiments of the prosthetic valve, the outer frame provides frame elements that overlay leaflet windows that are defined by the leaflet frame so as to provide structural support over the leaflet windows.

In accordance with other embodiments of the prosthetic valve, the outer frame provides frame elements that overlay the leaflet windows that are defined by the leaflet frame, wherein the leaflet frame and outer frame present a substantially uniform geometric pattern of frame elements that act in concert so as to enable the frame assembly to compress and expand substantially uniformly when compressed and expanded for transcatheter applications.

In accordance with other embodiments of the prosthetic valve, the film is disposed between the leaflet frame and the outer frame.

In accordance with other embodiments of the prosthetic valve, the leaflet frame and outer frame are separated by the film and are not in contact with each other.

In accordance with other embodiments of the prosthetic valve, each leaflet has a substantially flat leaflet base.

In accordance with other embodiments of the prosthetic valve, the leaflet frame defines three interconnected leaflet windows having a substantially triangular shape.

In accordance with other embodiments the prosthetic valve comprises a leaflet frame having a generally tubular shape, an outer frame having a generally tubular shape, and a film. The leaflet frame is coaxially disposed at least partially within the outer frame. The leaflet frame and outer frame are coupled at least in part by a contiguous portion of the film.

In accordance with other embodiments of the prosthetic valve, the leaflet frame defines a plurality of leaflet windows, and the film defines a leaflet extending from each of the leaflet windows.

In accordance with other embodiments of the prosthetic valve, a leaflet window side of one leaflet window is interconnected with a leaflet window side of an adjacent leaflet window.

In accordance with other embodiments of the prosthetic valve, each leaflet has substantially the shape of an isosceles trapezoid having two leaflet sides, a leaflet base and a free edge opposite the leaflet base, wherein the two leaflet sides diverge from the leaflet base, wherein the leaflet base is substantially flat.

In accordance with other embodiments of the prosthetic valve, the leaflet window is defined by window frame elements corresponding to the leaflet sides and leaflet base, wherein the film is coupled to the window frame elements and extends across the leaflet window defining the leaflet.

In accordance with other embodiments of the prosthetic valve, the film extends across the leaflet window defining a bending region and a support region separated by a bending interface, wherein the leaflet bends within the bending region when cycled between an open and closed position, wherein the bending interface defines the leaflet base and sides having substantially the shape of an isosceles trapezoid.

In accordance with other embodiments of the prosthetic valve, the bending interface is collocated with the leaflet window sides.

In accordance with other embodiments of the prosthetic valve, the bending interface is collocated with the leaflet window sides and leaflet window base.

In accordance with other embodiments of the prosthetic valve, the bending interface is spaced apart from and not collocated with the leaflet window base.

In accordance with other embodiments of the prosthetic valve, the bending interface is spaced apart from and not collocated with the leaflet window sides and leaflet window base.

In accordance with other embodiments of the prosthetic valve, the bending interface is collocated with a portion of the leaflet window sides.

In accordance with other embodiments of the prosthetic valve, the bending interface defines the leaflet base and sides having the shape of an isosceles trapezoid.

In accordance with other embodiments of the prosthetic valve, the frame comprises a plurality of spaced apart leaflet windows each defining substantially an isosceles triangle interconnected by a base element, wherein each leaflet window side is defined by a side of one triangle and a side of an adjacent triangle, and wherein each leaflet window base is defined by the base element.

In accordance with other embodiments of the prosthetic valve, the frame comprises a base element and a plurality of spaced apart spade elements interconnected by the base element, wherein each leaflet window is defined by a side of one spade element and a side of an adjacent spade element, and wherein each leaflet window base is defined by the base element.

In accordance with other embodiments of the prosthetic valve, the frame comprises a plurality of spaced apart interconnected leaflet windows each defining substantially isosceles triangles, wherein each leaflet window side is defined by a side of one triangle and a side of an adjacent triangle, and wherein each leaflet window base is defined by the base element.

In accordance with other embodiments of the prosthetic valve, the prosthetic valve comprises a collapsed configuration and an expanded configuration for transcatheter delivery.

In accordance with other embodiments of the prosthetic valve, the leaflet is moveable between an open and closed position.

In accordance with other embodiments of the prosthetic valve, the leaflet comprises a polymeric film.

In accordance with other embodiments of the prosthetic valve, the leaflet comprises a laminate.

In accordance with other embodiments of the prosthetic valve, wherein the laminate has more than one layer of a fluoropolymer membrane.

In accordance with other embodiments of the prosthetic valve, the leaflet comprises a film having at least one fluoropolymer membrane layer having a plurality of pores and an elastomer present in substantially all of the pores of at least one layer of fluoropolymer membrane.

In accordance with other embodiments of the prosthetic valve, the film comprises less than about 80% fluoropolymer membrane by weight.

In accordance with other embodiments of the prosthetic valve, the elastomer comprises (per) fluoroalkylvinylethers (PAVE).

In accordance with other embodiments of the prosthetic valve, the elastomer comprises a copolymer of tetrafluoroethylene and perfluoromethyl vinyl ether.

In accordance with other embodiments of the prosthetic valve, the fluoropolymer membrane comprises ePTFE.

In accordance with other embodiments of the prosthetic valve, the leaflet frame and/or outer frame defines a generally open pattern of apertures operable to allow the outer frame to be compressed and expanded between different diameters.

In accordance with other embodiments of the prosthetic valve, an aspect ratio of a length of the valve to a diameter of the valve is less than 1.

In accordance with other embodiments of the prosthetic valve, the valve is less than about 20 mm in length.

In accordance with other embodiments of the prosthetic valve, the leaflet frame and/or outer frame comprise a shape memory film.

In accordance with other embodiments of the prosthetic valve, the leaflet frame and/or outer frame comprises a metallic film.

In accordance with other embodiments of the prosthetic valve, in a collapsed configuration has a collapsed profile less than about 6 mm.

In accordance with other embodiments of the prosthetic valve, the valve is balloon expandable.

In accordance with other embodiments of the prosthetic valve, the film sandwiches the outer frame and the leaflet frame.

In accordance with an embodiment, a prosthetic valve comprises a plurality of leaflets, each leaflet having a shape substantially that of an isosceles trapezoid having two leaflet sides, a leaflet base, and a free edge opposite the leaflet base, wherein the two leaflet sides diverge from the leaflet base.

In accordance with another embodiment, a prosthetic valve comprises a plurality of leaflets, wherein, wherein each leaflet includes a central region and two side regions on opposite sides of the central region, wherein the central region is defined by a shape substantially that of an isosceles triangle defined by two central region sides, the leaflet base and the leaflet free edge, wherein the two central region sides converge from the leaflet base, and wherein each of the side regions have a shape substantially that of a triangle and each are defined by one of the central region sides, one of the leaflet sides, and the leaflet free edge.

In accordance with an embodiment, a prosthetic valve comprises a leaflet frame, an outer frame, and a film. The leaflet frame has a generally tubular shape defining a plurality of leaflet windows. The outer frame has a generally tubular shape. The leaflet frame is coaxially disposed at least partially within the outer frame. The leaflet frame and outer frame are coupled at least in part by a contiguous portion of the film. At least a portion of the contiguous portion of the film is contained between and coupling the leaflet frame and outer frame operable to prevent relative movement and contact therebetween. The film defines a leaflet extending from each of the leaflet windows.

In accordance with an embodiment, a prosthetic valve comprises and leaflet frame, and outer frame and a film. The leaflet frame has a generally tubular shape defining a plurality of leaflet windows. The outer frame has a generally tubular shape. The leaflet frame is coaxially disposed at least partially within the outer frame. The outer frame includes frame elements that overlay the leaflet windows that are defined by the leaflet frame in cooperative arrangement so as to provide structural support over the leaflet windows. The film defines a leaflet extending from each of the leaflet windows.

In accordance with an embodiment, a method of making a prosthetic valve, comprises: wrapping a first layer of film into a tubular farm about a mandrel;

providing a leaflet frame having a generally tubular shape, the leaflet frame having a leaflet frame leaflet surface and a leaflet frame outer surface, the leaflet frame defining a plurality of leaflet windows having a window top; providing an outer frame having a generally tubular shape, the outer frame having an outer frame leaflet surface and an outer frame outer surface; placing the leaflet frame and the outer frame over the first layer of film with the leaflet frame and outer frame spaced apart from each other defining a bridge portion therebetween, the leaflet frame inner surface and the outer frame inner surface in contact with the first layer of film;

forming a second layer of film over the leaflet frame and the outer frame in contact with the leaflet frame outer surface and the outer frame outer surface; coupling the first layer of film and the second layer of film to each other and to the leaflet frame and the outer frame; cutting the first layer of film and the second layer of film across the window top within the leaflet window so as to define a leaflet free edge; masking with release material a portion of the film disposed in the leaflet window that defines the leaflet to prevent further bonding of the leaflet during subsequent processing steps; wrapping a third layer of film into a tubular form over the second layer of film and over the release material that is over the leaflet window, overlapping the leaflet frame, the outer frame, and over the bridge portion between the leaflet frame and outer frame; coupling the third layer of film and the second layer of film to each other;

removing the assembly from the mandrel; disposing coaxially and at least partially the leaflet frame into the outer frame, folding and overlapping at least partially the bridge portion so as to contain the bridge portion between the leaflet frame and the outer frame; placing the assembly back on the mandrel; coupling the bridge portion to itself and to the third layer of film adjacent the leaflet frame outer surface and the first layer adjacent the outer frame inner surface in nesting engagement.

Described embodiments are directed to an apparatus, system, and methods for valve replacement, such as cardiac valve replacement. More specifically, described embodiments are directed toward flexible leaflet valve devices in which the leaflets are divided into zones, each with a particular geometry.

In accordance with an embodiment, a prosthetic valve comprises a plurality of leaflets, each leaflet defining two side regions and a central region between the side regions, the central region having a shape that is different from that of the side regions.

In accordance with an embodiment, a prosthetic valve comprises a leaflet frame and a film. The leaflet frame has a generally tubular shape. The leaflet frame defines a plurality of leaflet windows wherein each of the leaflet windows includes two leaflet window sides, a leaflet window base, and a leaflet window top. The film being coupled to the leaflet frame and defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, and wherein the leaflet base is substantially flat. The leaflet base is coupled to the window base and each of the two leaflet sides are coupled to one of the two window sides.

In accordance with an embodiment, a prosthetic valve comprises a plurality of leaflets. Each leaflet includes a central region and two side regions on opposite sides of the central region. The central region is defined by a shape substantially that of an isosceles triangle defined by two central region sides, the leaflet base and the leaflet free edge, wherein the two central region sides converge from the leaflet base, and wherein each of the side regions have a shape substantially that of a triangle and each are defined by one of the central region sides, one of the leaflet sides, and the leaflet free edge.

In accordance with an embodiment, a method of forming a prosthetic heart valve comprises providing a leaflet frame having a generally tubular shape, the leaflet frame defining a plurality of leaflet windows wherein each of the leaflet windows includes two leaflet window sides, a leaflet window base, and a leaflet window top; providing a film, and wrapping the film about the leaflet frame bringing more than one layer of the film into contact with additional layers of the film defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, wherein the leaflet base is substantially flat; wherein the leaflet base is coupled to the window base and wherein each of the two leaflet sides are coupled to one of the two window sides providing a generally annular support structure; and bonding the layers of film to itself and to the leaflet frame.

In accordance with an embodiment, a method of forming a prosthetic heart valve comprises providing a leaflet frame having a generally tubular shape, the leaflet frame defining a plurality of leaflet windows wherein each of the leaflet windows includes two leaflet window sides, a leaflet window base, and a leaflet window top; providing a film; wrapping the film about the leaflet frame bringing more than one layer of the film into contact with additional layers of the film defining at least one leaflet extending from each of the leaflet windows, wherein each leaflet has substantially the shape of an isosceles trapezoid having two leaflet sides, a leaflet base and a free edge opposite the leaflet base, wherein the two leaflet sides diverge from the leaflet base, wherein the leaflet base is substantially flat; wherein the leaflet base is coupled to the window base and wherein each of the two leaflet sides are coupled to one of the two window sides providing a generally annular support structure; and bonding the layers of film to itself and to the leaflet frame.

Described embodiments are directed to an apparatus, system, and methods for valve replacement, such as cardiac valve replacement. More specifically, described embodiments are directed toward flexible leaflet valve devices in which a truncated segment at the base of the leaflet is present at or adjacent to the intersection with the frame.

In accordance with an embodiment, a prosthetic valve comprises a leaflet frame, a plurality of leaflets that are coupled to the leaflet frame, where each leaflet has a free edge and a base. The base of each leaflet is truncated in which the leaflet in cross section shows a line in an alpha plane onto the leaflet frame.

In accordance with an embodiment, a prosthetic valve comprises a frame having a generally tubular shape with attached film. The frame defines a plurality of leaflet windows. The film defines at least one leaflet extending from each of the leaflet windows. Each leaflet two leaflet sides, a planar central zone, a leaflet base and a free edge opposite the leaflet base. The two leaflet sides diverge from the leaflet base.

In accordance with an embodiment, a prosthetic valve comprises a leaflet frame, a plurality of leaflets that are coupled to the leaflet frame, where each leaflet has a free edge and a base. Each leaflet has a planar zone in a central portion, wherein the planar zone is substantially planar. The planar zone defines a shape having an area, wherein the area is larger nearer the base than the free edge.

In accordance with an embodiment, a prosthetic heart valve comprises a leaflet frame having a generally tubular shape with attached film. The leaflet frame defines a plurality of leaflet windows. The film defines at least one leaflet extending from each of the leaflet windows. Each leaflet attachment zone on the leaflet frame has substantially the shape of an isosceles trapezoid having two leaflet sides, a leaflet base and a leaflet free edge opposite the leaflet base. The two leaflet sides diverge from the leaflet base, wherein the leaflet base is substantially flat.

In accordance with other embodiments of the prosthetic heart valve, each leaflet attachment zone on the leaflet frame includes a central region and two side regions on opposite sides of the central region. The central region of the attachment zone on the leaflet frame is defined by a shape substantially that of an isosceles trapezoid defined by two central region sides, the leaflet base and the leaflet free edge. The two central region sides of the attachment zone on the leaflet frame converge from the leaflet base. Each of the side regions of the attachment zone on the leaflet frame has a shape substantially that of a triangle and each are defined by one of the central region sides, one of the leaflet sides, and the leaflet free edge.

In accordance with other embodiments of the prosthetic heart valve, each leaflet attachment zone on the leaflet frame includes a central region and two side regions on opposite sides of the central region. The central region of the attachment zone on the leaflet frame is defined by a shape substantially that of an isosceles triangle defined by two central region sides, the leaflet base and the leaflet free edge. The two central region sides converge from the leaflet base to the leaflet free edge. Each of the side regions of the attachment zone on the leaflet frame has a shape substantially that of a triangle and each are defined by one of the central region sides, one of the leaflet sides, and the leaflet free edge In accordance with other embodiments of the prosthetic heart valve, the leaflet frame comprises a leaflet frame first end and a leaflet frame second end opposite the leaflet frame first end, the leaflet window having a shape determined, at least in part, by wrapping a two dimensional isosceles trapezoid pattern onto the tubular shape of the leaflet frame, the isosceles trapezoid pattern having a base and two sides that diverge from the base, and wherein a side from adjacent isosceles trapezoids meet at the leaflet frame second end.

In accordance with other embodiments of the prosthetic heart valve, the leaflets defining a shape of a trapezoid wherein frame elements bounds two sides, one side being a leaflet free edge, and the leaflet base being is a horizontal truncation bound only by the film.

In accordance with an embodiment, a prosthetic heart valve comprises a plurality of leaflets, each leaflet attachment zone on the leaflet frame having a shape substantially that of an isosceles trapezoid having two leaflet sides of the attachment zone on the leaflet frame, a leaflet base, and a leaflet free edge opposite the leaflet base, wherein the two leaflet sides diverge from the leaflet base.

In accordance with another embodiment, a prosthetic heart valve comprises a plurality of leaflets, wherein, wherein each leaflet attachment zone on the leaflet frame includes a central region and two side regions on opposite sides of the central region, wherein the central region is defined by a shape substantially that of an isosceles triangle defined by two central region sides, the leaflet base and the leaflet free edge, wherein the two central region sides converge from the leaflet base, and wherein each of the side regions of the attachment zone on the leaflet frame have a shape substantially that of a triangle and each are defined by one of the central region sides, one of the leaflet sides, and the leaflet free edge.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 8D is an embodiment of a leaflet frame unrolled to a flat orientation;

FIG. 8E is an embodiment of a leaflet frame unrolled to a flat orientation;

FIG. 8F is an embodiment of a leaflet frame unrolled to a flat orientation;

DETAILED DESCRIPTION

Figure 1A:
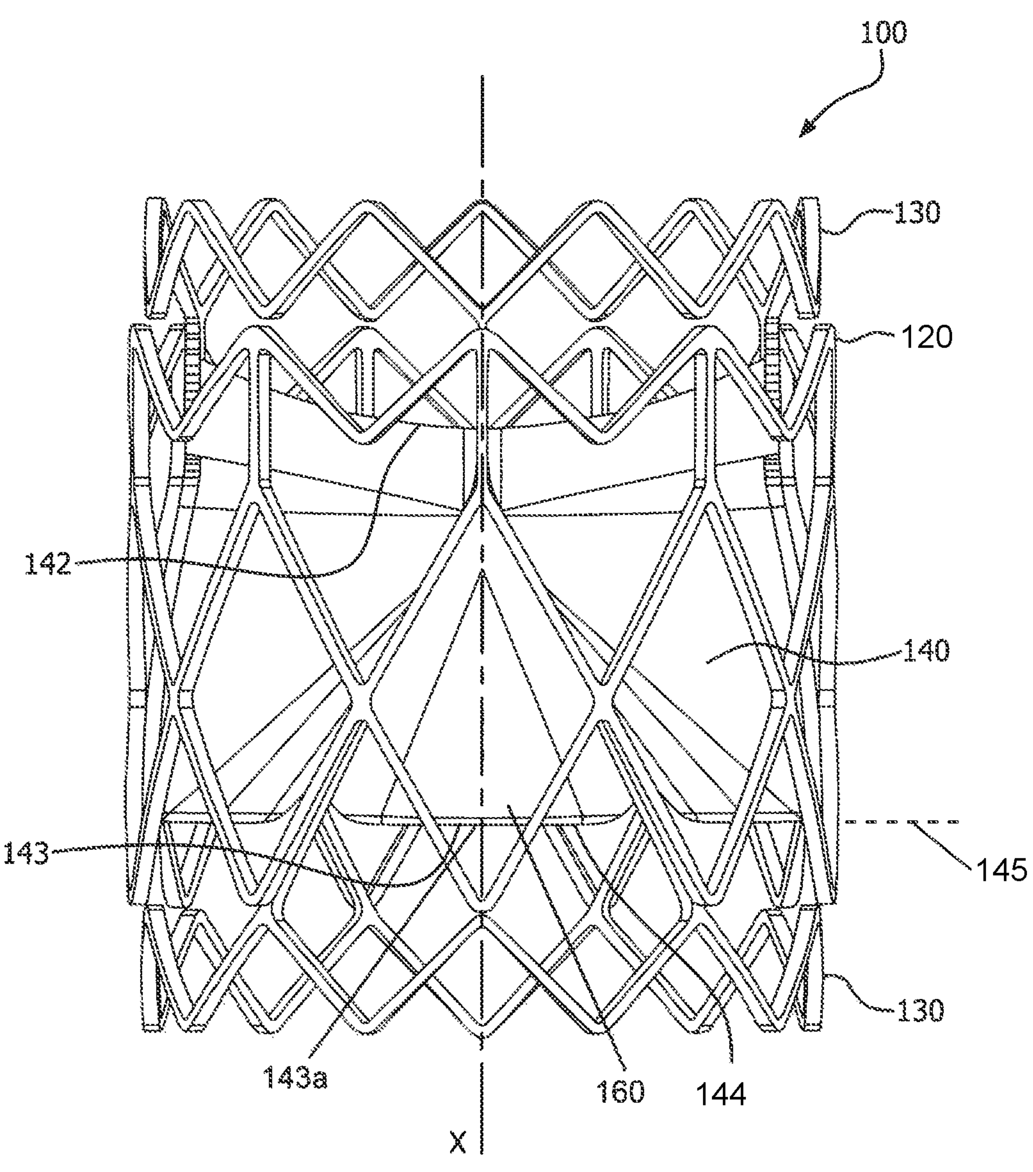
FIG. 1A is a side view of an embodiment of a prosthetic heart valve.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic heart valves, more specifically cardiac prosthetic heart valves. However, embodiments within the scope of this disclosure can be applied toward any heart valve or mechanism of similar structure and/or function. Furthermore, embodiments within the scope of this disclosure can be applied in non-cardiac applications.

The term leaflet as used herein in the context of prosthetic heart valves is a component of a one-way valve wherein the leaflet is operable to move between an open and closed position under the influence of a pressure differential. In an open position, the leaflet allows blood to flow through the prosthetic heart valve. In a closed position, the leaflet substantially blocks retrograde flow through the prosthetic heart valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inf low side of the prosthetic heart valve rises above the pressure on the outflow side of the prosthetic heart valve, the leaflets open and blood flows therethrough. As blood flows through the prosthetic heart valve into a neighboring chamber or blood vessel, the pressure on the inf low side equalizes with the pressure on the outflow side. As the pressure on the outflow side of the prosthetic heart valve rises above the blood pressure on the inflow side of the prosthetic heart valve, the leaflet returns to the closed position generally preventing retrograde flow of blood through the prosthetic heart valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term leaflet window is defined as that space that a leaflet frame defines from which a leaflet extends. The leaflet may extend from leaflet frame elements or adjacent to and spaced apart therefrom.

The term frame element as used herein refers to any portion of a leaflet frame or outer frame, such as, but not limited to, those individual portions that define a leaflet window or aperture.

The term attachment zone as used herein refers to the portion of the film that is attached to something so as to define the shape of the leaflet. The attachment zone may be, such as, but not limited to, that portion of the film that is coupled to the frame elements that define the leaflet window. The attachment zone may also be, such as, but not limited to, that portion of the film that is coupled to another film at a location that is not directly adjacent to a frame element.

The terms native heart valve orifice and tissue orifice refer to an anatomical structure into which a prosthetic heart valve may be placed. Such anatomical structure includes, but is not limited to, a location wherein a cardiac valve may or may not have been surgically removed. It is understood that other anatomical structures that may receive a prosthetic heart valve include, but are not limited to, veins, arteries, ducts and shunts. Although reference is made herein to replacing a native heart valve with a prosthetic heart valve, it is understood and appreciated that a valve orifice or implant site may also refer to a location in a synthetic or biological conduit that may receive a valve for a particular purpose, and therefore the scope of the embodiments provided herein is not limited to heart valve replacement.

As used herein, "couple" means to join, connect, attach, adhere, affix, or bond, whether directly or indirectly, and whether permanently or temporarily.

Figure 3A:
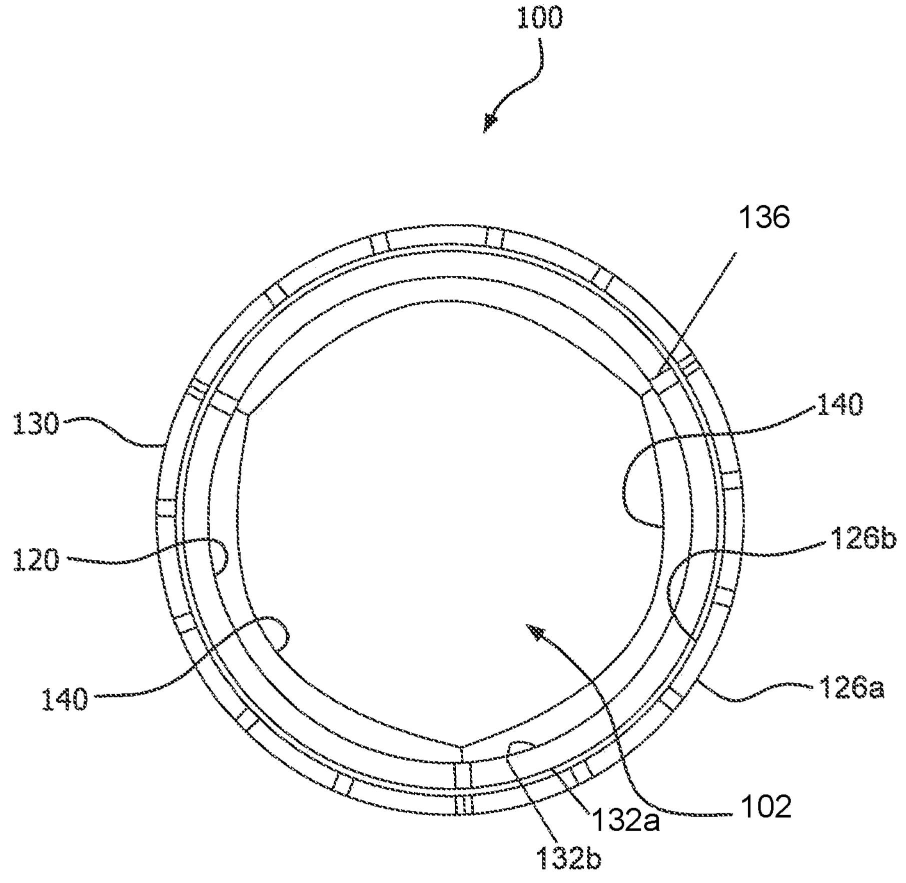
FIG. 3A is an axial or top view of the embodiment of the prosthetic heart valve of FIG. 1A in an open configuration.
Figure 3B:
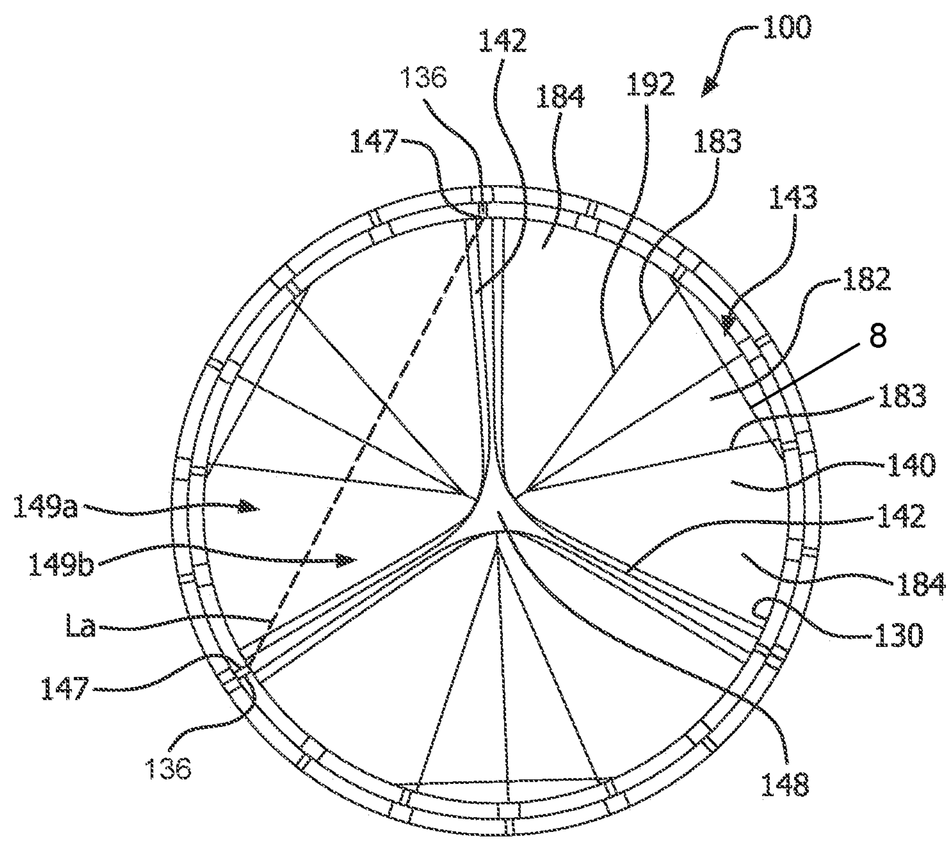
FIG. 3B is an axial or top view of the embodiment of the prosthetic heart valve of FIG. 1A in a closed configuration.

As used herein, truncated or truncation refers to the sectioning of a three-dimensional body with a plane reducing the size of the body. Referring to FIGS. 1A and 3B, a truncation zone is that area of the leaflet that may be truncated by a truncation plane intersecting the alpha plane so as to define an attachment line, i.e., a line of attachment, of the leaflet base.

Embodiments herein include various apparatus, systems, and methods for a prosthetic heart valve suitable for surgical and transcatheter placement, such as, but not limited to, cardiac valve replacement. The prosthetic heart valve is operable as a one-way valve wherein the prosthetic heart valve defines a valve orifice into which leaflets open to perm it flow and close so as to occlude the valve orifice and prevent flow in response to differential fluid pressure.

Embodiments provided herein are related to controlled leaflet opening. The durability of the prosthetic heart valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading.

Controlled bending is of particular importance in thin, high-modulus synthetic leaflets, since the bending in these materials tends to be cellophane-like. If the leaflet bending character is uncontrolled, not only do creases farm, but crease intersections lead to formation of large three dimensional structures that oppose bending and slow down the leaflet motion, both in opening and closing: in order to avoid this, the sequence of opening of the parts of the leaflet must be controlled.

Controlled bending is achieved through a particular frame shape, in accordance with embodiments. The frame shape dictates the leaflet attachment perimeter, which further dictates leaflet movement.

Embodiments provided herein present advancement in prosthetic heart valve technology related to, but not limited to, mechanic and biological performance advantages. In accordance with some embodiments presented herein, a prosthetic heart valve comprises two frames, a leaflet frame and an outer frame, that are coupled together by a contiguous film in which a leaflet frame is nested into an outer frame in a telescoping manner, wherein there is no chance for the prosthetic heart valve to leak between the leaflet frame and the outer frame.

In accordance with some embodiments presented herein, a prosthetic heart valve comprises two frames; a leaflet frame and an outer frame. The film that comprises the leaflet may be coupled to the inner surface of the leaflet frame. In some other embodiments, the film that comprises the leaflet is contained between the leaflet frame and the outer frame and extends through a leaflet window defined by the leaflet frame. The leaflet, therefore, is significantly prevented from peeling or delaminating as it is contained between the leaflet frame and outer frame, as compared to where the leaflets are only coupled to the inner surface of the leaflet frame.

In accordance with some embodiments presented herein, a prosthetic heart valve comprises two frames; a leaflet frame and an outer frame. The leaflet frame and the outer frame are separated from each other by a film. In other words, there is a metal to polymer to metal interconnection, wherein there is no metal to metal contact between the leaflet frame and the outer frame.

In accordance with some embodiments presented herein, a prosthetic heart valve comprises two frames; a leaflet frame and an outer frame. The leaflet frame is nested within the outer frame, wherein the leaflet frame and outer frame cooperate to provide relatively high resistance to flat plate compression, among other things. In accordance with some embodiments, the outer frame provides frame elements that overlay the leaflet windows that are defined by the leaflet frame so as to provide structural support over the leaflet windows. In accordance with some embodiments, the outer frame provides frame elements that overlay the leaflet windows that are defined by the leaflet frame so as to prevent tissue from extending into the leaflet windows when implanted. In accordance with some embodiments, the outer frame provides frame elements that overlay the leaflet windows that are defined by the leaflet frame and act in concert so as to allow the frame assembly to compress and expand uniformly for transcatheter embodiments.

In accordance with some embodiments presented herein, a prosthetic valve comprises two frames; a leaflet frame and an outer frame. The leaflet frame defines leaflet windows that define, in part, the shape of the leaflets. In some embodiments the leaflet comprises a flat base, wherein the leaflet bends from the base towards the leaflet free edge with minimal creasing and fluttering. In some embodiments the leaflet comprises a flat base, that, among other things, that provides for one or more of a shorter valve length, substantially prevents blood stagnation and pooling and encourages washing at the base, as compared to leaflets having a rounded base.

In accordance with some embodiments presented herein, a prosthetic valve comprises two frames; a leaflet frame and an outer frame. The leaflet frame defines leaflet windows from which the leaflets extend. The leaflets are defined by the intersection of films that form an overlapping zone so as to define, at least in part, the leaflet base and/or the leaflet sides.

The length of a leaflet heart valve is dictated by the angle the leaflet makes with respect to the enclosing frame. A longer leaflet has a shallower angle with respect to the frame. A shorter leaflet has a steeper angle with respect to the frame. A longer leaflet leads to better performance than a shorter leaflet. For most applications however, only a short valve can fit into the recipient location. Thus the valve designer is presented with a dilemma. In the instant embodiments, leaflet designs are provided that provide for good performance with a short leaflet, thus allowing short heart valves.

Embodiments provided herein place the synthetic materials under a minimized stress condition as compared to those based on copies of the native valve. This is partially accomplished through reduced buckling in the leaflet material.

Embodiments provided herein address controlled leaflet opening. The durability of the valve leaflets is largely controlled by the character of bending exhibited by the leaflet during the opening-closing cycle. Small radius bends, creases and particularly intersecting creases, can produce high stress zones in the leaflet. These high stress zones can cause the formation of holes and tears under repetitive loading. Embodiments provided herein provide a feature of leaflet shape so as to minimize crease formation, which is of particular importance in thin, high-modulus leaflets, since the bending in these materials tends to be cellophane-like. If the leaflet bending is unrestricted, not only do creases form, but crease intersections lead to formation of large three dimensional structures that oppose bending and slow down the leaflet motion, both in opening and closing. Embodiments provided herein control leaflet opening and provide minimization of crease formation provided by an inclusion of a planar zone in the leaflet.

Prosthetic Heart Valve

Figure 16A:
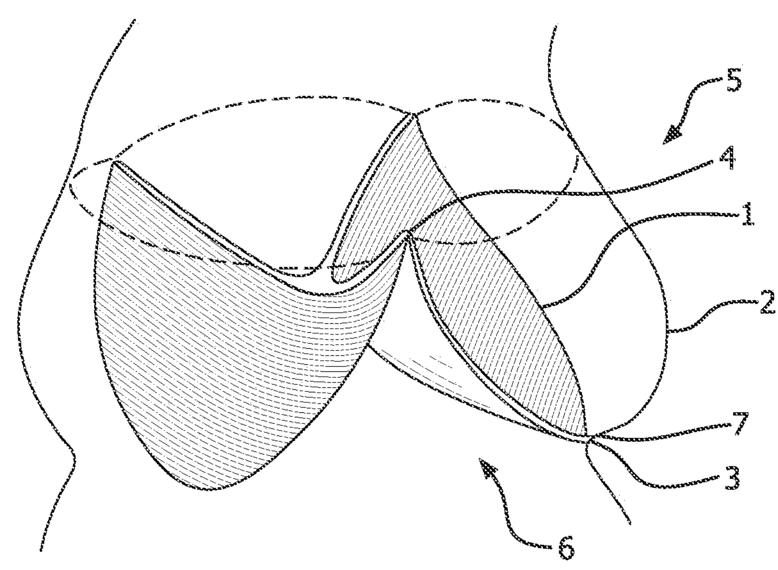
FIG. 16A is a representation of an aortic valve.
Figure 16B:
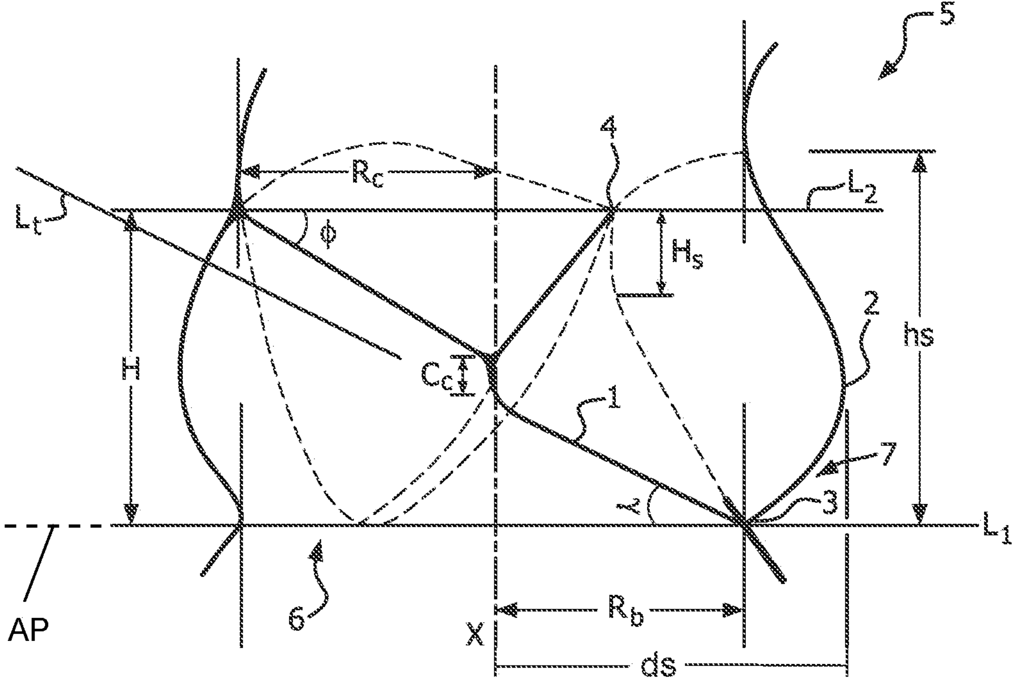
FIG. 16B is a cross-section of the aortic valve of FIG. 16A showing the angles associated with a leaflet heart valve.

FIG. 16A. is a sketch of an aortic valve 5. The leaflets 1 are coupled to the aortic root 2 at the leaflet base 3. FIG. 16B is a cross-section of the aortic valve 5 of FIG. 16A showing the angles associated with a leaflet 1 of the aortic valve 5. FIG. 16B illustrates the relationship between the leaflets 1 and a first horizontal line L1 extending through the leaflet base 3 at an attachment point 7, and a second horizontal line L2 extending through the tops 4 of the commissure. In FIG. 16B, the aortic valve 5 is oriented in a position with a valve axis X being vertical, the inflow edge 6 is pointed downward, with the leaflets 1 in the closed position. The attachment angle alpha ($\alpha$) is defined as the angle between the tangent line Lt extending from the center of the leaflet base 3 of the leaflet 1 at the attachment point 7 and the first horizontal line L1 extending through the leaflet base 3 at the attachment point 7, as shown in FIG. 16A.

Referring to FIG. 16B: Rb is the radius of the base, Rc is the radius of the commissures, H is the valve height, alpha is the bottom surface angle of the leaflet, phi is the free edge angle of the leaflet, Hs is the height of the commissures, and Cc is the coaptation height.

It is understood that leaflets 1 may exhibit a concave, straight, or convex shape in an axial cross-section through the center of the leaflet base 3 of the leaflet 1 at the attachment point 7. For the sake of clarity and simplification of description of the embodiments presented herein and not limited thereto, the geometry of a leaflet 1 is described as having, in an axial cross-section through the center of the leaflet base 3 of the leaflet 1 at the attachment point 7, the tangent line Lt that defines a as a straight line.

Embodiments provided herein provide a solution to the tension between desiring a small alpha angle to have a short valve and a larger alpha angle resulting in longer leaflets for better leaflet bending behavior. Embodiments provided herein provide a larger alpha angle while reducing valve length, by providing a leaflet that wherein the leaflet base 3 is truncated, providing a relatively flat leaflet base 143.

In accordance with embodiments herein, the attachment angle alpha (α) of a given valve configuration is preserved as the leaflet height is reduced. This is accomplished by redefining the base of the leaflet not as an attachment point 3 as for the generally parabolic leaflet shape as shown in FIG. 1A, but as an attachment line 8 as shown in FIG. 3B, that is parallel to the horizontal line in the valve cross sectional plane perpendicular to the valve axis X at the leaflet base 143 of the leaflet 140.

As a way to visualize embodiments provided herein, referring to FIG. 16B, the first horizontal line L1 extends through the leaflet base 3*a* as it moves perpendicular along the valve axis X towards the commissure tops 4. A plane containing the first horizontal line L1 and perpendicular to the valve axis, referred to as the alpha plane, intersects the leaflet frame 140 of FIG. 1A along a line. Wherein the leaflet base 7 is truncated by the alpha plane, wherein the attachment point 3 of the leaflet base 7 becomes an attachment line 144, that is, a line of attachment rather than a point, of the leaflet base 143 as shown in FIGS. 1A and 3B.

Referring to FIG. 3B, an apex line La is indicated connecting the apices 147 of the leaflets 140. The apex line La divides the leaflet 140 into a first region 149*a* adjacent the leaflet frame 130, and a second region 149*b* adjacent the leaflet free edge. The first region 149*a* defines a truncated zone. The truncated zone is located on the lower section of the leaflet 140 adjacent the leaflet base 143. Referring to FIGS. 1A and 3B, the truncation zone is that area of the leaflet 140 that may be truncated by a truncation plane intersecting the alpha plane so as to define an attachment line 144, i.e., a line of attachment, of the leaflet base 143.

Figure 1B:
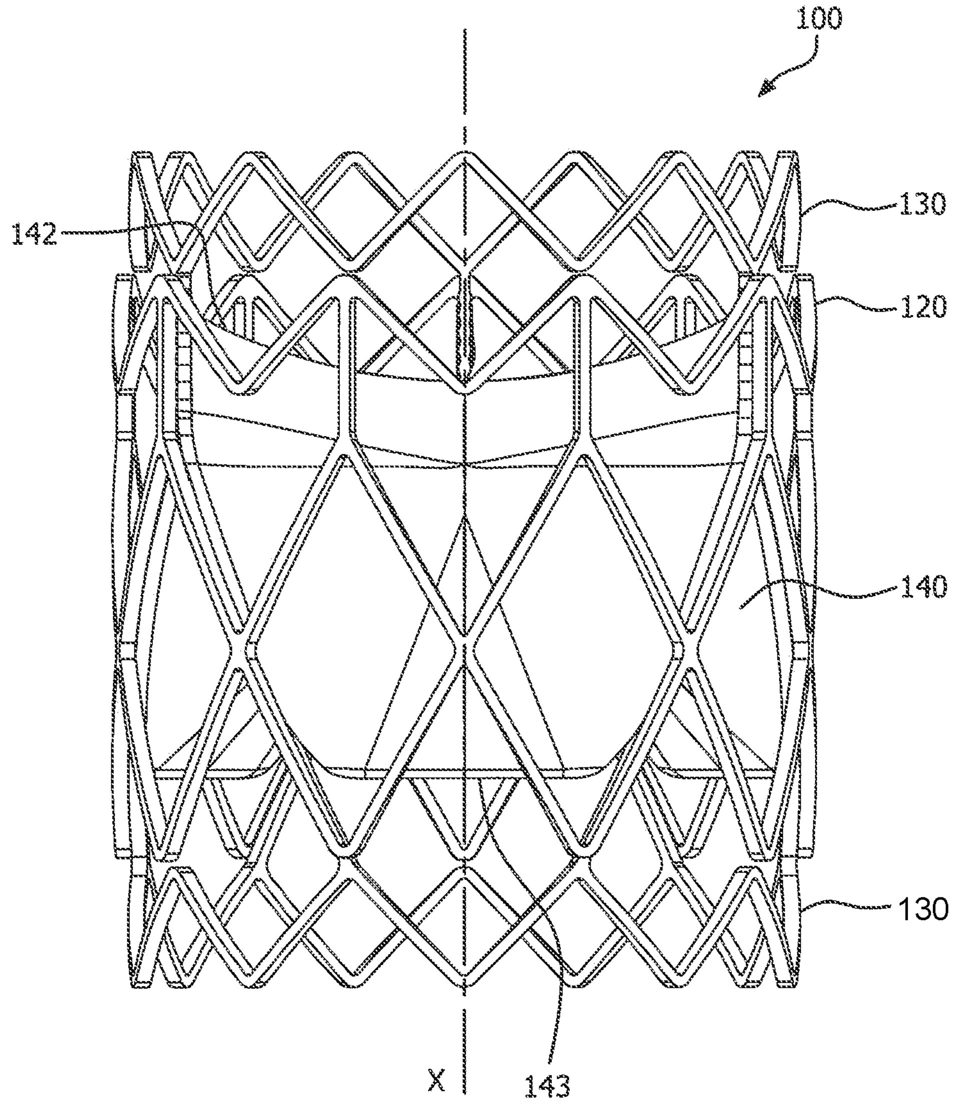
FIG. 1B is a side view of the embodiment of the prosthetic heart valve of FIG. 1A that is partially rotated about the axis X.
Figure 1C:
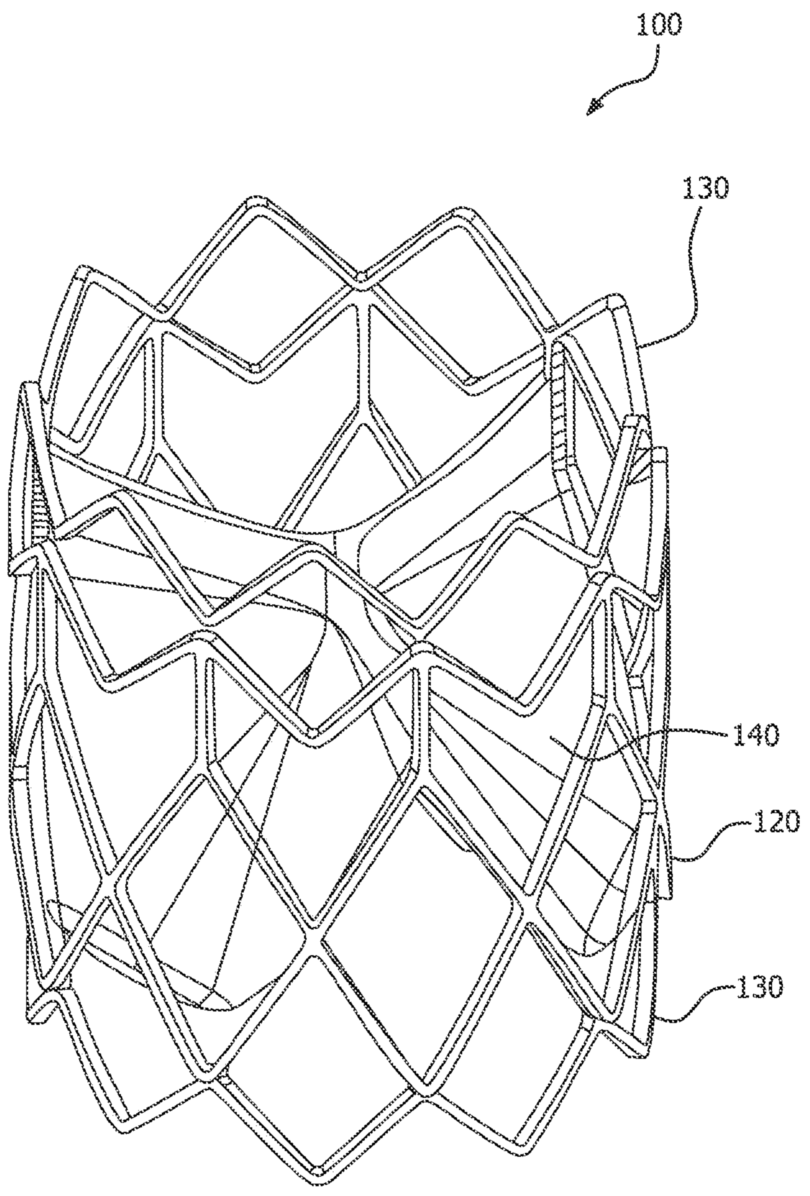
FIG. 1C is a perspective view of the embodiment of the prosthetic heart valve of FIG. 1A.
Figure 2A:
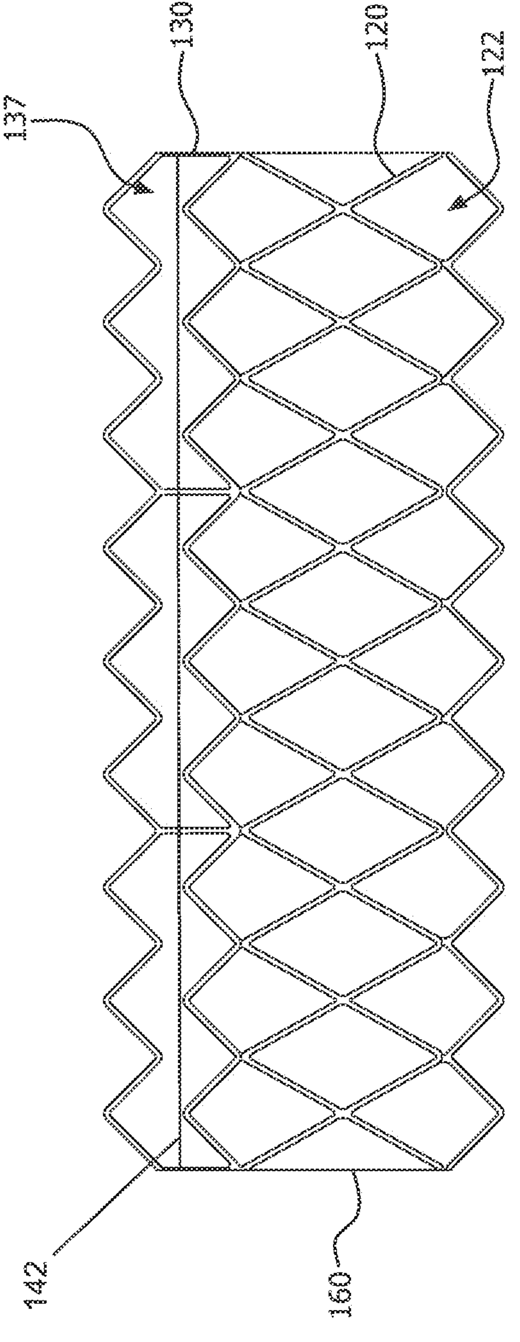
FIG. 2A is a representation of the embodiment of the prosthetic heart valve of FIG. 1A unrolled to a flat orientation.
Figure 2B:
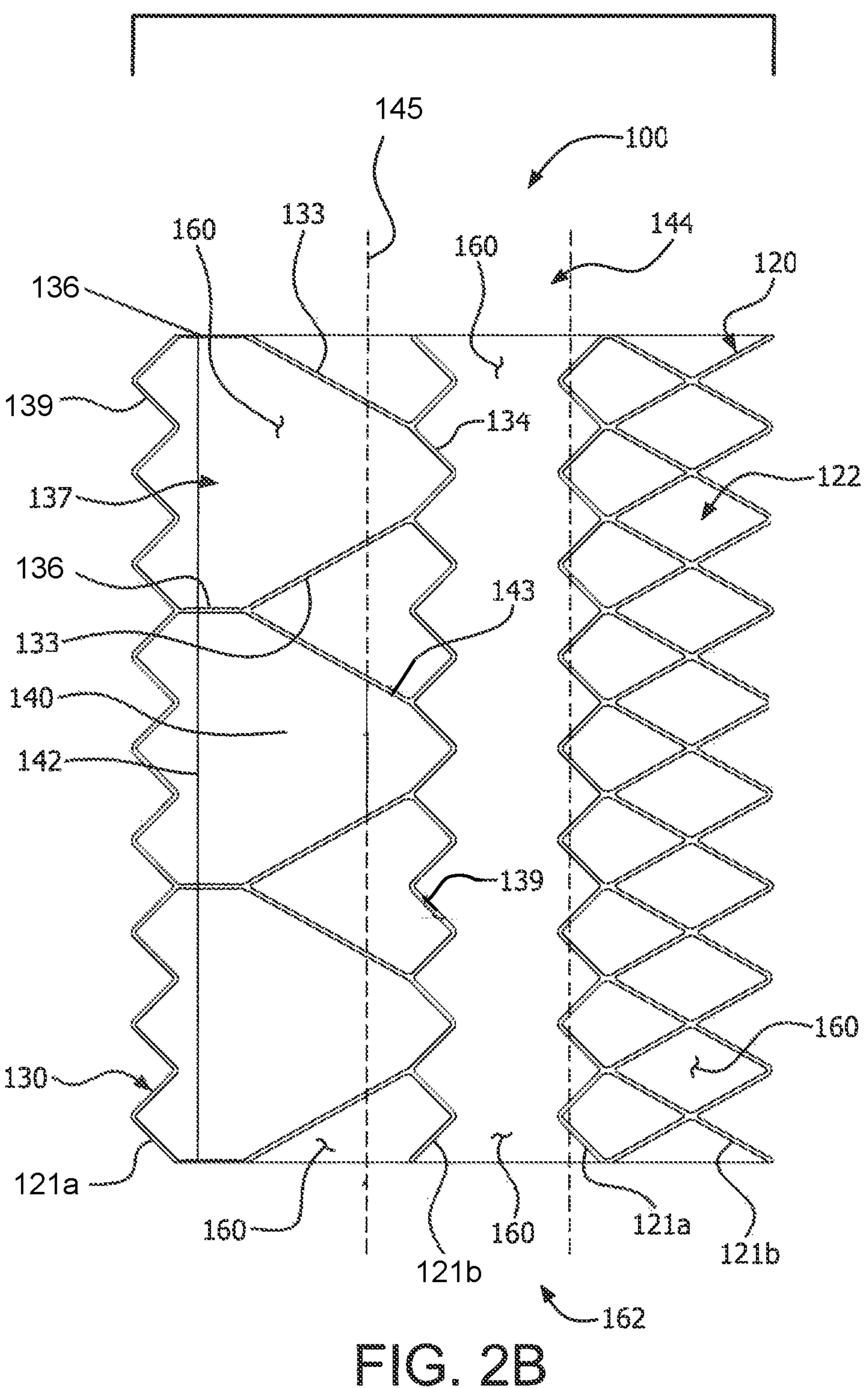
FIG. 2B is an exploded representation of the embodiment of the prosthetic heart valve of FIG. 1A unrolled to a flat orientation.

FIG. 1A is a side view of a prosthetic heart valve 100, in accordance with an embodiment. FIG. 1B is also a side view of the prosthetic heart valve 100 of FIG. 1A rotated 60 degrees about the longitudinal axis X. FIG. 1C is a perspective view of the prosthetic heart valve 100 of FIG. 1A. FIG. 2A is a side view of the prosthetic heart valve 100 of FIG. 1A wherein the prosthetic heart valve 100 has been longitudinally cut and laid open to better illustrate the elements of the generally tubular-shaped prosthetic heart valve 100. FIG. 2B is an exploded view of the embodiment of FIG. 2A. FIGS. 3A and 3B are axial views of the prosthetic heart valve 100 of FIG. 1A in an open and closed configuration, respectively. In FIG. 3B the leaflets 140 are shown slightly open to better show the features but it is understood that a fully closed prosthetic heart valve 100 will have the leaflet free edges 142 of the leaflets 140 coming together to coapt under the influence of downstream fluid pressure which results in closing the valve to prevent downstream blood from flowing retrograde through the valve.

The valve 100 comprises an outer frame 120, a leaflet frame 130, and a film 160 covering the outer frame 120 and leaflet frame 130, coupling the outer frame 120 to the leaflet frame 130, and defining leaflets 140. The embodiment of valve 100 is discussed further related to a transcatheter valve that may be compressed and re-expanded. It is understood that the embodiment of valve 100 is also applicable to a surgical valve by the addition of a sewing cuff 170 as shown in FIG. 4B. Leaflet frame and outer frame configurations related to surgical valve only embodiments where the valves have a fixed diameter, will be discussed in other embodiments later in this disclosure.

In accordance with an embodiment, a prosthetic valve comprises a leaflet frame 130 having a generally tubular shape, an outer frame 120 having a generally tubular shape, and film 160. The leaflet frame 130 is coaxially disposed at least partially within the outer frame 120. The outer frame 120 provides frame elements that overlay leaflet windows that are defined by the leaflet frame 130 so as to provide structural support over the leaflet windows, as shown in FIGS. 1A-1B. The leaflet frame 130 defines a plurality of leaflet windows, wherein the film 160 defines a leaflet extending from each of the leaflet windows.

11A is a side view of a prosthetic heart valve 200, in accordance with an embodiment. FIG. 11B is a perspective view of the prosthetic heart valve 200 of FIG. 1A. The prosthetic heart valve 200 comprises a leaflet frame 130*f* and film 160 that defines leaflets 140. In FIGS. 3B and 11D, the leaflets 140 are shown slightly open to better show the features but it is understood that a fully closed prosthetic heart valve 200 will have the leaflet free edges 142 of the leaflets 140 coming together to coapt under the influence of downstream fluid pressure which results in closing the valve to prevent downstream blood from flowing retrograde through the valve. The term "frame element" as used herein refers to any portion of the leaflet frame 130, such as, but not limited to, those individual portions that define a leaflet window 137. The leaflet frame first end 131*a* further comprises commissure posts 136 extending from an apex of the leaflet frame elements defining substantially a triangle.

Figure 11A:
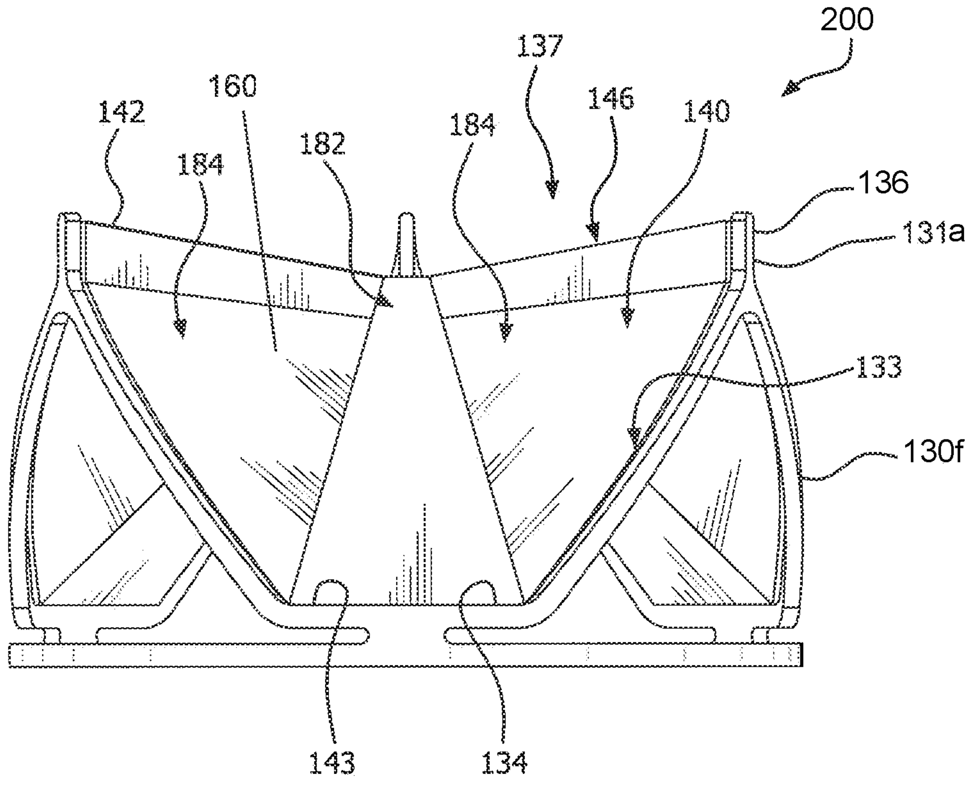
FIG. 11A is a side view of an embodiment of a prosthetic heart valve.
Figure 11B:
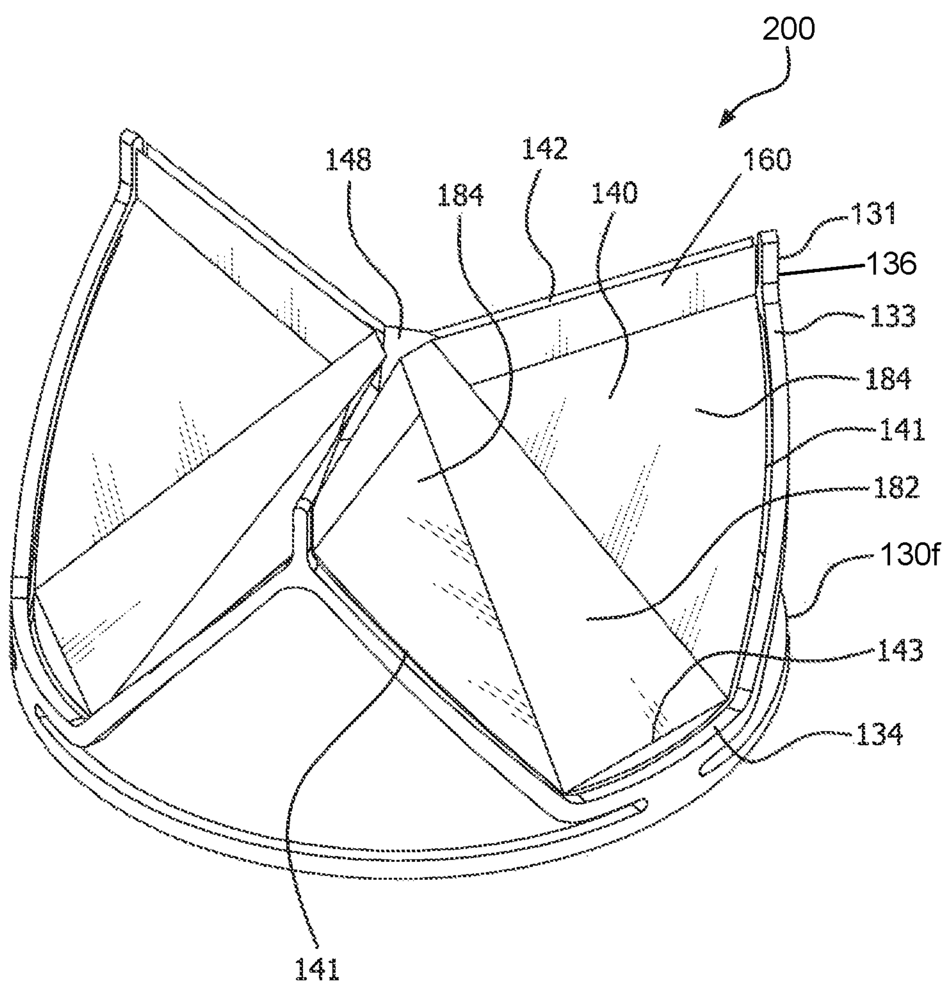
FIG. 11B is a perspective view of the embodiment of the prosthetic heart valve of FIG. 11A.

FIG. 8D is a side view of the leaflet frame 130*f* of the prosthetic heart valve 200 of FIGS. 11A and 11B wherein the leaflet frame 130*f* has been longitudinally cut and laid open to better illustrate the elements of the generally tubular-shaped prosthetic heart valve 200. The leaflet frame 130*f* comprises a plurality of spaced apart frame elements 139 defining substantially an isosceles triangles interconnected by a base element 138*f* defining leaflet windows 137*f* having the shape of and isosceles trapezoid. Each leaflet window side 133 is defined by a side of one triangle and a side of an adjacent triangle, and wherein each leaflet window base 134 is defined by the base element 138. The term "frame element" as used herein refers to any portion of the leaflet frame 130, such as, but not limited to, those individual portions that define a leaflet window 137.

Referring again to FIGS. 11A and 8D, the leaflet frame first end 131*a* further comprises commissure posts 136 extending from an apex of the leaflet frame elements defining substantially an isosceles triangle. The commissure post 136 may affect the leaflet free edge 142 so as to create a larger or wider coaptation region 146 between adjacent leaflet free edges 142.

Outer Frame

The outer frame 120 is a generally tubular member defining a generally open pattern of apertures 122, in accordance with an embodiment, as shown in FIG. 1C. The outer frame 120 is comprised of a generally cylindrical arrangement of three triangular-shaped leaflet windows 137, the centers of which are each spaced apart by 120°, as shown in FIG. 2B.

Figures 5A, 5B:
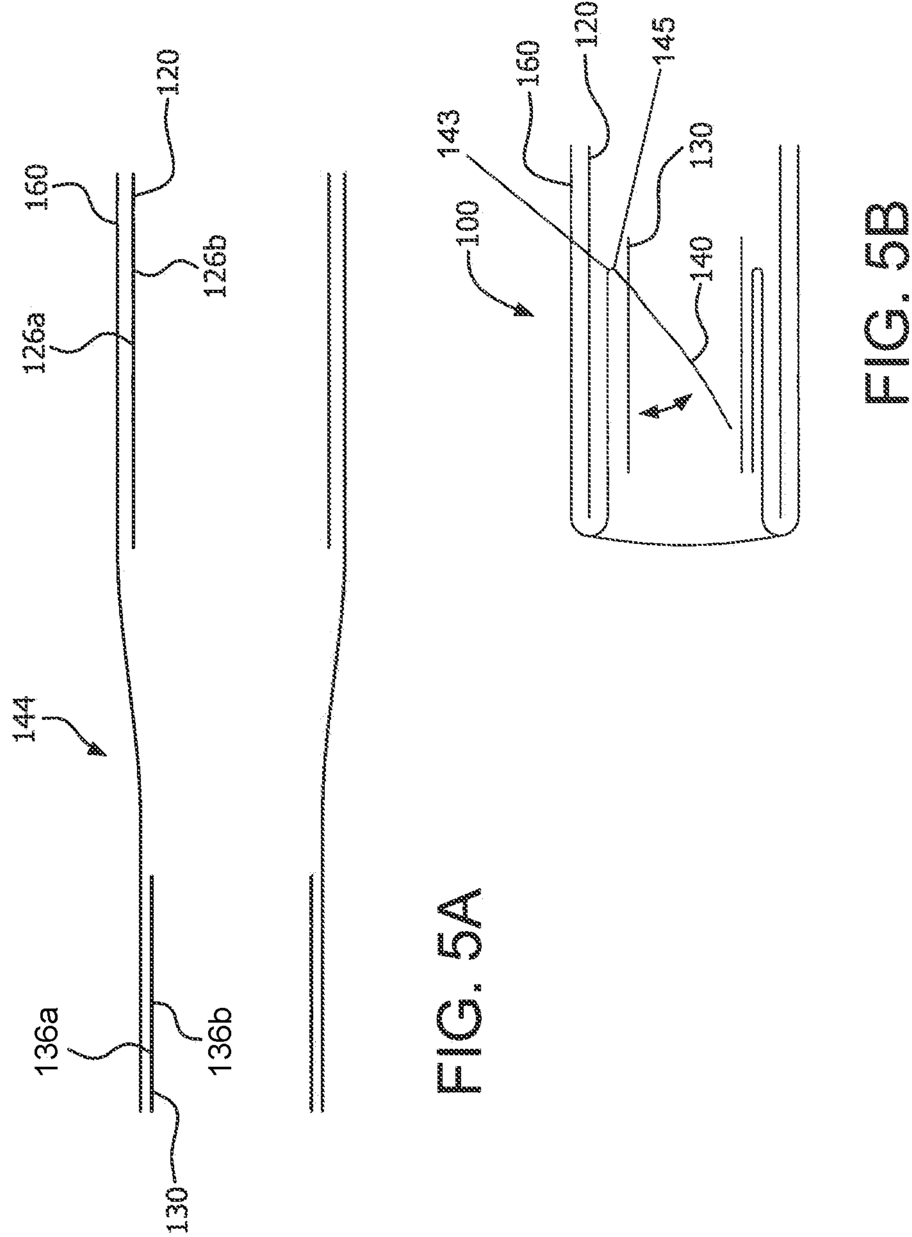
FIG. 5A is a cross-sectional view of an embodiment of the valve during manufacture.
FIG. 5B is a cross-sectional view of the leaflet frame and the outer frame as nested together, in accordance with the embodiment of FIG. 5A.

In accordance with transcatheter embodiments, the outer frame 120 is operable to allow it to be compressed and expanded between different diameters. The outer frame 120 comprises an outer frame outer surface 126*a* and an outer frame inner surface 126*b* opposite the outer frame outer surface 126*a*, as shown in FIG. 5A. The outer frame 120 may comprise a structure known in the art as a stent. A stent is a tubular member that may have a small diameter suitable for percutaneous transcatheter delivery into the anatomy, and may be expanded to a larger diameter when deployed into the anatomy. Stents having various designs and material properties are well known in the art.

Figure 1D:
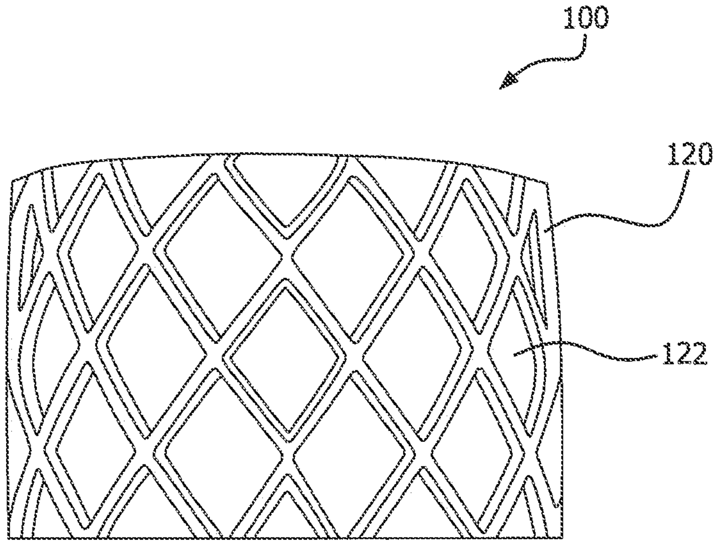
FIG. 1D is a representation of a prosthetic heart valve in an expanded configuration.

By way of example, and as illustrated in the embodiments of FIGS. 1A-1C and 2A-2B, the prosthetic heart valve 100 includes the outer frame 120 that defines a stent having apertures 122 having generally a diamond shape when in a large diameter configuration, as shown generally in FIG. 1D. Upon compression to a smaller diameter, the apertures 122 deform to generally define an elongated diam and shape, as shown generally in FIG. 1E. Upon re-expansion to a larger diameter, the apertures 122 re-expand to again define a generally diamond shape.

As shown in FIGS. 5A and 5B, both views showing the elements in cross-section, the leaflet frame 130 has a generally tubular shape defining a plurality of leaflet windows (not shown). The outer frame 120 has a generally tubular shape. The leaflet frame 130 is coaxially disposed at least partially within the outer frame 120. The leaflet frame 130 and outer frame 120 are coupled at least in part by a contiguous portion of the film 160. At least a portion of the contiguous portion of the film 160 is contained between and couples the leaflet frame 130 to the outer frame 120 to inhibit relative movement therebetween. The film defines a leaflet 140 extending from each of the leaflet windows. The leaflet base 143 is defined at a fold line 145 in the film 160. In accordance with an embodiment, at least a portion of the contiguous portion of the film 160 that is contained between and coupling the leaflet frame 130 and outer frame 120 prevents contact between the leaflet frame 130 and outer frame 120.

Figure 6A:
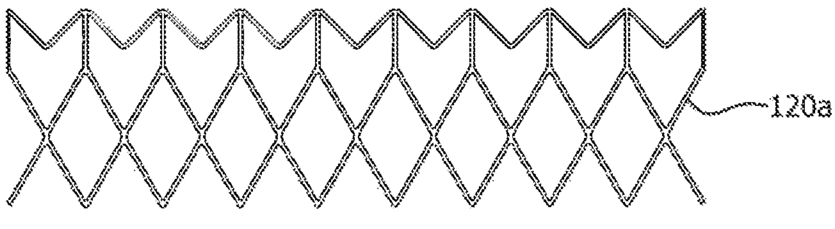
FIG. 6A is an embodiment of an outer frame unrolled to a flat orientation.
Figure 6B:
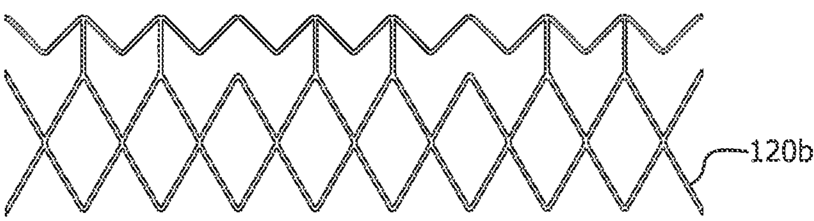
FIG. 6B is an embodiment of an outer frame unrolled to a flat orientation.

FIGS. 6A and 6B are side views of alternative embodiments of the outer frame 120*a*, 120*b* wherein the outer frame has been longitudinally cut and laid open to better illustrate the elements of the outer frame An open framework of the stent can define any number of features, repeatable or otherwise, such as geometric shapes and/or linear or meandering series of sinusoids. Geometric shapes can comprise any shape that facilitates substantially uniform circumferential compression and expansion. The outer frame 120 may comprise a cut tube, or any other element suitable for the particular purpose. The outer frame 120 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

It is known that stents of various designs may be elastically deformable so as to be self-expanding under spring loads. It is also known that stents of various designs may be plastically deformable so as to be mechanically expanded such as with a balloon. It is also known that stents of various designs may be plastically deformable as well as elastically deformable. The embodiments of the outer frame 120 presented herein are not to be limited to a specific stent design or mode of expansion.

The outer frame 120 can comprise any metallic or polymeric biocompatible material. For example, the outer frame 120 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Figure 4A:
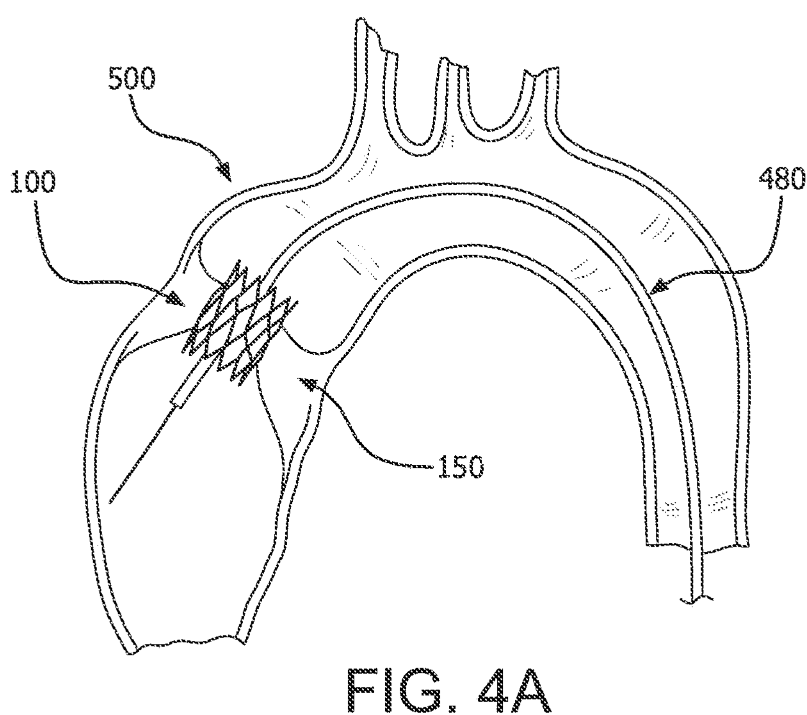
FIG. 4A is a side view of an embodiment of a transcatheter delivery system within anatomy.
Figure 4B:
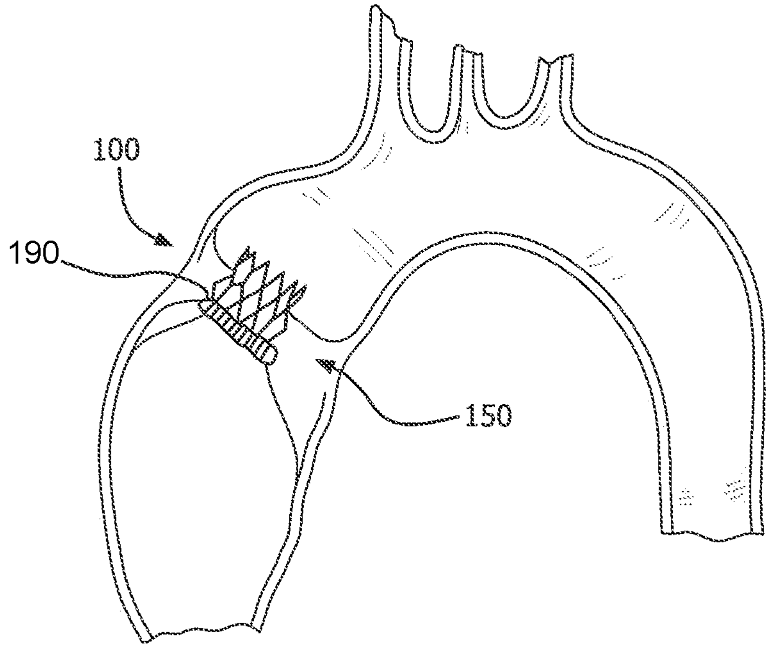
FIG. 4B is a side view of an embodiment of a surgical prosthetic heart valve within anatomy.

In accordance with embodiments, the outer frame 120 and/or leaflet frame 130 can be configured to provide positive engagement with an implant site to firmly anchor the prosthetic heart valve 100 to the site, as shown in FIG. 4A representing a transcatheter deployment of the prosthetic heart valve 100. In accordance with an embodiment, the outer frame 120 can comprise a sufficiently rigid frame having small elastic recoil so as to maintain sufficient apposition against a tissue orifice 150 to maintain position. In accordance with another embodiment, the outer frame 120 and/or leaflet frame 130 can be configured to expand to a diameter that is larger than a tissue orifice 150 so that when prosthetic heart valve 100 expands into the tissue orifice 150, it can be firmly seated therein. In accordance with another embodiment, the outer frame 120 can comprise one or more anchors (not shown) configured to engage the implant site, such as a tissue orifice 150, to secure the prosthetic heart valve 100 to the implant site.

It is appreciated that other elements or means for coupling the prosthetic heart valve 100 to an implant site are anticipated. By way of example, but not limited thereto, other means, such as mechanical and adhesive means may be used to couple the prosthetic heart valve 100 to a synthetic or biological conduit.

Sewing Cuff

In accordance with a surgical valve 100 embodiment, the valve 100 further comprises a sewing cuff 170 about a body frame outer surface 127 in accordance with an embodiment, as shown in FIG. 4B. The sewing cuff 170 is operable to provide structure that receives suture for coupling to the implant site. The sewing cuff 170 may comprise any suitable material, such as, but not limited to, double velour polyester. The sewing cuff 170 may be located circumferentially around a perimeter of the base frame 120. Sewing cuffs are known in the art.

Leaflet Frame

Referring again to FIGS. 1C and 2B, the leaflet frame 130 is a generally tubular member defining a plurality of leaflet windows 137 coupled together by connecting elements 139, in accordance with an embodiment. The leaflet frame 130 comprises a leaflet frame first end 138*a* and a leaflet frame second end 138*b* opposite the leaflet frame first end 138*a*. The leaflet frame 130 comprises a leaflet frame outer surface 132*a* and a leaflet frame inner surface 132*b* opposite the outer surface 132*a*, as shown in FIG. 5A. The leaflet frame first end 138*a* and the leaflet frame second end 138*b* define a generally zigzag configuration to facilitate flexion about flex points 136 such as which facilitates compression and expansion between different diameters for compression onto a delivery device and expansion by a balloon for the transcatheter valve 100 embodiments, as generally explained for the outer frame 120. As will be discussed later, the surgical prosthetic heart valve 100 embodiment may or may not have the zigzag configuration since the surgical prosthetic heart valve 100 may be of a fixed diameter and need not be operable to compress and re-expand.

The leaflet frame 130 may be referred to in a general sense as a stent or a frame.

The leaflet frame 130 defines a predetermined repeating pattern as shown in FIG. 2B, in accordance with an embodiment. The leaflet frame 130 defines three interconnected leaflet windows 137 having a substantially triangular shape. Each of the leaflet windows 137 include two leaflet window sides 133, a leaflet window base 134, and a leaflet window top 135. In this embodiment, the leaflet window base 134 defines a flex point 136 which will be described further below. A leaflet window side 133 and leaflet window top 135 of one leaflet window 137 is interconnected with a leaflet window side 133 of an adjacent leaflet window 137.

The leaflet frame 130 defines any number of features and geometric shapes that facilitate substantially uniform circumferential compression and expansion. The leaflet frame 130 may comprise a cut tube, or any other element suitable for the particular purpose. The leaflet frame 130 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

The leaflet frame 130 can comprise any metallic or polymeric biocompatible material. For example, the leaflet frame 130 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

As will be described in more detail below, a film 160 is disposed over each of the three leaflet windows 137 to form a leaflet 140. Further embodiments will be described below wherein the leaflet window 137 defines shapes other than a substantially triangular shape, including, but not limited to a parabolic shape and a trapezoidal shape, with and without a leaflet window top 135, suitable for a particular purpose of an embodiment of a surgical and transcatheter valve 100.

Figure 7A:
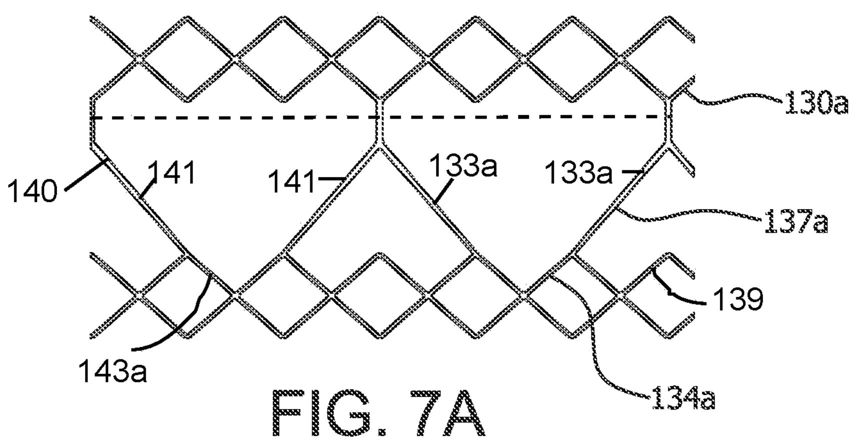
FIG. 7A is an embodiment of a leaflet frame unrolled to a flat orientation.
Figure 7B:
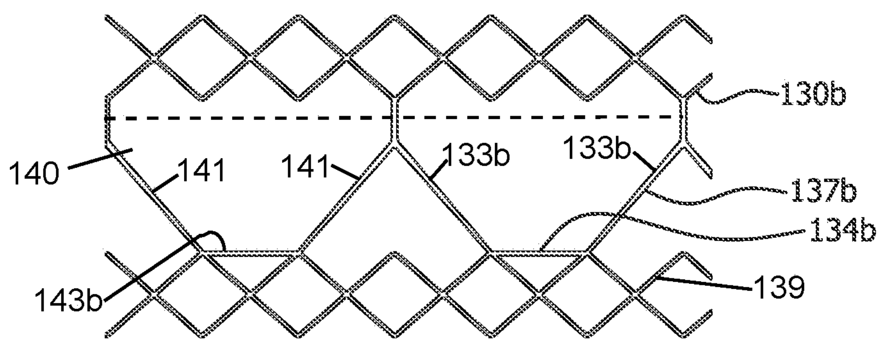
FIG. 7B is an embodiment of a leaflet frame unrolled to a flat orientation.

FIGS. 7A and 7B are side views of alternative embodiments of the leaflet frame 130*a*, 130*b* wherein the leaflet frame has been longitudinally cut and laid open to better illustrate the elements of the leaflet frame. The leaflet frame 130*a* includes leaflet windows 137*a* having a substantially triangular shape defining a pointed leaflet window base 134*a*. The leaflet frame 130*b* includes leaflet windows 137*b* having a substantially triangular shape defining a flat leaflet window base 134*b*. The flat leaflet window base 134*b* may be used to define the leaflet base.

Figure 8A:
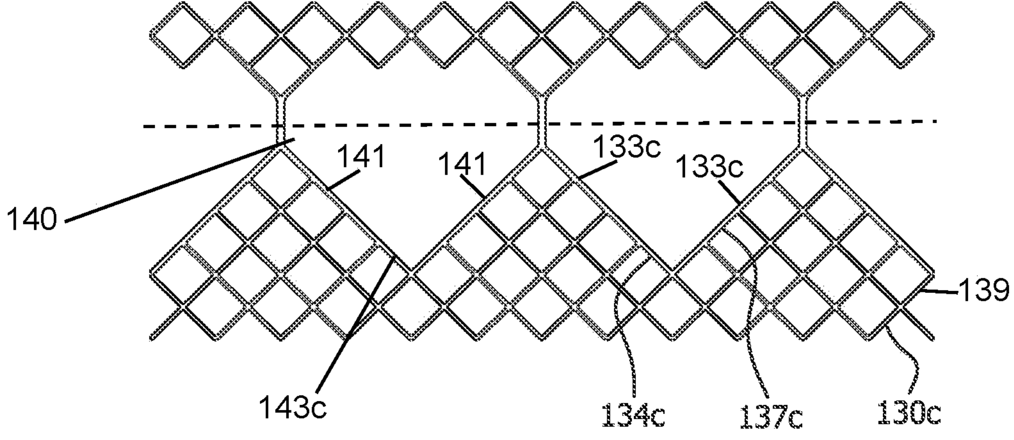
FIG. 8A is an embodiment of a leaflet frame unrolled to a flat orientation.
Figure 8B:
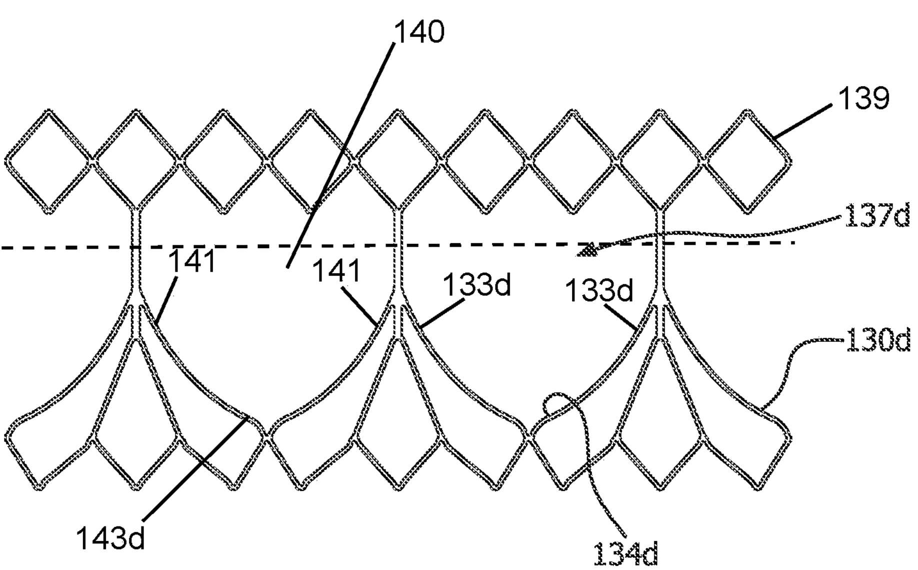
FIG. 8B is an embodiment of a leaflet frame unrolled to a flat orientation.
Figure 8C:
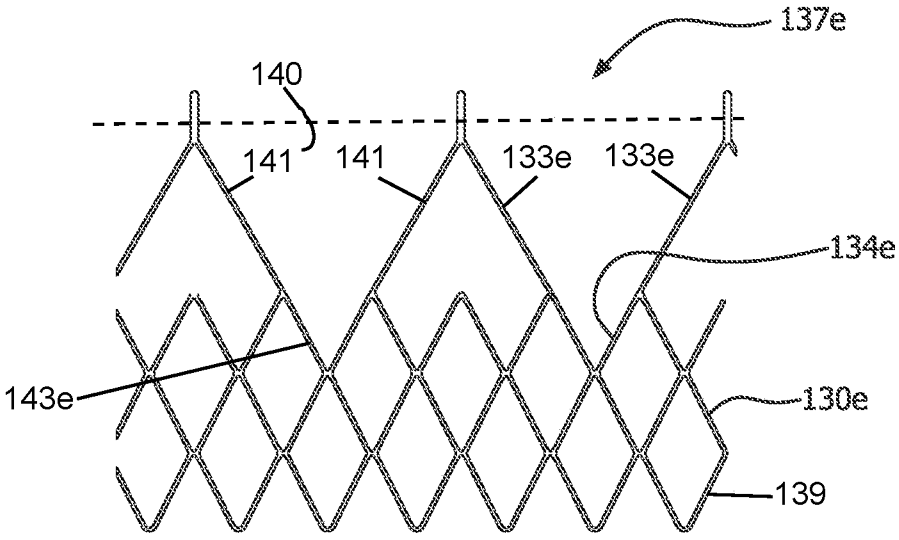
FIG. 8C is an embodiment of a leaflet frame unrolled to a flat orientation.

FIGS. 8A-8C are side views of alternative embodiments of the leaflet frame 130*c*-130*e* wherein the leaflet frame has been longitudinally cut and laid open to better illustrate the elements of the leaflet frame. The leaflet frame 130*c* includes leaflet windows 137*c* having a substantially triangular shape defining a pointed leaflet window base 134*c*. The leaflet frame 130*d* includes leaflet windows 137*d* having a substantially parabolic shape defining a rounded leaflet window base 134*d*. The flat leaflet window base 134*b* may be used to define the leaflet base. The leaflet frame 130*e* includes leaflet windows 137*e* having a substantially triangular shape defining a pointed leaflet window base 134*c* but not having a leaflet window top.

FIG. 8*d* is a side view of an alternative embodiment of the leaflet frame 130*f* wherein the leaflet frame 130*f* has been longitudinally cut and laid open to better illustrate the elements of the leaflet frame. The leaflet frame 130*f* includes leaflet windows 137*f* having a substantially isosceles trapezoid shape defining a flat leaflet window base 134*f*. The flat leaflet window base 134*f* may be used to define the leaflet base. In accordance with other embodiments of the prosthetic valve, each leaflet 140*f* has substantially the shape of an isosceles trapezoid having two leaflet sides 141*f*, a leaflet base 142*f* and a free edge 143*f* opposite the leaflet base, wherein the two leaflet sides diverge from the leaflet base, wherein the leaflet base is substantially flat, as shown in dashed lines in FIG. 8*d*.

FIG. 8*e* is a side view of an alternative embodiment of the leaflet frame 130*g* wherein the leaflet frame 130*g* has been longitudinally cut and laid open to better illustrate the elements of the leaflet frame. The leaflet frame 130*g* includes leaflet windows 137*g* having a substantially isosceles trapezoid shape defining a flat leaflet window base 134*f*. The flat leaflet window base 134*g* may be used to define the leaflet base. In accordance with other embodiments of the prosthetic valve, each leaflet 140*g* has substantially the shape of an isosceles trapezoid having two leaflet sides 141*g*, a leaflet base 142*g* and a free edge 143*g* opposite the leaflet base, wherein the two leaflet sides diverge from the leaflet base, wherein the leaflet base is substantially flat, as shown in dashed lines in FIG. 8*e*.

The frame comprises a plurality of spaced apart leaflet windows 137*f* each leaflet attachment zone defines substantially an isosceles triangle interconnected by a base element 138*f*, wherein each leaflet window side is defined by a side of one triangle and a side of an adjacent triangle, and wherein each leaflet window base is defined by the base element 138*f*.

FIG. 7A is a representation of another embodiment of a leaflet frame 130*a* unrolled to a flat orientation. The leaflet frame 130*a* comprises frame elements 139 suitable for affecting compression and expansion as would be needed for intravascular placement. The leaflet window 137*a* is defined by two leaflet window sides 133*a* that meet at a leaflet window base 134*a*. A leaflet 140 is shown in dashed line to represent where the leaflet 140 is located within the leaflet window 137*a*. The leaflet sides 141 are coupled to the leaflet window sides 133*a* and the leaflet base 143 is coupled to the leaflet window base 134*a*.

FIG. 7B is a representation of another embodiment of a leaflet frame 130*b* unrolled to a flat orientation. The leaflet window 137*b* is defined by two leaflet window sides 133*b* that meet at a leaflet window base 134*b* that is elongated and horizontal with the valve axis. A leaflet 140 is shown in dashed line to represent where the leaflet 140 is located within the leaflet window 137*a*. The leaflet sides 141 are coupled to the leaflet window sides 133*a* and the leaflet base 143*b* is coupled to the leaflet window base 134*a*. The leaflet window base 134*b* is flat such that the leaflet bends from a flat base during opening and closing.

FIG. 8A is a representation of another embodiment of a leaflet frame 130*c* unrolled to a flat orientation. The leaflet frame 130*c* comprises frame elements 139 suitable for affecting compression and expansion as would be needed for intravascular placement. The leaflet window 137*c* is defined by two leaflet window sides 133*c* that meet at a leaflet window base 134*c*. A leaflet 140 is shown in dashed line to represent where the leaflet 140 is located within the leaflet window 137*c*. The leaflet sides 141 are coupled to the leaflet window sides 133*c* and the leaflet base 143*c* is coupled to the leaflet window base 134*c*.

FIG. 8B is a representation of another embodiment of a leaflet frame 130*d* unrolled to a flat orientation. The leaflet frame 130*d* comprises frame elements 139 suitable for affecting compression and expansion as would be needed for intravascular placement. The leaflet window 137*d* is defined by two leaflet window sides 133*d* that meet at a leaflet window base 134*d*. A leaflet 140 is shown in dashed line to represent where the leaflet 140 is located within the leaflet window 137*d*. The leaflet sides 141 are coupled to the leaflet window sides 133*d* and the leaflet base 143*d* is coupled to the leaflet window base 134*d*. The leaflet window sides 133*d* define a parabolic shape.

FIG. 8C is a representation of another embodiment of a leaflet frame 130*e* unrolled to a flat orientation. The leaflet frame 130*e* comprises frame elements 139 suitable for affecting compression and expansion as would be needed for intravascular placement. The leaflet window 137*e* is defined by two leaflet window sides 133*e* that meet at a leaflet window base 134*e*. A leaflet 140 is shown in dashed line to represent where the leaflet 140 is located within the leaflet window 137*e*. The leaflet sides 141 are coupled to the leaflet window sides 133*e* and the leaflet base 143*e* is coupled to the leaflet window base 134*a*.

FIG. 8D is a side view of an alternative embodiment of the leaflet frame 130*f* wherein the leaflet frame 130*f* has been longitudinally cut and laid open to better illustrate the elements of the leaflet frame 130*f*, of a valve substantially shown as the prosthetic heart valve 100 of FIGS. 11A and 11B. A leaflet 140*f* is shown in dashed line to represent where the leaflet 140*f* is located within the leaflet window 137*f*, the leaflet window 137*f* being defined by the leaflet window sides 133*f* and the leaflet window base 134*f*. The two leaflet sides 141*f* diverge from the leaflet base 143*f*, wherein the leaflet base 143*f* is substantially flat, with the leaflet free edge 142*f* opposite the leaflet base 143*f*, as shown in dashed lines in FIG. 8D. The leaflet frame 130*f* further defines commissure posts 136 from which the leaflet free edge 142*f* extends.

FIG. 8E is a side view of an alternative embodiment of the leaflet frame 130*g* wherein the leaflet frame 130*g* has been longitudinally cut and laid open to better illustrate the elements of the leaflet frame 130*g*. A leaflet 140*g* is shown in dashed line to represent where the leaflet 140*g* is located within the leaflet window 137*g*, the leaflet window 137*g* being defined by the leaflet window sides 133*g* and the leaflet window base 134*g*. Two leaflet sides 141*g* diverge from the leaflet base 143*g*, wherein the leaflet base 143*g* is substantially flat, with the leaflet free edge 142*g* opposite the leaflet base 143*g*, as shown in dashed lines in FIG. 8E. The leaflet frame 130*g* comprises a plurality of leaflet frame elements defining a plurality of isosceles triangles interconnected by a leaflet window base 134*g* defining leaflet windows 137*g* that define isosceles trapezoids. Each leaflet window side 133*g* is defined by a side of one triangle and a side of an adjacent triangle.

FIG. 8F is a side view of an alternative embodiment of the leaflet frame 130*h* wherein the leaflet frame 130*h* has been longitudinally cut and laid open to better illustrate the elements of the leaflet frame 130*h*. The leaflet frame 130*h* comprises a base element 138*h* and a plurality of spaced apart spade elements 170 interconnected by the base element 138*h*. Each leaflet window 137*h* is defined by a spade side 175 of one spade element 170 and a spade side 175 of an adjacent spade element 170, and wherein each leaflet window base 134*h* is defined by the base element 138*h*. The spade side 175 does not extend to the base element 138*h*. By virtue of the geometry, the leaflet 140*h*, during opening and closing, will bend about the spade side 175 and towards the base element 138*h* defining a partially frameless leaflet window 137*h* where the leaflet 140 is not bending directly adjacent a frame element 139, defining an attachment zone 163. The leaflet base 143*h* may be defined a distance away from the base element 138*h* such that the leaflet base 143*h* is not bending directly adjacent the base element 138*h*. A leaflet base 143*h* that is not directly adjacent the base element 138*h* is referred herein as a virtual leaflet window base, virtual in the sense that it is not defined directly by a frame element. In accordance with an embodiment of the prosthetic heart valve, each leaflet 140*h* takes the farm of substantially the shape of an isosceles trapezoid having two leaflet sides 141*h*, a leaflet base 143*h* and a leaflet free edge 142*h* opposite the leaflet base 143*h*, wherein the two leaflet sides 141*h* diverge from the leaflet base 143*h*, wherein the leaflet base 143*h* is substantially flat, as shown in dashed lines in FIG. 8F.

In accordance with an embodiment, the leaflet frame comprises a frame first end and a frame second end opposite the frame first end, the leaflet window having a shape determined, at least in part, by wrapping a two dimensional isosceles trapezoid onto the tubular shape of the frame, the isosceles trapezoid having a base and two sides that diverge from the base, and wherein a side from adjacent isosceles trapezoids meet at the frame second end.

In another embodiment substantially as shown in FIG. 8F, a first layer of film 160*a* is coupled to a leaflet frame inner surface 132*b* of the leaflet frame 130*h* and a second layer of film 160*b* is coupled to a leaflet frame outer surface 132*a* of the leaflet frame 130*h* opposite from the leaflet frame inner surface 132*b*. The first layer of film 160 and the second layer of film 160*b* are coupled together to define an attachment zone 163.

As previously discussed, the leaflet window base may be used to define the leaflet base in accordance with embodiments. Also as previously discussed, the leaflet base may be defined as a virtual leaflet base 143 by a fold line 145 in the film 160 in the fold region spaced apart from the leaflet window base 134, as shown in FIGS. 1A and 1B, and shown by the dashed lines in FIG. 2B. It is appreciated that there are many embodiments of the outer frame having configurations suitable for the particular purpose.

Figure 10A:
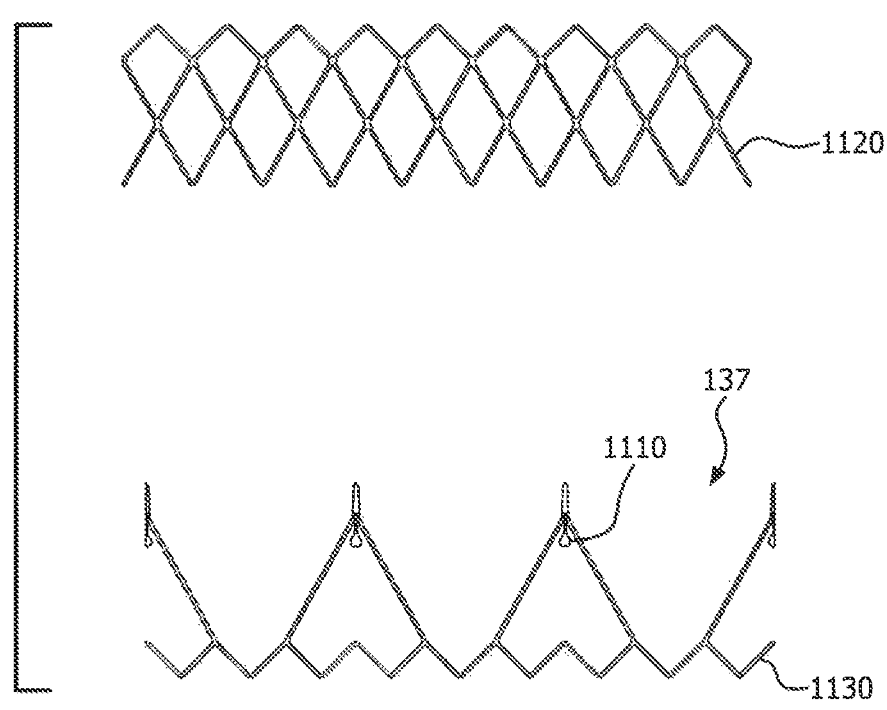
FIG. 10A is a side exploded view of a leaflet frame and an outer frame that may be coupled by a mechanical engagement member, in accordance with another embodiment.
Figure 10B:
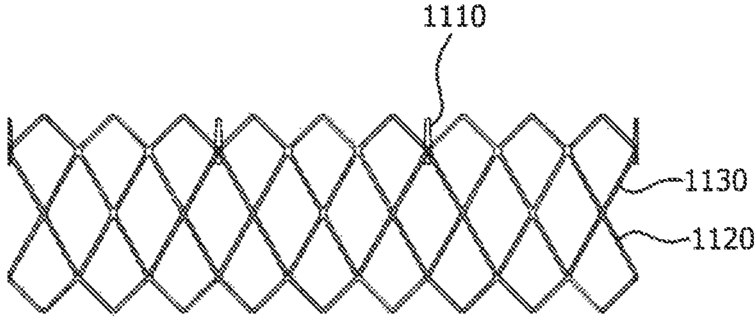
FIG. 10B is a side view of an assembled embodiment of FIG. 10A.

FIG. 10A is a side exploded view of another prosthetic heart valve comprising a leaflet frame 1130 having a generally tubular shape and an outer frame 1120 having a generally tubular shape that are coupled by a mechanical engagement member 1110, in accordance with another embodiment. FIG. 10B is an assembled view of the embodiment of FIG. 10A.

As previously discussed, the leaflet window base may be used to define the leaflet base in accordance with embodiments. Also as previously discussed, the leaflet base may be defined as a virtual leaflet base 143*a* by a fold line 145 in the film 160 in the fold region 144 spaced apart from the leaflet window base, as shown in FIGS. 1B and 2B. It is appreciated that there are many embodiments of the leaflet frame having configurations suitable for the particular purpose.

In transcatheter prosthetic heart valve 100 embodiments, the leaflet frame 130 is elastically, plastically, or both, compressible to obtain a relatively small diameter to accommodate percutaneous transcatheter mounting and delivery.

The leaflet frame 130 may comprise, such as, but not limited to, any elastically deformable metallic or polymeric biocompatible material, in accordance with embodiments. The leaflet frame 130 may comprise a shape-memory material, such as nitinol, a nickel-titanium alloy. Other materials suitable for the leaflet frame 130 include, but are not limited to, other titanium alloys, stainless steel, cobalt-nickel alloy, polypropylene, acetyl homopolymer, acetyl copolymer, other alloys or polymers, or any other biocompatible material having adequate physical and mechanical properties to function as a leaflet frame 130 as described herein.

In accordance with an embodiment, the leaflet frame 130 and the outer frame 120 comprise a shape memory material operable to flex under load and retain its original shape when the load is removed, thus allowing the leaflet frame 130 and the outer frame 120 to self-expand from a compressed shape to a predetermined shape. The leaflet frame 130 and the outer frame 120 may comprise the same or different materials. In accordance with an embodiment the leaflet frame 130 is plastically deformable to be expanded by a balloon. In another embodiment, the outer frame 120 is elastically deformable so as to be self-expanding.

Film

The film 160 is generally any sheet-like material that is biologically compatible and configured to couple to leaflets to the leaflet frame, in accordance with embodiments. It is understood that the term "film" is used generically for one or more biocompatible materials suitable for a particular purpose. The leaflets 140 are also comprised of the film 160.

In accordance with an embodiment, the film 160 that is not of a biological source and that is sufficiently flexible and strong for the particular purpose, such as a biocompatible polymer. In an embodiment, the film 160 comprises a biocompatible polymer that is combined with an elastomer, referred to as a composite.

It is also understood that the film 160 that is coupled to the outer frame 120 may not be the same film 160 that is coupled to the leaflet frame 130, in accordance with embodiments. Details of various types of film 160 are discussed below. In an embodiment, the film 160 may be formed from a generally tubular material to at least partially cover the outer frame 120 and the leaflet frame 130. The film 160 can comprise one or more of a membrane, composite material, or laminate. Details of various types of film 160 are discussed below.

Leaflet

Each leaflet window 137 is provided with a film 160, which is coupled to a portion of the leaflet window sides 133 with the film 160 defining a leaflet 140. Each leaflet 140 defines a leaflet free edge 142 and a leaflet base 143, in accordance with an embodiment. As will be described below, it is anticipated that a plurality of embodiments of leaflet base configurations may be provided. In accordance with an embodiment, the film 160 is coupled to a portion of the leaflet window sides 133 and to the leaflet window base 134 where the leaflet 140 is defined by the portion of the leaflet window sides 133 and to the leaflet window base 134. In accordance with another embodiment, the film 160 is coupled to a portion of the leaflet window sides 133 but not the leaflet window base 134 of the leaflet frame 130 where the leaflet 140 is defined by the portion of the leaflet window sides 133 and to a virtual leaflet base 1033 defined in a fold region as will be described below.

The shape of the leaflets 140 are defined in part by the shape of the leaflet window 137 and the leaflet free edge 142. As will be discussed below in accordance with an embodiment, the shape of the leaflets 140 also depends in part on a process that induces a fold at the fold line 145 to define a virtual leaflet base 143*a* as will be described further below, so as to impart a predetermined shape to the leaflet 140. Since high bending stresses are located at the leaflet base, defining a virtual leaflet base 143*a* that is not bound by the leaflet window base 134 may reduce the chance of tearing of the leaflet 140 at the leaflet base 143—leaflet window base 134 interface. It may also reduce blood pooling and stagnation at the leaflet base as compared with a rounded leaflet base.

When the leaflets 140 are in a fully open position, the prosthetic heart valve 100 presents a substantially circular valve orifice 102 as shown in FIG. 3A. Fluid flow is permitted through the valve orifice 102 when the leaflets 140 are in an open position.

As the leaflets 140 cycle between the open and closed positions, the leaflets 140 generally flex about the leaflet base 143 and the portion of the leaflet window sides 133 to which the leaflet are coupled. When the prosthetic heart valve 100 is closed, generally about half of each leaflet free edge 142 abuts an adjacent half of a leaflet free edge 142 of an adjacent leaflet 140, as shown in FIG. 3B. The three leaflets 140 of the embodiment of FIG. 3B meet at a triple point 148. The valve orifice 102 is occluded when the leaflets 140 are in the closed position stopping fluid flow.

Referring to FIG. 3B, in accordance with an embodiment, each leaflet 140 includes a central region 182 and two side regions 184 on opposite sides of the central region 182. The central region 182 is defined by a shape substantially that of an isosceles triangle defined by two central region sides 183, the leaflet base 143 and the leaflet free edge 142. The two central region sides 183 converge from the leaflet base 143 to the leaflet free edge 142. Each of the side regions 184 have a shape substantially that of a triangle and each are defined by one of the central region sides 183, one of the leaflet sides 141, and the leaflet free edge 142.

In accordance with an embodiment, each of the two side regions 184 and the central region 182 are substantially planar when the prosthetic heart valve 100 is in the closed position.

The leaflet 140 can be configured to actuate at a pressure differential in the blood caused, for example, by the contraction of a ventricle or atrium of the heart, such pressure differential typically resulting from a fluid pressure building up on one side of the prosthetic heart valve 100 when closed. As the pressure on an inflow side of the prosthetic heart valve 100 rises above the pressure on the outflow side of the prosthetic heart valve 100, the leaflet 140 opens and blood flows therethrough. As blood flows through the prosthetic heart valve 100 into a neighboring chamber or blood vessel, the pressure equalizes. As the pressure on the outflow side of the prosthetic heart valve 100 rises above the blood pressure on the inflow side of the prosthetic heart valve 100, the leaflet 140 returns to the closed position generally preventing the retrograde flow of blood through the inflow side of the prosthetic heart valve 100.

It is understood that the leaflet frame 130 may comprise any number of leaflet windows 137, and thus leaflets 140, suitable for a particular purpose, in accordance with embodiments. Leaflet frames 130 comprising one, two, three or more leaflet windows 137 and corresponding leaflets 140 are anticipated.

Figure 1E:
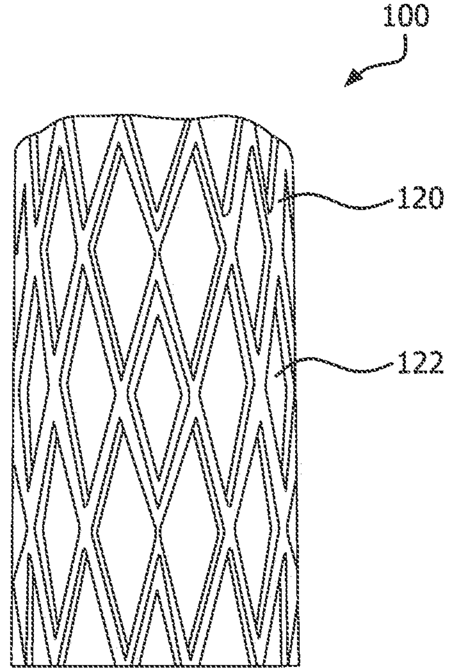
FIG. 1E is a representation of a prosthetic heart valve in a compressed configuration.

In accordance with an embodiment of a transcatheter prosthetic heart valve 100, with reference to FIGS. 1D-1E, the prosthetic heart valve 100 may be compressed into a collapsed configuration having a smaller diameter and expanded into an expanded configuration so that the prosthetic heart valve 100 can be delivered via catheter in the collapsed configuration and expanded upon deployment within the tissue orifice 150 as shown in FIG. 4A. The outer frame 120 can be operable to recover circumferential uniformity when transitioning from the collapsed configuration to the expanded configuration.

Leaflet Film

The film 160 that makes up the leaflet 140 can comprise any biological tissue or synthetic, biocompatible materials sufficiently compliant and flexible, such as a biocompatible polymer. In an embodiment, the leaflet 140 comprises a biocompatible polymer that is combined with an elastomer, referred to as a composite. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

In another embodiment, the expanded fluoropolymer membrane has a microstructure of substantially only fibrils, as is generally taught by U.S. Pat. No. 7,306,729, to Bacino. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5\times10^5$ $MPa^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 μm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 μm and a mass per area of about 4.1 $g/m^2$.

The expanded fluoropolymer membrane combined with elastomer to form a composite material provides the elements of the present disclosure with the performance attributes required for use in high-cycle flexural implant applications, such as prosthetic heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium that may be drawn into the membrane from contact with the blood. If calcium becomes incorporated into the composite material, as used in a prosthetic heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minim um percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones (organopolysiloxanes), copolymers of silicon-urethane, styrene/isobutylene copolymers, polyisobutylene, polyethylene-co-poly (vinyl acetate), polyester copolymers, nylon copolymers, fluorinated hydrocarbon polymers and copolymers or mixtures of each of the foregoing.

Other Considerations

In accordance with an embodiment, the prosthetic heart valve can be configured to prevent interference with a heart conduction system by not covering a bundle branch in the left ventricle when implanted, such as might be encountered with an aortic valve replacement procedure. For example, the prosthetic heart valve can comprise a length of less than about 25 mm or less than about 18 mm. The prosthetic heart valve can also comprise an aspect ratio of less than one, wherein the ratio describes the relationship between the length of the prosthetic heart valve to the expanded, functional diameter. However, the prosthetic heart valve can be constructed at any length and, more generally, any desirable dimension.

In a transcatheter embodiment, in a collapsed state, the prosthetic heart valve can have a collapsed profile that is less than about 35% of the expanded profile. For example, the prosthetic heart valve 100 comprising a 26 mm expanded diameter can have a collapsed diameter of less than about 8 mm, or less than about 6 mm. The percent difference in diameter is dependent on dimensions and materials of the prosthetic heart valve and its various applications, and therefore, the actual percent difference is not limited by this disclosure.

The prosthetic heart valve can further comprise a bio-active agent. Bio-active agents can be coated onto a portion or the entirety of the film 160 for controlled release of the agents once the prosthetic heart valve is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxy urea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Transcatheter Delivery System

In an embodiment, with reference to FIG. 4A, a valve delivery system 500 comprises a prosthetic heart valve 100 having a collapsed configuration and an expanded configuration as previously described and an elongated flexible catheter 480, such as a balloon catheter, configured to deploy the prosthetic heart valve 100 via catheter. The catheter 480 can comprise a balloon to expand the prosthetic heart valve 100 and/or if required, to touch up the prosthetic heart valve 100 to ensure proper seating. The prosthetic heart valve 100 can be mounted to the distal section of the catheter 480 for delivery through the vasculature. In order to hold the prosthetic heart valve in a collapsed configuration on the catheter 480, the valve delivery system may further comprise a removable sheath (not shown) to closely fit over the transcatheter prosthetic heart valve 100.

A method of delivery can comprise the steps of radially compressing a prosthetic heart valve into its collapsed configuration onto the distal end of an elongate flexible catheter having proximal and distal ends; delivering the prosthetic heart valve to a tissue orifice, such as a native aortic valve orifice, via a transfemoral or transapical route, and expanding the prosthetic heart valve into the tissue orifice. The prosthetic heart valve can be expanded by inflating a balloon.

A method of delivery can comprise the steps of radially compressing a prosthetic heart valve into its collapsed configuration, onto the distal section of an elongated flexible catheter having proximal and distal ends. A restraint, which can be connected to a tether that passes through the orifice of the prosthetic heart valve and the lumen of the catheter, is fitted around the commissure posts of the prosthetic heart valve. The prosthetic heart valve is then delivered to a native valve orifice, such as a native aortic valve orifice, via a route of delivery and expanded into the native orifice. The route of delivery can comprise a transfemoral or transapical route. The prosthetic heart valve can be expanded by inflating a balloon.

Surgical Embodiments

It is appreciated that the embodiments of the prosthetic heart valve 100 may be surgically implanted rather than using transcatheter techniques. Embodiments of a surgically implanted prosthetic heart valve 100 may be substantially the same as those described above, with the addition of a sewing cuff 190 adjacent to the outer frame outer surface 126*a*, shown in FIG. 4B, in accordance with an embodiment. The sewing cuff 190, which is well known in the art, is operable to provide structure that receives suture for coupling the prosthetic heart valve 100 to an implant site, such as the tissue orifice 150. The sewing cuff 190 may comprise any suitable material, such as, but not limited to, double velour polyester. The sewing cuff 190 may be located circumferentially around the outer frame 120.

Method of Making

Figure 9A:
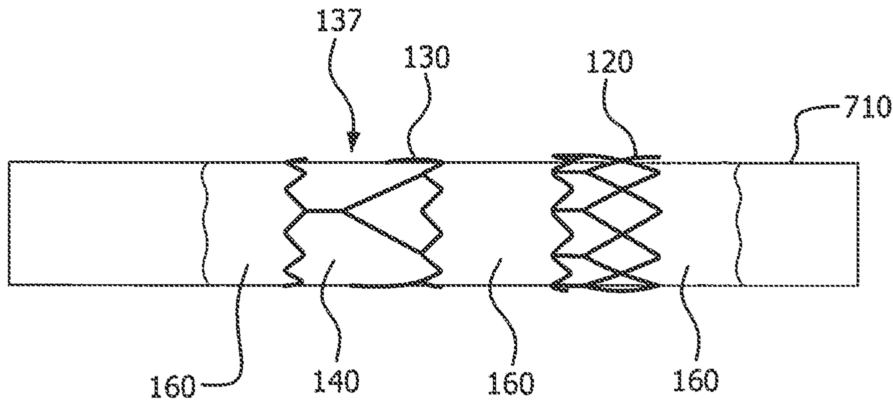
FIG. 9A is a side view of a leaflet frame and an outer frame on an assembly mandrel, in accordance with an embodiment.

Embodiments described herein also pertain to a method of making the prosthetic heart valve 100 embodiments as described herein. In order to make the various embodiments, a cylindrical mandrel 710 can be used. With reference to FIG. 9A, the mandrel 710 comprises a structural form operable to receive the outer frame 120 thereon.

Figure 9B:
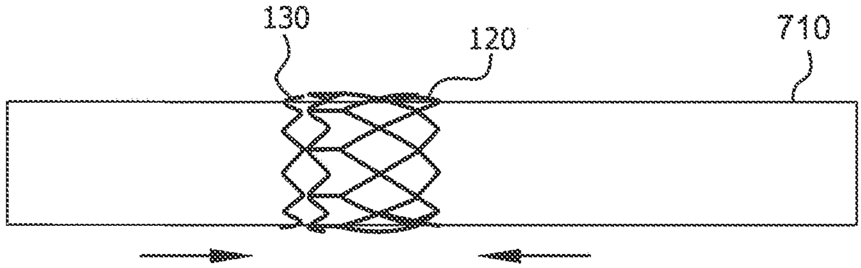
FIG. 9B is a side view of the leaflet frame and the outer frame as nested together on an assembly mandrel, in accordance with the embodiment of FIG. 9A.

With reference to FIGS. 9A and 9B, an embodiment of a method of making a prosthetic heart valve 100 comprises the steps of wrapping a first layer of film 160, e.g., a composite as described herein, into a tubular form about the mandrel 710; placing the leaflet frame 130 and outer frame 120 over the first layer of film 160, as shown in FIG. 9A; forming a second layer of film 160 over the leaflet frame 130 and the outer frame 120; thermally setting the assembly; cutting the film 160 across the leaflet window top within the leaflet window 137, masking with release material 170 a portion of the film 160 in the leaflet window that defines the leaflet 140 to prevent further bonding of leaflet 140 during subsequent processing steps; wrapping a second layer of film 160 into a tubular form over the 120, and over the first layer of film 160; thermal setting the assembly; remove the assembly from the mandrel.

Figure 12:
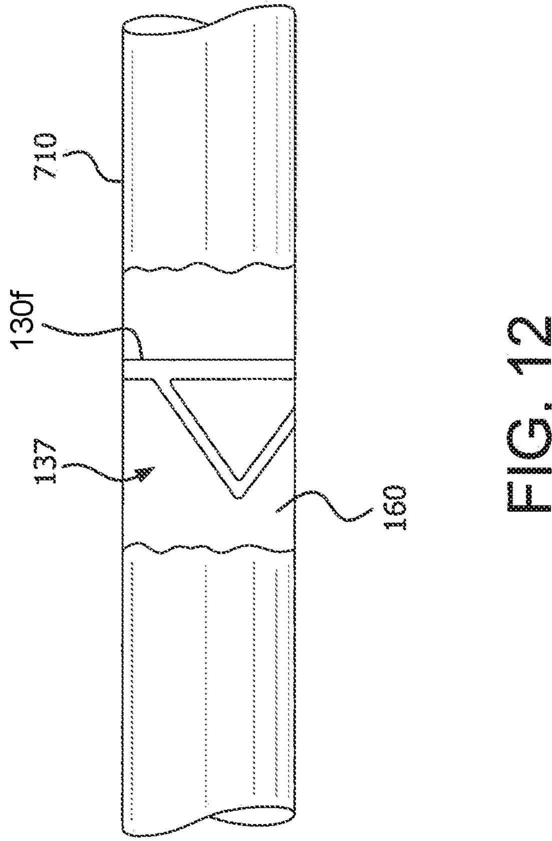
FIG. 12 is a side view of a leaflet frame on an assembly mandrel, in accordance with an embodiment of FIGS. 11A and 11B.
Figures 13A, 13B:
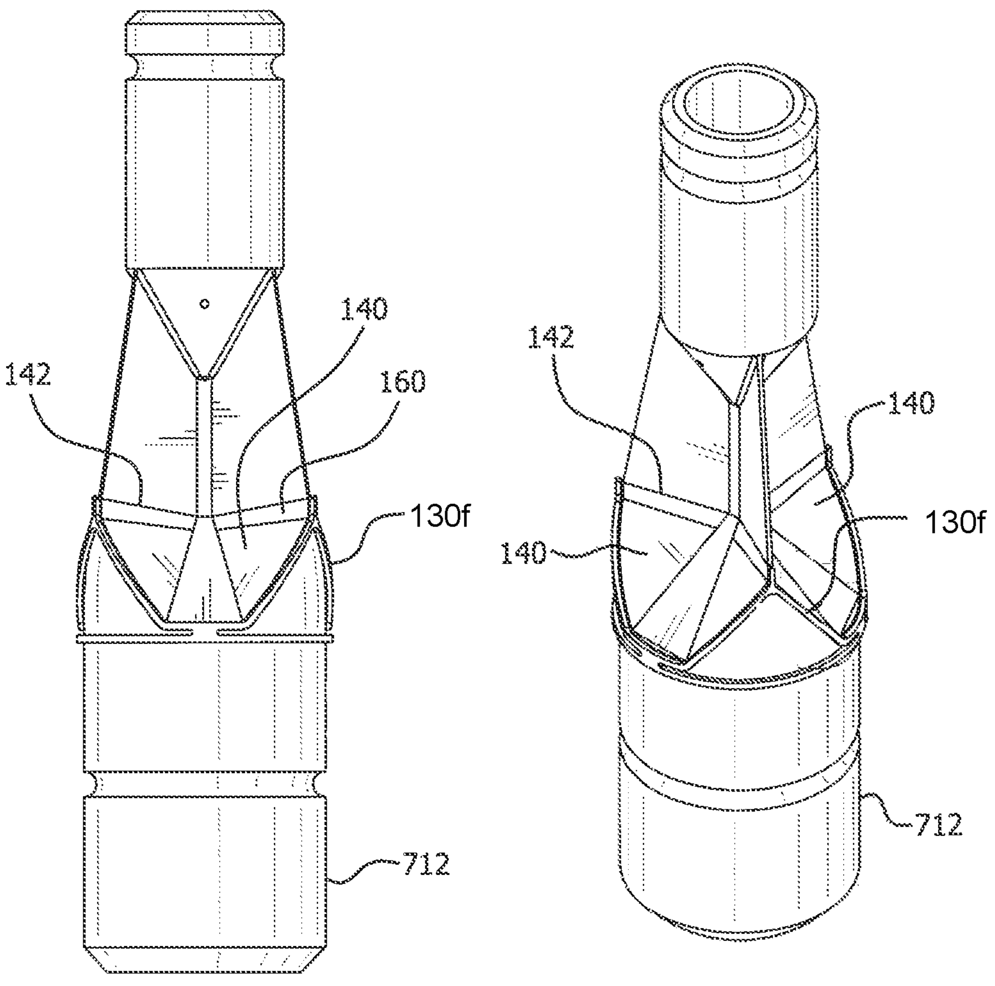
FIG. 13A is a side view of the leaflet frame on a cutting mandrel, in accordance with an embodiment.
FIG. 13B is a perspective view of the leaflet frame on the cutting mandrel of FIG. 13A.
Figure 14:
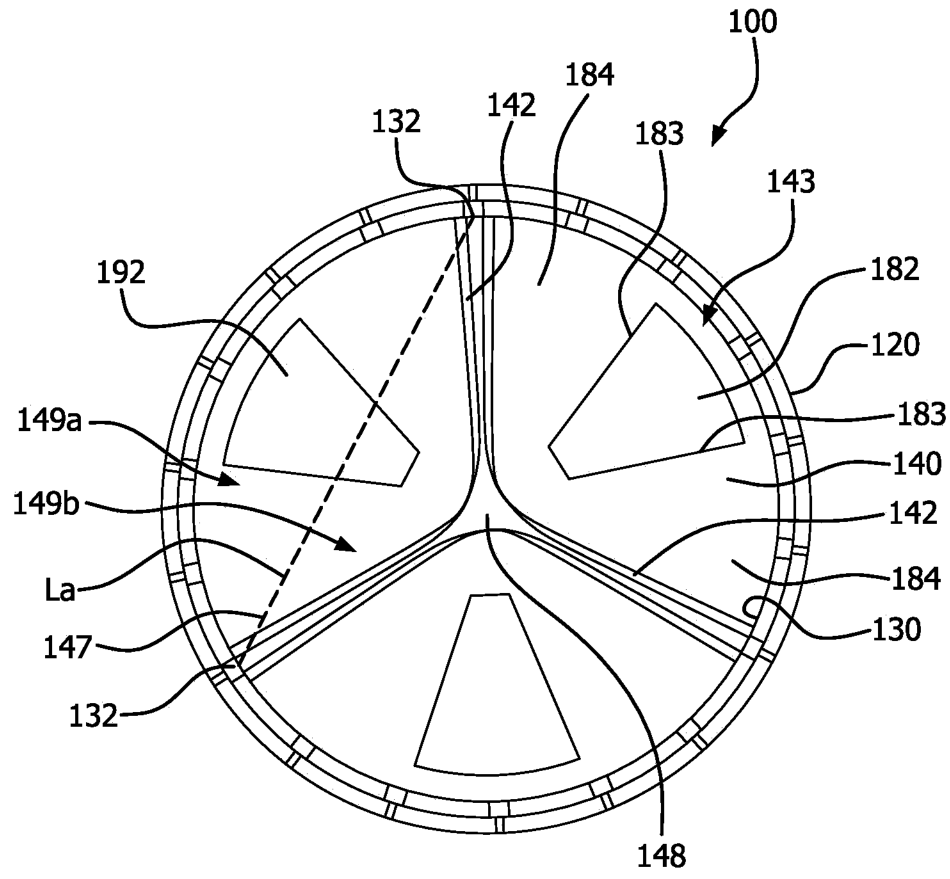
FIG. 14 is an axial view of an embodiment of a prosthetic heart valve in an open configuration.
Figure 15:
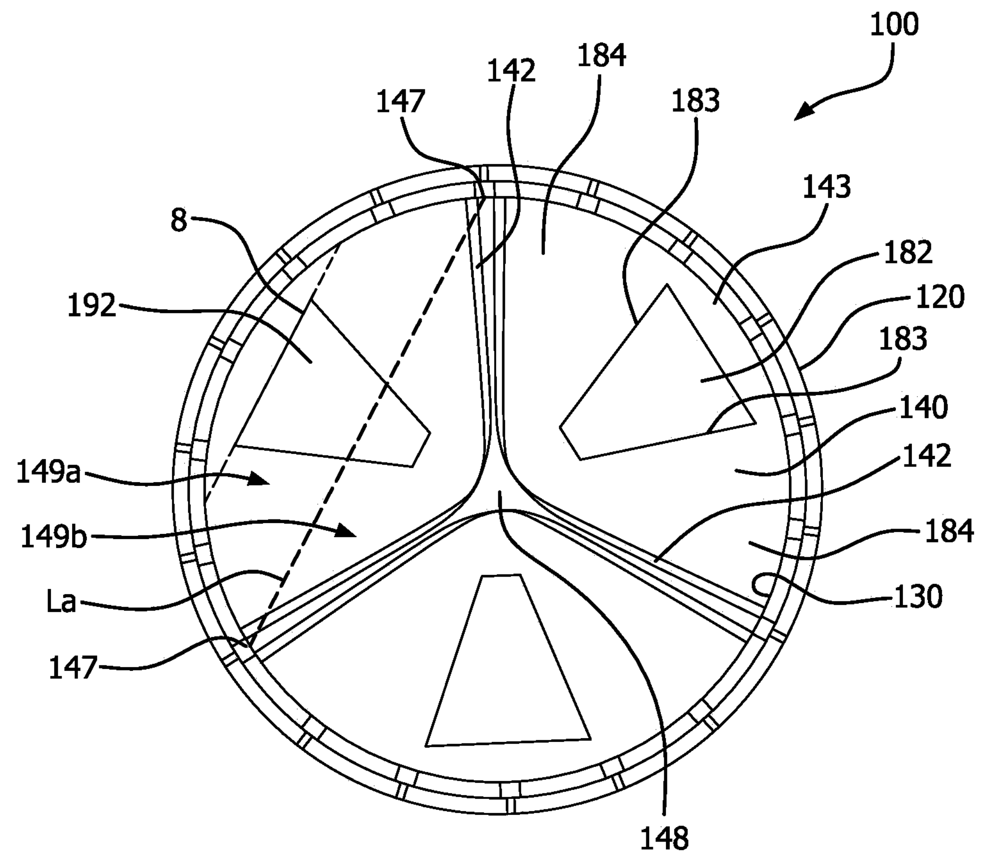
FIG. 15 is an axial view of an embodiment of a prosthetic heart valve in an open configuration.

Embodiments described herein also pertain to a method of making the prosthetic heart valve 200 embodiments as described herein. In order to make the various embodiments, a cylindrical mandrel 710 can be used. With reference to FIG. 12, the mandrel 710 comprises a structural form operable to receive the leaflet frame 130 thereon. An embodiment of a method of making a prosthetic heart valve 200 comprises the steps of wrapping a first layer of film 160, e.g., a composite as described herein, into a tubular form about the mandrel 710; placing the leaflet frame 130 over the first layer of film 160, as shown in FIG. 12; forming a second layer of film 160 over the leaflet frame 130; thermally setting the assembly; receiving the assembly over a cutting mandrel 712 as shown in FIGS. 13A and 13B; cutting the film 160 across the leaflet window top within the leaflet window 137, resulting in the prosthetic heart valve 200 of FIGS. 11A and 11B. FIG. 11A is a side view of an embodiment of a prosthetic heart valve and FIG. 11B is a perspective view of the embodiment of the prosthetic heart valve of FIG. 11A. In FIGS. 11A and 11B the leaflets 140 are shown slightly open as when held by the cutting mandrel 712. It is understood that a fully closed prosthetic heart valve 200 will have the leaflet free edges 142 of the leaflets 140 coming together to coapt under the influence of downstream fluid pressure which results in closing the valve to prevent downstream blood from flowing retrograde through the valve.

EXAMPLES

Example 1

A prosthetic heart valve was produced having polymeric leaflets formed from a composite material having an expanded fluoropolymer membrane and an elastomeric material and joined between two collapsible metallic frames.

The leaflet frame and outer frame were laser machined from a length of SS316LVM tube hard tempered with an outside diameter of 23.0 mm and a wall thickness of 0.65 mm in the shape shown illustratively and generally indicated in FIG. 9A. The leaflet frame 130 and outer frame 120 were electro-polished resulting in 0.0127 mm material removal from each surface and leaving the edges rounded.

Fluorinated ethylene propylene (FEP) powder (Daikin America, Orangeburg N.Y.) was then applied to the leaflet frame 130 and outer frame 120. More specifically, the FEP powder was stirred to form an airborne "cloud" in an enclosed blending apparatus, such as a standard kitchen type blender, while the leaflet frame and outer frame were suspended in the cloud. The leaflet frame and outer frame were exposed to the FEP powder cloud until a uniform layer of powder was adhered to the entire surface of the leaflet frame and outer frame. The leaflet frame and outer frame were then subjected to a thermal treatment by placing it in a forced air oven set to 320° C. for approximately three minutes. This caused the powder to melt and adhere as a thin coating over the entire leaflet frame and outer frame. The leaflet frame and outer frame were removed from the oven and left to cool to room temperature.

Initial Assembly and Thermal Process Cycle

A 21 mm diameter vented metal cylindrical mandrel having a diameter corresponding to the inner diameter of the leaflet frame 130 and outer frame 120 was helically wrapped with sintered ePTFE fiber. A thin film of type 1 (ASTM D3368) FEP was constructed using melt extrusion and stretching. The type 1 (ASTM D3368) FEP film was about 40 μm thick and was about 7.7 cm wide. The mandrel was helically wrapped with one layer of this type 1 FEP film over the sintered ePTFE fiber only in the region of outer frame.

The mandrel was radially wrapped with five layers of an ePTFE membrane with an FEP coating towards the mandrel. The ePTFE membrane was manufactured according to the general teachings described in U.S. Pat. No. 7,306,729. The ePTFE membrane had a mass per area of 2.3 g/m$^2$, a bubble point of 101.5 MPa, a thickness of about 356 nm, a matrix tensile strength of 319 MPa in the longitudinal direction and 407 MPa in the transverse direction.

The mandrel was helically wrapped with one layer of type 1 FEP film.

The diameter of the leaflet frame and outer frame were expanded slightly and received on the wrapped mandrel with approximately a 10 mm space between them, rotational alignment was not necessary.

The leaflet frame, outer frame and the space therebetween were helically wrapped with 1 layer of type 1 FEP film.

The leaflet frame, outer frame and the space therebetween that will become the bridge portion 162 and the fold region 144, as shown in FIG. 2B, were circumferentially wrapped with 5 layers of the same ePTFE membrane with an FEP coating as described above with the coating toward the mandrel.

The wrapped leaflet frame, outer frame and the space therebetween were wrapped with several layers of an ePTFE membrane imbibed with a polyimide material referred to as a release liner.

A substantially nonporous ePTFE membrane was configured into a cylinder and placed over the assembly, referred to as sacrificial tube. Sintered ePTFE fiber was used to seal both ends of the sacrificial tube against the mandrel.

The assembly, including the mandrel, was heated in an oven capable of applying pneumatic pressure external to the sacrificial tube described above and while maintaining a vacuum internal to the mandrel for 40 min such that the mandrel temperature reached approximately 360° C. The assembly was removed from the oven and allowed to cool to room temperature while still pressurized and under vacuum.

The sacrificial tube and release liner was removed. The sintered ePTFE fiber was removed to release the frame assembly from the mandrel.

The polymeric material was trimmed and removed from the leaflet windows of the leaflet frame. The ends of each leaflet frame and outer frame were circumferentially trimmed by a scalpel.

Intermediate Assembly and Thermal Process Cycle

An unsintered 15 mm diameter ePTFE tube was disposed on a 21.5 mm vented metal mandrel. Two layers of a substantially nonporous ePTFE membrane with a FEP coating was circumferentially wrapped on the mandrel with the coating side towards the mandrel. The wrapped mandrel was placed in a convection oven set to 320° C. and heated for 20 min. The ePTFE and substantially nonporous ePTFE membrane combined to serve as a release liner and was perforated to communicate pressure between the vent holes in the mandrel.

The leaflet frame was disposed onto the vented metal mandrel and vent holes were made in the apertures of the leaflet frame over the mandrel vent holes.

A leaflet material was then prepared. A membrane of ePTFE was manufactured according to the general teachings described in U.S. Pat. No. 7,306,729. The ePTFE membrane had a mass per area of 0.452 $g/m^2$, a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, MN) in a 2.5% concentration. The solution was coated using a Mayer bar onto the ePTFE membrane (while being supported by a polypropylene release film) and dried in a convection oven set to 145° C. for 30 seconds. After two coating steps, the final ePTFE/fluoroelastomer or composite had a mass per area of 1.75 $g/m^2$, 29.3% fluoropolymer by weight, a dome burst strength of about 8.6 KPa, and thickness of 0.81 μm.

The following test methods were used to characterize the ePTFE layers and the multi-layered composite. The thickness was measured with a Mutitoyo Snap Gage Absolute, 12.7 mm (0.50") diameter foot, Model ID-C112E, Serial #10299, made in Japan. The density was determined by a weight/volume calculation using an Analytical Balance Mettler PM400 New Jersey, USA. The force to break and tensile strengths were measured using an Instron Model #5500R Norwood, MA, load cell 50 kg, gage length=25.4 cm, crosshead speed=25 mm/minute (strain rate=100% per minute) with flat faced jaws. Unless otherwise noted, these test methods were used to generate the data in subsequent examples.

Ten layers of the composite leaflet material were wrapped around the leaflet frame with an elastomer rich side of the composite facing towards the mandrel. In exemplary embodiments, the composite material is oriented to have a predetermined matrix tensile strength along a direction generally perpendicular with the longitudinal axis of the combined tool assembly. More specifically, the predetermined matrix tensile strength is about 705 MPa.

The mandrel was radially wrapped with one layer of a substantially nonporous ePTFE membrane with an FEP coating towards the mandrel with a spacing 8 mm from the base of the leaflet frame. The ePTFE membrane was manufactured according to the general teachings described in U.S. Pat. No. 7,306,729. The ePTFE membrane had a mass per area of about 11 $g/m^2$, a thickness of about 5.5 μm, a matrix tensile strength of 310 MPa in the longitudinal direction and 103 MPa in the transverse direction.

A Kapton® (El DuPont de Nemours, Inc., Wilmington, DE) polyimide film acting as a mask was wrapped over the substantially nonporous ePTFE membrane with an FEP coating layer.

The outer frame was placed on the mandrel with 10 mm spacing between the leaflet frame and the outer frame. The leaflet frame and the outer frame were aligned such that the longitudinal outer frame posts were collinear with the leaflet frame commissure posts.

The leaflet frame and outer frame were wrapped with 24 layers of the composite leaflet material described earlier with an elastomer rich side of the composite facing towards the mandrel. In exemplary embodiments, the composite material is oriented to have a predetermined matrix tensile strength along a direction generally perpendicular with the longitudinal axis of the combined tool assembly. More specifically, the predetermined matrix tensile strength is about 705 MPa.

The final leaflet was comprised of 29.3% fluoropolymer by weight with a thickness of approximately 27 μm. Each leaflet had 34 layers of the composite and a ratio of thickness/number of layers of 0.8 μm.

The mandrel was again radially wrapped with one layer of a substantially nonporous ePTFE membrane with an FEP coating towards the mandrel with a spacing 8 mm from the base of the leaflet frame.

The assembly was wrapped with several layers of the sacrificial release liner. A sacrificial tube was placed over the assembly and sintered ePTFE fiber was used to seal both ends of the sacrificial tube against the mandrel.

The assembly was processed in an oven capable of applying pneumatic pressure external to the sacrificial material configured into a tube described above and while maintaining a vacuum internal to the tube for 25 min such that the mandrel temperature reached approximately 330° C. The assembly was removed from the oven and allowed to cool to room temperature while still pressurized and under vacuum.

The sacrificial tube and liner were removed from the frame assembly and the frame assembly was removed from the mandrel. The Kapton® mask was removed.

A scalpel was used to circumferentially trim the leaflet free edge of each leaflet and the distal end of leaflet frame.

Final Assembly and Thermal Process Cycle

The outer frame was radially expanded to a 24 mm diameter using a tapered mandrel.

A release liner as described above was placed on a 21.5 mm vented mandrel.

Three Kapton® masks were cut to the shape of leaflet window with a 30 mm tapered extension.

The leaflet frame and outer frame with leaflet material were placed onto the mandrel and the tapered extensions of the Kapton® masks were inserted under the top ring of the leaflet frame from the trimmed end and were advanced axially until the masks aligned with the leaflet window.

The leaflet frame was wrapped with 2 layers of the type 1 FEP film.

A hot iron was used to remove the FEP film from the leaflet window region by melting it away from the perimeter and to tack the FEP film in all regions of leaflet frame outside the masks.

Vent holes were made within all the leaflet frame apertures and in the polymer tube region connecting the inner frame and outer frame.

While holding the leaflet frame in place, the outer frame was coaxially disposed over the leaflet frame by telescopically inverting the bridge portion of the contiguous tube.

The entire frame assembly was circumferentially wrapped with one substantially nonporous ePTFE membrane with an FEP coating towards the mandrel.

The assembly was wrapped with several layers of the sacrificial release liner. A sacrificial tube was placed over the assembly and sintered ePTFE fiber was used to seal both ends of the sacrificial tube against the mandrel.

The assembly was processed in an oven capable of applying pneumatic pressure external to the sacrificial material configured into a tube described above and while maintaining a vacuum internal to the tube for 25 min such that the mandrel temperature reached approximately 330° C. The assembly was removed from the oven and allowed to cool to room temperature while still pressurized and under vacuum.

The frame assembly was removed from the mandrel.

A scalpel was used to circumferentially trim each end of leaflet frame.

The Kapton was rotationally peeled away from inside the outer frame and away from leaflets.

Using scissors, both ends of the leaflet frame were trimmed to follow frame contour.

The resulting prosthetic heart valve 100 includes leaflets 140 formed from a composite material with more than one fluoropolymer layer having a plurality of pores and an elastomer present in substantially all of the pores of the more than one fluoropolymer layer. Each leaflet 140 is movable between a closed position, shown in FIGS. 3B, in which blood is substantially prevented from flowing through the valve assembly, and an open position, shown in FIG. 3A, in which blood is allowed to flow through the valve assembly. Thus, the leaflets 140 of the prosthetic heart valve 100 cycle between the closed and open positions generally to regulate blood flow direction in a human patient.

The performance of the prosthetic heart valve leaflets was characterized on a real-time pulse duplicator that measured typical anatomical pressures and flows across the prosthetic heart valve. The flow performance was characterized by the following process:

The valve assembly was potted into a silicone annular ring (support structure) to allow the valve assembly to be subsequently evaluated in a real-time pulse duplicator. The potting process was performed according to the recommendations of the pulse duplicator manufacturer (ViVitro Laboratories Inc., Victoria BC, Canada).

The potted valve assembly was then placed into a real-time left heart flow pulse duplicator system. The flow pulse duplicator system included the fallowing components supplied by VSI Vivitro Systems Inc., Victoria BC, Canada: a Super Pump, Servo Power Amplifier Part Number SPA 3891; a Super Pump Head, Part Number SPH 5891B, 38.320 $cm^2$ cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, NC, USA In general, the flow pulse duplicator system uses a fixed displacement, piston pump to produce a desired fluid flow through the prosthetic heart valve under test.

The heart flow pulse duplicator system was adjusted to produce the desired flow (5 L/min), mean pressure (15 mmHg), and simulated pulse rate (70 bpm). The prosthetic heart valve under test was then cycled for about 5 to 20 minutes.

Pressure and flow data were measured and collected during the test period, including right ventricular pressures, pulmonary pressures, flow rates, and pump piston position.

Parameters used to characterize a prosthetic heart valve are effective orifice area and regurgitant fraction. The effective orifice area (EOA), which can be calculated as follows: $EOA(cm^2)=Q_{rms}/(51.6*(AP)^{1/2})$ where $Q_{rms}$ is the root mean square systolic/diastolic flow rate ($cm^3$/s) and AP is the mean systolic/diastolic pressure drop (mmHg).

Another measure of the hydrodynamic performance of a prosthetic heart valve is the regurgitant fraction, which is the amount of fluid or blood regurgitated through the prosthetic heart valve divided by the stroke volume.

The hydrodynamic performance measured values were; EOA=2.06 $cm^2$, and regurgitant fraction=8.2%.

Example 2

Another prosthetic heart valve was made as described in Example 1 with the following exceptions.

Initial Assembly and Thermal Process Cycle

The diameter of the leaflet frame and outer frame were expanded slightly and received on the wrapped mandrel with 16 mm space between them, rotational alignment of the leaflet frame and outer frame was made.

Final Assembly and Thermal Process Cycle

A scalpel was used to cut above the mechanical linking tab. The tab was deformed to link the leaflet frame to the outer frame.

The resulting prosthetic heart valve 100 includes leaflets 140 formed from a composite material with more than one fluoropolymer layer having a plurality of pores and an elastomer present in substantially all of the pores of the more than one fluoropolymer layer. Each leaflet 140 is movable between a closed position, shown in FIG. 3B, in which blood is substantially prevented from flowing through the valve assembly, and an open position, shown in FIG. 3A, in which blood is allowed to flow through the valve assembly. Thus, the leaflets 140 of the prosthetic heart valve 100 cycle between the closed and open positions generally to regulate blood flow direction in a human patient.

The hydrodynamic performance was measured. The performance values were; EOA=2.3 $cm^2$ and regurgitant fraction=11.8%.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

Example 3 (Single Leaflet frame Prosthetic Heart Valve)

In exemplary embodiments, a prosthetic heart valve having polymeric leaflets formed from a composite material having an expanded fluoropolymer membrane and an elastomeric material and joined to a semi-rigid, non-collapsible metallic frame, and further a having strain relief was constructed according to the following process:

A leaflet frame was laser machined from a length of MP35N cobalt chromium tube hard tempered with an outside diameter of 26.0 mm and a wall thickness of 0.6 mm in the shape. The leaflet frame was electro-polished resulting in 0.0127 mm material removal from each surface and leaving the edges rounded. The leaflet frame was exposed to a surface roughening step to improve adherence of leaflets to the leaflet frame. The leaflet frame was cleaned by submersion in an ultrasonic bath of acetone for approximately five minutes. The entire metal leaflet frame surface was then subjected to a plasma treatment using equipment (e.g. PVA TePLa America, Inc Plasma Pen, Corona, CA) and methods commonly known to those having ordinary skill in the art. This treatment also served to improve the wetting of the fluorinated ethylene propylene (FEP) adhesive.

FEP powder (Daikin America, Orangeburg N.Y.) was then applied to the leaflet frame. More specifically, the FEP powder was stirred to form an airborne "cloud" in an enclosed blending apparatus, such as a standard kitchen type blender, while the leaflet frame is suspended in the cloud. The leaflet frame was exposed to the FEP powder cloud until a layer of powder was adhered to the entire surface of the leaflet frame. The leaflet frame was then subjected to a thermal treatment by placing it in a forced air oven set to 320° C. for approximately three minutes. This caused the powder to melt and adhere as a thin coating over the entire leaflet frame. The leaflet frame was removed from the oven and left to cool to approximately room temperature.

The strain relief was attached to the leaflet frame in the following manner. A thin (122 μm) walled sintered 15 mm diameter ePTFE tube was disposed on a 24.5 mm vented metal mandrel by stretching radially over a tapered mandrel. Two layers of a substantially nonporous ePTFE membrane with a continuous FEP coating was circumferentially wrapped on the mandrel with the FEP side towards the mandrel. The wrapped mandrel was placed in a convection oven set to 320° C. and heated for 20 min. The ePTFE and substantially nonporous ePTFE membrane combined to serve as an inner release liner and was perforated using a scalpel blade to communicate pressure between the vent holes in the mandrel. This entire release liner is removed in a later step.

A 5 cm length of the thick (990μ) walled partially sintered 22 mm inner diameter ePTFE tube (density=0.3 $g/cm^3$) was disposed onto the 24.5 mm vented metal mandrel with release liner. The ePTFE tube inner diameter was enlarged by stretching it on a tapered mandrel to accommodate the larger mandrel diameter.

A thin (4 μm) film of type 1 FEP (ASTM D3368) was constructed using melt extrusion and stretching. One layer of the FEP was wrapped over the 5 cm length of the ePTFE tube.

The FEP powder coated leaflet frame was disposed onto the vented metal mandrel generally in the middle of the 5 cm span of ePTFE tube and FEP film.

One layer of the FEP was wrapped over the leaflet frame and 5 cm length of the ePTFE tube.

A second 5 cm length of the 990 μm thick/22 mm inner diameter ePTFE tube was disposed onto the assembly layered onto 24.5 mm vented metal mandrel by stretching its radius over a tapered mandrel to accommodate the larger construct diameter.

A substantially nonporous ePTFE membrane was configured into a cylinder at a diameter larger than the construct and placed over the assembly, referred to as sacrificial tube. Sintered ePTFE fiber (e.g. Gore Rastex® Sewing Thread, Part #S024T2, Newark DE) was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 40 min such that the mandrel temperature reached approximately 360° C. (as measured by a thermocouple direct contact with the inner diameter of the mandrel). The assembly was removed from the oven and allowed to cool to approximately room temperature while still under 100 psi pressure and vacuum.

The sacrificial tube was then removed. Approximately 30 psi of pressure was applied to the internal diameter of the mandrel to assist in removal of the assembly. The inner release liner was peeled away from the internal diameter of the assembly by inverting the liner and axially pulling it apart.

The polymeric material was trimmed with a scalpel and removed from the leaflet windows and bottom of the leaflet frame leaving approximately 0.5 to 1.0 mm of material overhang.

A leaflet material was then prepared. A membrane of ePTFE was manufactured according to the general teachings described in U.S. Pat. No. 7,306,729. The ePTFE membrane had a mass per area of 0.452 $g/m^2$, a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, MN) in a 2.5% concentration. The solution was coated using a mayer bar onto the ePTFE membrane (while being supported by a polypropylene release film) and dried in a convection oven set to 145° C. for 30 seconds. After 2 coating steps, the final ePTFE/fluoroelastomer or composite had a mass per area of 1.75 $g/m^2$, 29.3% fluoropolymer by weight, a dome burst strength of about 8.6 KPa, and thickness of 0.81 μm.

The final leaflet was comprised of 28.22% fluoropolymer by weight with a thickness of 50.3 μm. Each leaflet had 26 layers of the composite and a ratio of thickness/number of layers of 1.93 μm.

Figure 11C:
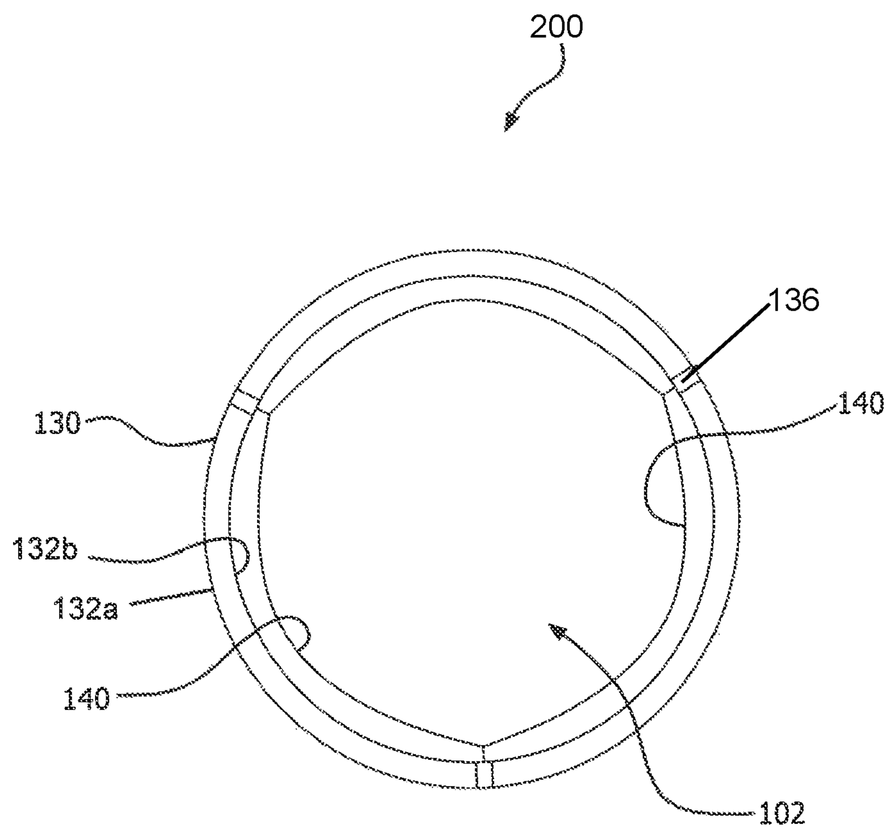
FIG. 11C is an axial or top view of the embodiment of the prosthetic heart valve of FIG. 11A in an open configuration.
Figure 11D:
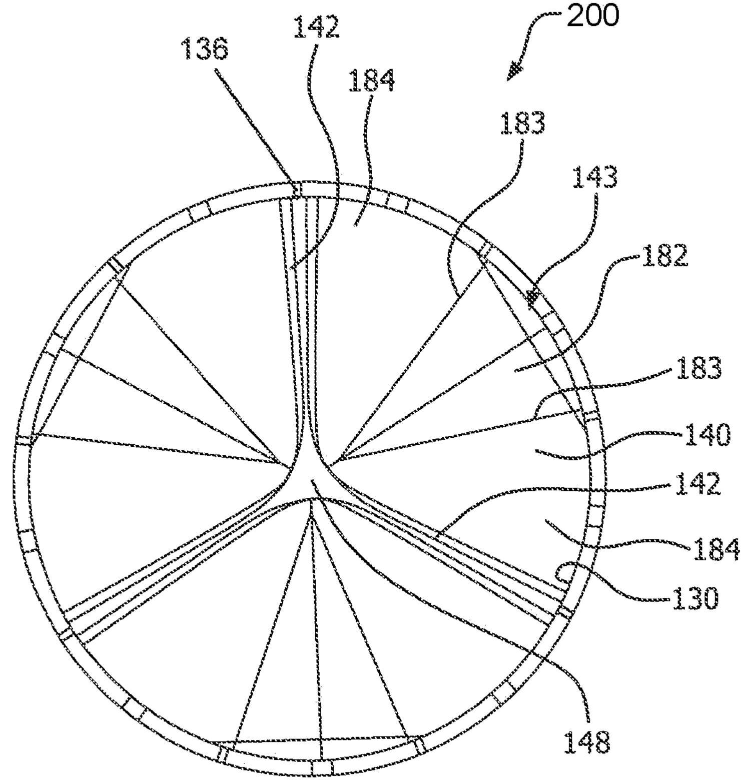
FIG. 11D is an axial or top view of the embodiment of the prosthetic heart valve of FIG. 1A in a closed configuration.

The resulting prosthetic heart valve 200 includes leaflets 140 formed from a composite material with more than one fluoropolymer layer having a plurality of pores and an elastomer present in substantially all of the pores of the more than one fluoropolymer layer. Each leaflet 140 is movable between a closed position, shown illustratively in FIGS. 11D, in which blood is substantially prevented from flowing through the valve assembly, and an open position, shown illustratively in FIG. 11C, in which blood is allowed to flow through the prosthetic heart valve 200. Thus, the leaflets 140 of the prosthetic heart valve 200 cycle between the closed and open positions generally to regulate blood flow direction in a human patient.

The hydrodynamic performance was measured prior to accelerated wear testing. The performance values were; EOA=2.4 $cm^2$ and regurgitant fraction=11.94%.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed:

1. A prosthetic valve comprising:

a radially compressible and expandable frame having a longitudinal axis, an inflow end, and an outflow end, wherein the frame comprises a plurality of angled frame elements arranged in a plurality of circumferentially extending rows of angled frame elements of the plurality of angled frame elements, including a first row of angled frame elements of the plurality of angled frame elements arranged in a zigzag configuration extending in a circumferential direction of the frame, a second row of angled frame elements of the plurality of angled frame elements arranged in a zigzag configuration extending in the circumferential direction of the frame and positioned downstream of the first row of angled frame elements, and a third row of angled frame elements of the plurality of angled frame elements arranged in a zigzag configuration extending in the circumferential direction of the frame and positioned downstream of the second row of angled frame elements, wherein the frame further comprises a row of circumferentially-spaced longitudinal frame posts interconnecting the second and the third row of angled frame elements, wherein each of the longitudinal frame posts extends in a direction parallel to the longitudinal axis; and a plurality of leaflets disposed within a lumen of the frame, each of the leaflets having a leaflet base and a leaflet free edge opposite the leaflet base, the leaflet free edges configured to move between an open position and a closed position during opening-closing cycles associated with blood pressure differentials across the prosthetic valve;

wherein the angled frame elements of the third row of angled frame elements have upper ends connected to each other at a plurality of first junctions and lower ends connected to each other at a plurality of second junctions, wherein the first junctions define the outflow end of the frame and the second junctions are axially offset from the first junctions toward the inflow end of the frame;

wherein the angled frame elements of the second row of angled frame elements have upper ends connected to each other at a plurality of third junctions and lower ends connected to each other at a plurality of fourth junctions;

wherein each longitudinal frame post has an upper end connected to a respective first junction of the third row of angled frame elements and a lower end connected to a respective third junction of the second row of angled frame elements, wherein the lower ends of the longitudinal frame posts terminate at respective third junctions of the second row of angled frame elements, and wherein each third junction comprises an intersection of only the upper ends of two adjacent angled frame elements of the second row of angled frame elements and the lower end of one of the longitudinal frame posts, and is not connected to other portions of the frame.

2. The prosthetic valve of claim 1, wherein the second row of angled frame elements, the third row of angled frame elements, and the row of longitudinal frame posts define a circumferentially extending first row of interconnected cells.

3. The prosthetic valve of claim 2, wherein a circumferentially extending second row of interconnected cells is defined between the first row of angled frame elements and the second row of angled frame elements.

4. The prosthetic valve of claim 3, wherein the frame comprises exactly two circumferentially extending rows of interconnected cells including the first row of interconnected cells and the second row of interconnected cells.

5. The prosthetic valve of claim 4, wherein the first row of interconnected cells is an inflow row of cells, and wherein the second row of interconnected cells is an outflow row of cells.

6. The prosthetic valve of claim 4, wherein the frame comprises exactly three rows of circumferentially extending rows of angled frame elements, including the first row of angled frame elements, the second row of angled frame elements, and the third row of angled frame elements.

7. The prosthetic valve of claim 2, wherein each cell in the first row of interconnected cells is a six-sided cell.

8. The prosthetic valve of claim 6, wherein each cell in the first row of interconnected cells is generally chevron-shaped.

9. The prosthetic valve of claim 3, wherein each cell in the second row of interconnected cells is generally diamond-shaped.

10. The prosthetic valve of claim 1, wherein the leaflets comprise exactly three leaflets, and wherein each of the leaflets comprises pericardium.

11. The prosthetic valve of claim 1, further comprising a polymer layer, wherein the polymer layer extends circumferentially over an exterior surface of an inflow end portion of the frame.

12. A prosthetic valve comprising:

a radially compressible and expandable frame having a longitudinal axis, an inflow end, and an outflow end, wherein the frame comprises a plurality of interconnected frame elements forming a plurality of cells, each of the cells defining an aperture, wherein the plurality of cells are arranged in exactly two rows of cells including a first circumferential row of first cells of the plurality of cells defining the inflow end of the frame and a second circumferential row of second cells of the plurality of cells defining the outflow end of the frame;

wherein each second cell in the second row of cells is formed by a pair of longitudinal frame posts forming opposing sides of the second cell, a pair of upper frame elements forming an outflow portion of the second cell, and a pair of lower frame elements forming an inflow portion of the second cell;

wherein a first upper frame element of each pair of upper frame elements has an upper end connected to a first end of a first longitudinal frame post of a respective pair of longitudinal frame posts, and a second upper frame element of the same pair of upper frame elements has an upper end connected to a first end of a second longitudinal frame post of the respective pair of longitudinal frame posts, and wherein the first and second upper frame elements have respective lower ends connected to each other in a V-shape having a first apex pointing toward the inflow end of the frame; and wherein a first lower frame element of each pair of lower frame elements has an upper end connected to a second end of the first longitudinal frame post of the respective pair of longitudinal frame posts, and a second lower frame element of the same pair of lower frame elements has an upper end connected to a second end of the second longitudinal frame post of the respective pair of longitudinal frame posts, and wherein the first and second lower frame elements have respective lower ends connected to each other in a V-shape having a second apex pointing toward the inflow end of the frame;

wherein the second end of each longitudinal frame post terminates at a frame junction defined by the second end of the longitudinal frame post and the upper ends of two adjacent lower frame elements of two adjacent second cells and no other components of the frame.

13. The prosthetic valve of claim 12, further comprising a plurality of leaflets disposed within a lumen of the frame, each of the leaflets having a leaflet base and a leaflet free edge opposite the leaflet base, wherein the leaflet free edges are configured to move between an open position and a closed position during opening-closing cycles associated with blood pressure differentials across the prosthetic valve.

14. The prosthetic valve of claim 12, further comprising a polymer layer, wherein the polymer layer extends circumferentially over at least a portion of each cell in the first circumferential row of cells.

15. The prosthetic valve of claim 12, wherein each first apex is a free apex that is not connected to other portions of the frame.

16. The prosthetic valve of claim 12, wherein each second cell is generally chevron-shaped.

17. A prosthetic valve comprising:

a radially compressible and expandable frame having a longitudinal axis, an inflow end, and an outflow end, wherein the frame comprises a plurality of interconnected angled frame elements forming a plurality of cells, each of the cells defining an aperture, wherein the cells are arranged in a first circumferential row of cells of the plurality of cells and a second circumferential row of cells of the plurality of cells, wherein the first row of cells is upstream of the second row of cells;

wherein an outflow portion of the second circumferential row of cells comprises a first circumferential row of angled frame elements interconnected with each other at a plurality of upper junctions and a plurality of lower junctions, wherein the upper junctions define the outflow end of the frame and the lower junctions point toward the inflow end of the frame, and wherein the lower junctions are not connected to other portions of the frame; and a plurality of longitudinal frame posts, wherein each of the upper junctions is connected to one of the longitudinal frame posts, which extends from the upper junction toward the inflow end of the frame in a direction that is parallel to the longitudinal axis;

wherein an inflow portion of the second circumferential row of cells comprises a second circumferential row of angled frame elements interconnected with each other at a plurality of upper junctions and a plurality of lower junctions, wherein a lower end of each longitudinal frame post terminates at a respective upper junction of the second circumferential row of angled frame elements which is not connected to other portions of the frame.

18. The prosthetic valve of claim 17, further comprising a plurality of leaflets disposed within a lumen of the frame, each of the leaflets having a leaflet base and a leaflet free edge opposite the leaflet base, wherein the leaflet free edges are configured to move between an open position and a closed position during opening-closing cycles associated with blood pressure differentials across the prosthetic valve.

* * * * *